US007834248B2

(12) United States Patent
Green et al.

(10) Patent No.: US 7,834,248 B2
(45) Date of Patent: Nov. 16, 2010

(54) PLANT SEED COMPRISING VERNOLIC ACID

(75) Inventors: Allan Green, Bradoon (AU); Surinder Singh, Downer (AU); Marit Lenman, Lund (SE); Sten Stymne, Svalóv (SE)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 864 days.

(21) Appl. No.: 11/699,817

(22) Filed: Jan. 30, 2007

(65) Prior Publication Data

US 2007/0209092 A1 Sep. 6, 2007

Related U.S. Application Data

(63) Continuation of application No. 09/981,124, filed on Oct. 17, 2001, now Pat. No. 7,589,253, which is a continuation-in-part of application No. 09/059,769, filed on Apr. 14, 1998, now Pat. No. 6,329,518.

(60) Provisional application No. 60/050,403, filed on Jun. 20, 1997, provisional application No. 60/043,706, filed on Apr. 16, 1997.

(30) Foreign Application Priority Data

Apr. 15, 1997 (AU) ................................ PO6223/97
Apr. 15, 1997 (AU) ................................ PO6226/97

(51) Int. Cl.
*A01H 5/00* (2006.01)

(52) U.S. Cl. ....................... 800/298; 800/281; 800/306; 800/312; 800/314; 800/320.1; 800/320.2; 800/322

(58) Field of Classification Search ........................ None
See application file for complete search history.

(56) References Cited

U.S. PATENT DOCUMENTS 6,329,518 B1  12/2001  Green et al.

FOREIGN PATENT DOCUMENTS

| WO | 8905852 | 6/1989 |
| WO | 9610074 | 4/1996 |
| WO | 9737033 | 10/1997 |

OTHER PUBLICATIONS

Bafor et al. (1993) "Biosynthesis of vernoleate (cis-12-eposyoctadeca-cis-9-enoate) in microsomal preparations from developing endosperm of *Euphorbia lagascae*", *Archives of Biochemistry and Biophysics*, 303(1):145-151.
Banas et al. (Feb. 1997) In: Williams, J.P., Mobasher, K.U. Lem, N.W. (Eds) Physiol-ogy, biochemistry and molecular biology of plants lipids. Kluwer Academic Publisher, Dordrecht. In press. "Biosynthesis of an Acetylenic Fatty Acid in Microsomal Preparations From Developing Seeds of *Crepis alpina*" pp. 57-59.
Blee et al. (1993), "Regio-an steroselectivity of cytochrome P-450 and peroxygenase-dependent formation of *Cis*-12, 13-epoxy-9(Z)-octadecenoic acid (vernolic acid) in *Euphorbia lagascae*", *Biochemical and Biophysical Research Communications* 197 (2) :778-784.
Blee et al. (1993), "Mechanism of reaction of fatty acid hydroperoxides with soybean peroxygenase", *The Journal of Biological Chemistry* 268(3):1708-1715.
Blee and Schuber (1990), "Efficient epoxidation of unsaturated fatty acids by a hydroperocide-dependent oxygenase", *The Journal of Biological Chemistry* 265(22):12887-12894.
Bozak et al. (1990) "Sequence analysis of ripening-related cytochrome P-450 cDNAs from avocado fruit", *Proc. Natl. Acad. Sci.* USA 87:3904-3908.
Dolferus et al. (1994), "Differential Interactions of promoter elements in stress responses of the *arabidopsis adh gene*" *Plant Physiol.* 105:1075-1087.
Engeseth and Stymne (Feb. 1996), "Desaturation of oxygenated fatty acids in *lesquerella* and other oil seeds" *Planta* 198:238-245.
Needleman and Wunsch (1970), "A General method applicable to the search for similarities in the amino acid sequence of two proteins" *J. Mol. Biol.* 48:443-453.
Shanklin et al. (1994), "Eight histidine residues are catalytically essential in a membrane-associated iron enzyme, stearoyl-coa desaturase, and are conserved in alkane hydroxylase and xylene monooxygenase" *Biochemistry* 33:12787-12794.
Valvekens et al. (1988), "*Agrobacterium tumefaciens*-mediated transformation of *Arabidopsis thaliana* root explants by using kanamycin selection", *Proc. Natl. Acad. Sci.* USA 85:5536-5540.
Capdevila, J.H. et al., "Cytochrome P-450 arachidonate oxygenase" (1990), Methods in Enzymology 187:385-394.
Christian, M.F. and Yu, S.J. , "Cytochrome p-450-dependent monooxygenase activity in the velvetbean caterpillar, *anticarsia gemmatalis hubner*" (1986), Comparative Biochemistry and Physiology 83C (1) :23-27.
Romero, M.F. et al., "An epoxygenase metabolite of arachidonic acid 5, 6 epoxy-eicosatrienoic acid mediates angiotensin-induced natriuresis in proximal tubular epithelium" (1991), Advances in Prostaglandin, Thromboxane and Leukotriene Research 21:205-208.
Laethem, R.M. et al., "Epoxidation of $C_{18}$ unsaturated fatty acids by cytochromes P4502C2 and P4502CAA" (Jun. 1996) Drug Metabolism and Disposition 24(6):664-668.

(Continued)

*Primary Examiner*—Elizabeth F McElwain
(74) *Attorney, Agent, or Firm*—John P. White; Cooper & Dunham LLP

(57) ABSTRACT

The present invention relates generally to novel genetic sequences that encode fatty acid epoxygenase enzymes, in particular fatty acid Δ12-epoxygenase enzymes from plants that are mixed function monooxygenase enzymes. More particularly, the present invention exemplifies cDNA sequences from *Crepis* spp. and *Vernonia galamensis* that encode fatty acid Δ12-epoxygenases. The genetic sequences of the present invention provide the means by which fatty acid metabolism may be altered or manipulated in organisms, such as, for example, yeasts, moulds, bacteria, insects, birds, mammals and plants, and more particularly in plants. The invention also extends to genetically modified oil-accumulating organisms transformed with the subject genetic sequences and to the oils derived therefrom. The oils thus produced provide the means for the cost-effective raw materials for use in the efficient production of coatings, resins, glues, plastics, surfactants and lubricants.

20 Claims, 19 Drawing Sheets

OTHER PUBLICATIONS

Lee, M. et al., "Identification of non-heme diiron proteins that catalyze triple bond and epoxy group formation" (May 8, 1998), Science 280:915-918.

Van de Loo, F.J. et al., "An oleate 12-hydroxylase from *Ricinus communis 1*.is a fatty acyl desaturase homolog" (Jul. 1995) Proc. Natl. Acad. Sci. USA 92:6743-6747.

Hamberg and Fahlstadius (1992) On the Specificity of a Fatty Acid Epoxygenase in Broad Bean (*Vicia faba* L.); *Plant Physiol.* 99:987-995.

Heppard et al. (1996) "Development and Growth Temperature Regulation of Two Different Microsomal ω-6 Desaturase Genes in Soybeans", *Plant Physiol.* 110:311-319.

Okuley et al. (1994) "Arabidopsis FAD2 Gene Encodes the Enzyme That Is Essential for Polyunsaturated Lipid Synthesis", *Plant Cell* 6:147-158.

```
         1                                                   50
Cpa12    .....MGAG GR.......... ..GRTSEKSV MERVSVDPVT FSLSELKQAI
CrepX    .....MGAG GR.......... ..GRTSEKSV MERVSVDPVT FSLSELKQAI
Vgal1    ......... .......... ......... ......... .........
Vgal     .....MGAG GRM........ NTTDDDQKNL FQRVPASKPP FSLADLKKAI
Crep1    ......MGGG GR......... ..GRTSQKPL MERVSVDP.P FTVSDLKQAI
L26296   .....MGAG GRMPV.....P TSSKKSETDT TKRVPCEKPP FSVGDLKKAI
X91139   .....MGAG GRMQV.....S PSPKKSETDI LKRVPCETPP FTVGELKKAI
L43921   .....MGAG GRTDV.....P PANRKSEVDP LKRVPFEKPQ FSLSQIKKAI
X92847   .....MGAG GRMSA.....P NGETEVKRNP LQKVPTSKPP FTVGDIKKAI
L43920   MGLAKETTMG GRGRV.....A KVEVQGK.KP LSRVPNTKPP FTVGQLKKAI
U22378   ......MGGG GRMSTVITSN NSEKKGGSSH LKRAPHTKPP FTLGDLKRAI
```

FIGURE 2A

```
       51                                                          100
Cpa12  PPHCFQRSVI RSSYVVVQDL IIAYIFYFLA NTYIPTLPTS LAY.LAWPVY
CrepX  PPHCFQRSVI RSSYVVVQDL IIAYIFYFLA NTYIPTLPHP LAY.LAWPLY
Vgall  .......... .......... .......... .......... ..........
Vgal   PPHCFQRSLL RSSYVVVHDL VVAYVFYYLA NTYIPLLPSP LAYLLAWPLY
Crep1  PPHCFKRSVI RSSYYIVHDA IIAYIFYFLA DKYIPILPAP LAY.LAWPLY
L26296 PPHCFKRSIP RSFSYLISDI IIASCFYVVA TNYFSLLPQP LSY.LAWPLY
X91139 PPHCFKRSIP RSFSYLIWDI IVASCFYVVA TTYFPLLPHP LSY.VAWPLY
L43921 PPHCFQRSVL RSFSYVVYDL TIAFCLYVVA THYFHLLPGP LSF.RGMAIY
X92847 PPHCFQRSLI RSFSYVVVDL ILVSIMYVVA NTYFHLLPSP YCY.IAWPIY
L43920 PPHCFQRSLL TSFSYVVYDL SEAF.IFYIA TTYFHLLPQP FS.LIAWPIY
U22378 PPHCFERSFV RSFSYVAYDV CLSFLFYSIA TNFFPYISSP LS.YVAQLVY

FIGURE 2B
```

```
        101
Cpal2   WFCQASVLTG  LWILGHECGH  HAFSNYTWFD  DTVGFILHSF  LLTPYFSWKF
CrepX   WFCQASVLTG  LWILGHECGH  HAYSNYTWVD  DTVGFIIHSF  LLTPYFSWKY
Vgall   ..........  ..........  .H HAFSDYQWID  DTVGFILHFA  LFTPYFSWKY
Vgal    WFCQGSILTG  VWVIGHECGH  HAFSDYQWID  DTVGFILHSA  LFTPYFSWKY
Crepl   WFCQASILTG  LWVIGHECGH  HAFSDYQWVD  DTVGFIIHSF  LMTPYFSWKY
L26296  WACQGCVLTG  INWVIAHECGH  HAFSDYQWLD  DTVGLIFHSF  LLVPYFSWKY
X91139  WACQGVVLTG  VWVIAHECGH  HAFSDYQWLD  DTVGLIFHSF  LLVPYFSWKY
L43921  WACQGCVITG  VWVIAHECGH  HAFSDYQLLD  DIVGLILHSA  LLVPYFSWKY
X92847  WICQGCVCTG  IWVNAHECGH  HAFSDYQWVD  DTVGLILHSA  LLVPYFSWKY
L43920  WVLQGCLLTG  VWVIAHECGH  HAFSKYQWVD  DVVGLTLHST  LLVPYFSWKI
U22378  WLFQGCILTG  LWVIGHECGH  HAFSEYQLAD  DIVGLIVHSA  LLVPYFSWKY
                                                                150
```

FIGURE 2C

```
        151                                                    200
Cpa12   SHRNHHSNTS  SIDNDEVYIP  KSKSKLARIY  KLLNNPPGRL  LVLIIMFTLG
CrepX   SHRNHHSNTS  SIDNDEVYIP  KSKSKLKRIY  KLLNNPPGRL  LVLVIMFTLG
Vgal1   SHRNHHANTN  SLVTDEVYIP  KVKSKVKIYS  KILNNPPGRV  FTLAFRLIVG
Vgal    SHRNHHANTN  SLDNDEVYIP  KVKSKVKIYS  KILNNPPGRV  FTLAFRLIVG
Crep1   SHRNHHANTN  SLDNDEVYIP  KSKAKVALYY  KVLNHPPGRL  LIMFITFTLG
L26296  SHRNHHSNTG  SLERDEVFVP  KQKSAIKWYG  KYLNNPLGRI  MMLTVQFVLG
X91139  SHRNHHSNTG  SLERDEVFVP  KKKSDIKWYG  KYLNNPLGRT  VMLTVQFTLG
L43921  SHRNHHSNTG  SLERDEVFVP  KQKSCIKWYS  KYLNNPLGRV  LTLAVTLTLG
X92847  SHRNHHSNTG  SLERDEVFVP  KPKSQLGWYS  KYLNNPLGRV  LSLTITLTLG
L43920  SHRNHHSNTG  SLDRDEVFVP  KPKSKVAWFS  KYLNNPLGRA  VSLLVTLTIG
U22378  SHRNHHSNIG  SLERDEVFVP  KSKSKISWYS  KYSNNPLGRV  LTLAATLLLG
```

FIGURE 2D

```
        201                                               250
Cpa12   FPLYLLTNIS GKKY.DRFAN HFDPMSPIFK ERERFQVFLS DLGLLAVFYG
CrepX   FPLYLLTNIS GKKY.DRFAN HFDPMSPIFK ERERFQVFLS DLGLLAVFYG
Vgal1   FPLYLFTNVS GKKY.ERFAN HFDPMSPIFT EREHVQVLLS DFGLIAVAYV
Vgal    FPLYLFTNVS GKKY ERFAN HFDPMSPIFT EREHVQVLLS DFGLIAVAYV
Crep1   FPLYLFTNIS GKKY.ERFAN HFDPMSPIFK ERERFQVLLS DLGLLAVAYG
L26296  WPLYLAFNVS GRPY.DGFAC HFFPNAPIYN DRERLQIYLS DAGILAVCFG
X91139  WPLYWAFNVS GRPYPEGFAC HFHPNAPIYN DRERLQIYVS DAGILAVCYG
L43921  WPLYLAFNVS GRPY.DRFAC HYDPYGPIYS DRERLQIYIS DAGVLAVVYG
X92847  WPLYLAFNVS GRPY.DRFAC HYDPYGPIYN DRERLQIFIS DAGVLGVCYL
L43920  WPMYLAFNVS GRPY.DSFAS HYHPYAPIYS NRERLLIYVS DVALFSVTYS
U22378  WPLYLAFNVS GRPY.DSFAC HYDPYGPIFS ERERLQIYIA DLGIFATTFV
```

FIGURE 2E

```
        251                                                      300
Cpa12   IKVAVANKGA AWVACMYGVP VLGVFTFFDV ITFLHHTHQS SPHYDSTEWN
CrepX   IKVAVANKGA AWVACMYGVP VLGVFTFFDV ITFLHHTHQS SPHYDSTEWN
Vga11   VRQAVLAKGG AWVMCIYGVP VLAVNAFFVL ITYLHHTHLS LPHYDSTEWD
Vgal    VRQAVLAKGG AWVMCIYGVP VLAVNAFFVL ITYLHHTHLS LPHYDSTEWD
Crep1   VKLAVAAKGA AWVTCIYGIP VLGVFIFFDI ITYLHHTHLS LPHYDSSEWN
L26296  LYRYAAAQGM ASMICLYGVP LLIVNAFLVL ITYLQHTHPS LPHYDSSEWD
X91139  LYRYAAAQGV ASMVCLYGVP LLIVNAFLVL ITYLQHTHPS LPHYTSSEWD
L43921  LFRLAMAKGL AWVVCVYGVP LLVVNGFLVL ITFLQHTHPA LPHYDSSEWD
X92847  LYRIALVKGL AWLVCVYGVP LLVVNGFLVL ITYLQHTHPS LPHYDSTEWD
L43920  LYRVATLKGL VWLLCVYGVP LLIVNGFLVL ITYLQHTHFA LPHYDSSEWD
U22378  LYQATMAKGL AWVMRIYGVP LLIVNCFLVM ITYLQHTHPA IPRYGSSEWD
```

FIGURE 2F

```
        301                                                           350
Cpal2   WIRGALSAID RDFGFLNSVF HDVTHTHVMH HLFSYIPHYH AKEARDAIKP
CrepX   WIRGALSAID RDFGFLNSVF HDVTHTHVMH HLFSYIPHYH AKEARDAIKP
Vgal1   WLR....... .......... .......... .......... ..........
Vgal    WIKGALCTID RDFGFLNRVF HDVTHTHVLH HLISYIPHYH AKEARDAIKP
Crepl   WLRGALSTID RDFGFLNSVL HDVTHTHVMH HLFSYIPHYH AKEARDAINT
L26296  WLRGALATVD RDYGILNKVF HNITDTHVAH HLFSTMPHYN AMEATKAIKP
X91139  WLRGALATVD RDYGILNKVF HNITDTHVAH HLFSTMPHYH AMEVTKAIKP
L43921  WLRGALATVD RDYGILNKVF HNITDTHVAH HLFSTMPHYH AMEATKAIKP
X92847  WLRGALATCD RDYGILNKVF HNITDTHVVH HLFSTMPHYH AMEATKAVKP
L43920  WLKGALATMD RDYGILNKVF HHITDTHVAH HLFSTMPHYH AMEATNAIKP
U22378  WLRGAMVTVD RDYGILNKVF HNIADTHVAH HLFATVPHYH AMEATKAIKP
```

FIGURE 2G

```
        351                                                    398
Cpa12   ILGDFYMIDR TPILKAMWRE GRECMYIEPD S..KLKGVYW Y.HKL
CrepX   ILGDFYMIDR TPILKAMWRE GRECMYIEPD S..KLKGVYW Y HKL
Vga11   .......... .......... .......... .......... .....
Vga1    VLGEYYKIDR TPIVKAMWRE AKNAYTLRLM KIASTKAHTG TTSCKARS
Crep1   VLGDFYMIDR TPILKAMWRE AKECIFIEPE KGRESKGVYW Y.NKF
L26296  ILGDYYQFDG TPWYVAMYRE AKECIYVEPD REGDKKGVYW YNNKL
X91139  ILGDYYQFDG TPWYKAMWRE AKECIYVEPD RQGEKKGVFW YNNKL
L43921  ILGEYYRFDE TPFVKAMWRE ARECIYVEPD QSTESKGVFW YNNKL
X92847  LLGDYYQFDG TPIYKEMWRE AKECLYVEKD ESSQGKGVFW YNNKL
L43920  ILGEYYQFDD TPFYKALWRE ARECLYVEPD EGTSEKGVYW YRNKY
U22378  IMGEYYRYDG TPFYKALWRE AKECLFVEPD EGAPTQGVFW YRNKY
```

PLANT SEED COMPRISING VERNOLIC ACID

RELATED APPLICATION DATA

This application is a continuation of U.S. Ser. No. 09/981,124, filed Oct. 17, 2001, now U.S. Pat. No. 7,589,253, issued Sep. 15, 2009 which is a continuation-in-part of U.S. Ser. No. 09/059,769, filed Apr. 14, 1998, now U.S. Pat. No. 6,329,518, issued Dec. 11, 2001, which claims the benefit of U.S. Provisional Application No. 60/050,403, filed Jun. 20, 1997, and U.S. Provisional Application No. 60/043,706, filed Apr. 16, 1997, and claims priority of Australian Patent Application PO6223/97, filed Apr. 15, 1997, and Australian Patent Application PO6226/97, filed Apr. 15, 1997, the contents of all of which are hereby incorporated by reference into the subject application.

FIELD OF THE INVENTION

The present invention relates generally to novel genetic sequences that encode fatty acid epoxygenase enzymes. In particular, the present invention relates to genetic sequences that encode fatty acid Δ12-epoxygenase enzymes as defined herein. More particularly, the present invention provides cDNA and genomic gene sequences that encode plant fatty acid epoxygenases, in particular from *Crepis palaestina* or *Vernonia galamensis*. The genetic sequences of the present invention provide the means by which fatty acid metabolism may be altered or manipulated in organisms such as yeasts, moulds, bacteria, insects, birds, mammals and plants, in particular to convert unsaturated fatty acids to epoxy fatty acids therein. The invention extends to genetically modified oil-accumulating organisms transformed with the subject genetic sequences and to the oils derived therefrom. The oils thus produced provide the means for the cost-effective raw materials for use in the efficient production of coatings, resins, glues, plastics, surfactants and lubricants, amongst others.

GENERAL

Those skilled in the art will be aware that the present invention is subject to variations and modifications other than those specifically described herein. It is to be understood that the invention includes all such variations and modifications. The invention also includes all such steps, features, compositions and compounds referred to or indicated in this specification, individually or collectively, and any and all combinations of any two or more of said steps or features.

Throughout this specification, unless the context requires otherwise, the word "comprise", or variations such as "comprises" or "comprising", will be understood to imply the inclusion of a stated integer or group of integers but not the exclusion of any other integer or group of integers.

Bibliographic details of the publications referred to by author in this specification are collected at the end of the description.

This specification contains nucleotide sequence information prepared using the program PatentIn Version 3.1 presented herein after the claims. Each nucleotide sequence is identified in the sequence listing by the numeric indicator <210> followed by the sequence identifier [e.g. <210>1, <210>2, etc]. The length, type of sequence [DNA, protein (PRT), etc] and source organism for each nucleotide sequence are indicated by information provided in the numeric indicator fields <211>, <212> and <213>, respectively. Nucleotide sequences referred to in the specification are defined by the term "SEQ ID NO:", followed by the sequence identifier [e.g. SEQ ID NO: 1 refers to the sequence in the sequence listing designated as <400>1].

BACKGROUND TO THE INVENTION

There is considerable interest world-wide in producing chemical feedstock, such as fatty acids, for industrial use from renewable plant sources rather than from non-renewable petrochemicals. This concept has broad appeal to manufacturers and consumers on the basis of resource conservation and provides a significant opportunity to develop new industrial crops for agriculture.

There is a diverse array of unusual fatty acids in nature and these have been well characterized (Badam & Patil, 1981; Smith, 1970). Many of these unusual fatty acids have industrial potential and this has led to interest in domesticating such species to enable agricultural production of particular fatty acids.

One class of fatty acids of particular interest are the epoxy-fatty acids, consisting of an acyl chain in which two adjacent carbon bonds are linked by an epoxy bridge. Due to their high reactivity, they have considerable application in the production of coatings, resins, glues, plastics, surfactants and lubricants. These fatty acids are currently produced by chemical epoxidation of vegetable oils, mainly soybean oil and linseed oil, however this process produces mixtures of multiple and isomeric forms and involves significant processing costs.

Attempts are being made by others to develop some wild plants that contain epoxy fatty acids (e.g. *Euphorbia lagascae*, or *Vernonia galamensis*) into commercial sources of these oils. However, problems with agronomic suitability and low yield potential severely limit the commercial utility of traditional plant breeding and cultivation approaches.

The rapidly increasing sophistication of recombinant DNA technology is greatly facilitating the efficiency of commercially-important industrial processes, by the expression of genes isolated from a first organism or species in a second organism or species to confer novel phenotypes thereon. More particularly, conventional industrial processes can be made more efficient or cost-effective, resulting in greater yields per unit cost by the application of recombinant DNA techniques.

Moreover, the appropriate choice of host organism for the expression of a genetic sequence of interest provides for the production of compounds that are not normally produced or synthesized by the host, at a high yield and purity.

However, despite the general effectiveness of recombinant DNA technology, the isolation of genetic sequences which encode important enzymes in fatty acid metabolism, in particular the genes which encode the fatty acid Δ12-epoxygenase enzymes responsible for producing 12,13-epoxy-9-octadecenoic acid (vernolic acid) and 12,13-epoxy-9,15-octadecadienoic acid, amongst others, remains a major obstacle to the development of genetically-engineered organisms which produce these fatty acids.

Until the present invention, there were only limited biochemical data indicating the nature of fatty acid epoxygenase enzymes, in particular Δ12-epoxygenases. However, in *Euphorbia lagascae*, the formation of 12,13-epoxy-9-octadecenoic acid (vernolic acid) from linoleic acid appears to be catalyzed by a cytochrome-P450-dependent Δ12 epoxygenase enzyme (Bafor et al., 1993; Blee et al., 1994). Additionally, developing seed of linseed plants have the capability to convert added vernolic acid to 12,13-epoxy-9,15-octadecadienoic acid by an endogenous Δ15 desaturase (Engeseth and Stymne, 1996). Epoxy-fatty acids can also be produced by a peroxide-dependent peroxygenase in plant tissues (Blee and Schuber, 1990).

In work leading up to the present invention, the inventors sought to isolate genetic sequences which encode genes which are important for the production of epoxy-fatty acids, such as 12,13-epoxy-9-octadecenoic acid (vernolic acid) or 12,13-epoxy-9,15-octadecadienoic acid and to transfer these genetic sequences into highly productive commercial oilseed plants and/or other oil accumulating organisms.

SUMMARY OF THE INVENTION

One aspect of the invention provides an isolated nucleic acid which encodes or is complementary to an isolated nucleic acid which encodes a fatty acid epoxygenase.

A second aspect of the invention provides an isolated nucleic acid which hybridizes under at least low stringency conditions to at least 20 contiguous nucleotides of SEQ ID NOs:1 or 3 or 5 or 19 or 19, or a complementary sequence thereto.

A further aspect of the invention provides isolated nucleic acid comprising a sequence of nucleotides selected from the group consisting of:
(i) a nucleotide sequence that is at least 65% identical to a sequence selected from the group consisting of: SEQ ID NO: 1, SEQ ID NO: 3, SEQ ID NO: 5, and SEQ ID NO: 19;
(ii) a nucleotide sequence that encodes an amino acid sequence that is at least about 50% identical to a sequence selected from the group consisting of: SEQ ID NO: 2, SEQ ID NO: 4, SEQ ID NO: 6, and SEQ ID NO: 20; and
(iii) a nucleotide sequence that is complementary to (i) or (ii).

A further aspect of the invention provides a gene construct that comprises the isolated nucleic acid supra, in either the sense or antisense orientation, in operable connection with a promoter sequence.

A further aspect of the invention provides a method of altering the level of epoxy fatty acids in a cell, tissue, organ or organism, said method comprising expressing a sense, antisense, ribozyme or co-suppression molecule comprising the isolated nucleic acid supra in said cell, tissue, organ or organism for a time and under conditions sufficient for the level of epoxy fatty acids therein to be increased or reduced.

A further aspect of the invention provides a method of producing a recombinant enzymatically active epoxygenase polypeptide in a cell, said method comprising expressing the isolated nucleic acid supra in said cell for a time and under conditions sufficient for the epoxygenase encoded therefor to be produced.

A further aspect of the invention provides a method of producing a recombinant enzymatically active epoxygenase polypeptide in a cell, said method comprising the steps of:
(i) producing a gene construct which comprises the isolated nucleic acid supra placed operably under the control of a promoter capable of conferring expression on said genetic sequence in said cell, and optionally an expression enhancer element;
(ii) transforming said gene construct into said cell; and
(iii) selecting transformants which express a functional epoxygenase encoded by the genetic sequence at a high level.

A still further aspect of the invention provides a method of producing a recombinant and enzymatically active epoxygenase polypeptide in a transgenic plant comprising the steps of:
(i) producing a gene construct which comprises the isolated nucleic acid supra placed operably under the control of a seed-specific promoter and optionally an expression enhancer element, wherein said genetic sequences is also placed upstream of a transcription terminator sequence;
(ii) transforming said gene construct into a cell or tissue of said plant; and
(iii) selecting transformants which express a functional epoxygenase encoded by the genetic sequence at a high level in seeds.

A further aspect of the invention provides a recombinant epoxygenase polypeptide or functional enzyme molecule.

A further aspect of the invention provides a recombinant epoxygenase which comprises a sequence of amino acids set forth in any one of SEQ ID NOs: 2 or 4 or 6 or 20 or 20 or a homologue, analogue or derivative thereof which is at least about 50% identical thereto. More preferably, the percentage identity to any one of SEQ ID NOs: 2 or 4 or 6 or 20 or 20 is at least about 65%.

A still further aspect of the invention provides a method of producing an epoxy fatty acid in a cell, tissue, organ or organism, said method comprising incubating a cell, tissue, organ or organism which expresses an enzymatically active recombinant epoxygenase with a fatty acid substrate and preferably, an unsaturated fatty acid substrate, for a time and under conditions sufficient for at least one carbon bond, preferably a carbon double bond, of said substrate to be converted to an epoxy group.

A further aspect of the invention provides an immunologically interactive molecule which binds to the recombinant epoxygenase polypeptide described herein or a homologue, analogue or derivative thereof.

BRIEF DESCRIPTION OF THE DRAWINGS

FIG. 2 is a schematic representation showing the alignment of the amino acid sequences of the epoxygenase polypeptide of *Crepis palaestina* (Cpa12; SEQ ID NO: 2), a further epoxygenase derived from *Crepis* sp. other than *C. palaestina* which produces high levels of vernolic acid (CrepX; SEQ ID NO: 4), a partial amino acid sequence of an epoxygenase polypeptide derived from *Vernonia galamensis* (Vgal1; SEQ ID NO: 6), a full-length amino acid sequence of an epoxygenase polypeptide derived from *Vernonia galamensis* (SEQ ID NO: 20), the amino acid sequence of the Δ12 acetylenase of *Crepis alpina* (Crep1; SEQ ID NO: 8), the Δ12 desaturase of *A. thaliana* (L26296; SEQ ID NO: 9), *Brassica juncea* (X91139; SEQ ID NO: 10), *Glycine max* (L43921; SEQ ID NO: 11), *Solanum commersonii* (X92847; SEQ ID NO: 12) and *Glycine max* (L43920; SEQ ID NO: 13), and the Δ12 hydroxylase of *Ricinus communis* (U22378; SEQ ID NO: 14). Underlined are three histidine-rich motifs that are conserved in non-heme containing mixed-function monooxygenases.

DETAILED DESCRIPTION OF THE PREFERRED EMBODIMENTS

Figure 1:
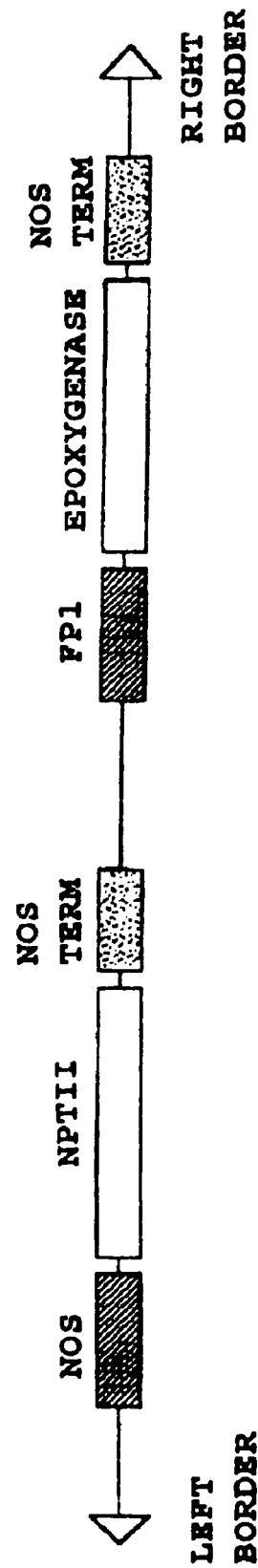
FIG. 1 is a linear representation of an expression plasmid comprising an epoxygenase structural gene, placed operably under the control of the truncated napin promoter (FP1; right-hand hatched box) and placed upstream of the NOS terminator sequence (right-hand stippled box). The epoxygenase genetic sequence is indicated by the right-hand open rectangular box. The construct also comprises the NOS promoter (left-hand hatched box) driving expression of the NPTII gene (left-hand open box) and placed upstream of the NOS terminator (left-hand stippled box). The left and right border sequences of the *Agrobacterium tumefaciens* Ti plasmid are also indicated.

One aspect of the present invention provides an isolated nucleic acid which encodes or is complementary to an isolated nucleic acid which encodes a fatty acid epoxygenase.

Wherein the isolated nucleic acid of the invention encodes an enzyme which is involved in the direct epoxidation of arachidonic acid, it is particularly preferred that the subject nucleic acid is derived from a non-mammalian source.

As used herein, the term "derived from" shall be taken to indicate that a particular integer or group of integers has originated from the species specified, but has not necessarily been obtained directly from the specified source.

The term "non-mammalian source" refers to any organism other than a mammal or a tissue or cell derived from same. In the present context, the term "derived from a non-mammalian source" shall be taken to indicate that a particular integer or group of integers has been derived from bacteria, yeasts, birds, amphibians, reptiles, insects, plants, fungi, moulds and algae or other non-mammal.

In a preferred embodiment of the present invention, the source organism is any such organism possessing the genetic capacity to synthesize epoxy fatty acids. More preferably, the source organism is a plant such as, but not limited to *Chrysanthemum* spp., *Crepis* spp., *Euphorbia* spp. and *Vernonia* spp., amongst others.

Even more preferably, the source organism is selected from the group consisting of: *Crepis biennis*, *Crepis aurea*, *Crepis conyzaefolia*, *Crepis intermedia*, *Crepis occidentalis*, *Crepis palaestina*, *Crepis vesicaria*, *Crepis xacintha*, *Euphorbia lagascae* and *Vernonia galamensis*. Additional species are not excluded.

In a particularly preferred embodiment of the present invention, the source organism is a *Crepis* sp. comprising high levels of vernolic acid such as *Crepis palaestina*, amongst others or alternatively, *Vernonia galamensis*.

Wherein the isolated nucleic acid of the invention encodes a Δ6-epoxygenase or Δ9-epoxygenase enzyme or Δ12-epoxygenase or Δ15-epoxygenase enzyme, or at least encodes an enzyme which is not involved in the direct epoxidation of arachidonic acid, the subject nucleic acid may be derived from any source producing said enzyme, including, but not limited to, yeasts, moulds, bacteria, insects, birds, mammals and plants.

The nucleic acid of the invention according to any of the foregoing embodiments may be DNA, such as a gene, cDNA molecule, RNA molecule or a synthetic oligonucleotide molecule, whether single-stranded or double-stranded and irrespective of any secondary structure characteristics unless specifically stated.

Reference herein to a "gene" is to be taken in its broadest context and includes:

(i) a classical genomic gene consisting of transcriptional and/or translational regulatory sequences and/or a coding region and/or non-translated sequences (i.e. introns, 5'- and 3'-untranslated sequences);or (ii) mRNA or cDNA corresponding to the coding regions (i.e. exons) and 5'- and 3'-untranslated sequences of the gene.

The term "gene" is also used to describe synthetic or fusion molecules encoding all or part of a functional product. Preferred epoxygenase genes of the present invention may be derived from a natural epoxygenase gene by standard recombinant techniques. Generally, an epoxygenase gene may be subjected to mutagenesis to produce single or multiple nucleotide substitutions, deletions and/or additions.

Insertions are those variants in which one or more nucleotides are introduced into a predetermined site in the nucleotide sequence, although random insertion is also possible with suitable screening of the resulting product. Nucleotide insertions include 5' and 3' terminal fusions as well as intra-sequence insertions of single or multiple nucleotides.

Deletions are variants characterized by the removal of one or more nucleotides from the sequence.

Substitutions are those variants in which at least one nucleotide in the sequence has been removed and a different nucleotide inserted in its place. Such a substitution may be "silent" in that the substitution does not change the amino acid defined by the codon. Alternatively, a conservative substitution may alter one amino acid for another similar acting amino acid, or an amino acid of like charge, polarity, or hydrophobicity.

In the context of the present invention, the term "fatty acid epoxygenase" shall be taken to refer to any enzyme or functional equivalent or enzymatically-active derivative thereof that catalyzes the biosynthesis of an epoxy fatty acid, by converting a carbon bond of a fatty acid to an epoxy group and preferably, by converting a carbon double bond of an unsaturated fatty acid to an epoxy group. Although not limiting the invention, a fatty acid epoxygenase may catalyze the biosynthesis of an epoxy fatty acid selected from the group consisting of: (i) 12,13-epoxy-9-octadecenoic acid (vernolic acid); (ii) 12,13-epoxy-9,15-octadecadienoic acid; (iii) 15,16-epoxy-9,12-octadecadienoic acid; (iv) 9,10-epoxy-12-octadecenoic acid; and (v) 9,10-epoxy-octadecanoic acid.

The term "epoxy", or "epoxy group" or "epoxy residue" will be known by those skilled in the art to refer to a three member ring comprising two carbon atoms and an oxygen atom linked by single bonds as follows:

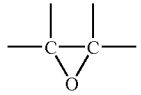

Accordingly, the term "epoxide" refers to a compound that comprise at least one epoxy group as herein before defined.

Those skilled in the art are aware that fatty acid nomenclature is based upon the length of the carbon chain and the position of unsaturated carbon atoms within that carbon chain. Thus, fatty acids are designated using the shorthand notation:

wherein the double bonds are cis unless otherwise indicated. For example, palmitic acid (n-hexadecanoic acid) is a saturated 16-carbon fatty acid (i.e. 16:0), oleic acid (octadecenoic acid) is an unsaturated 18-carbon fatty acid with one double bond between C-9 and C-10 (i.e. $18:1^{\Delta 9}$), and linoleic acid (octadecadienoic acid) is an unsaturated 18-carbon fatty acid with two double bonds between C-9 and C-10 and between C-12 and C-13 (i.e. $18:2^{\Delta 9,12}$).

However, in the present context an epoxygenase enzyme may catalyze the conversion of any carbon bond to an epoxy group or alternatively, the conversion of any double in an unsaturated fatty acid substrate to an epoxy group. In this regard, it is well-known by those skilled in the art that most mono-unsaturated fatty acids of higher organisms are 18-carbon unsaturated fatty acids (i.e. $18:1^{\Delta 9}$), while most polyunsaturated fatty acids derived from higher organisms are 18-carbon fatty acids with at least one of the double bonds therein located between C-9 and C-10. Additionally, bacteria also possess C16-mono-unsaturated fatty acids. Moreover, the epoxygenase of the present invention may act on more than a single fatty acid substrate molecule and, as a consequence, the present invention is not to be limited by the nature of the substrate molecule upon which the subject epoxygenase enzyme acts.

Preferably, the substrate molecule for the epoxygenase of the present invention is an unsaturated fatty acid comprising at least one double bond.

Furthermore, epoxygenase enzymes may act upon any number of carbon atoms in any one substrate molecule. For example, they may be characterized as Δ6-epoxygenase, Δ9-epoxygenase, Δ12-epoxygenase or Δ15-epoxygenase enzymes amongst others. Accordingly, the present invention is not limited by the position of the carbon atom in the substrate upon which an epoxygenase enzyme may act.

The term "Δ6-epoxygenase" as used herein shall be taken to refer to an epoxygenase enzyme which catalyzes the conversion of the Δ6 carbon bond of a fatty acid substrate to a Δ6 epoxy group and preferably, catalyzes the conversion of the Δ6 double bond of at least one unsaturated fatty acid to a Δ6 epoxy group.

The term "Δ9-epoxygenase" as used herein shall be taken to refer to an epoxygenase enzyme which catalyzes the conversion of the Δ9 carbon bond of a fatty acid substrate to a Δ9 epoxy group and preferably, catalyzes the conversion of the Δ9 double bond of at least one unsaturated fatty acid to a Δ9 epoxy group.

As used herein, the term "Δ12-epoxygenase" shall be taken to refer to an epoxygenase enzyme which catalyzes the conversion of the Δ12 carbon bond of a fatty acid substrate to a Δ12 epoxy group and preferably, catalyzes the conversion of the Δ12 double bond of at least one unsaturated fatty acid to a Δ12 epoxy group.

As used herein, the term "Δ15-epoxygenase" shall be taken to refer to an epoxygenase enzyme which catalyzes the conversion of the Δ15 carbon bond of a fatty acid substrate to a Δ15 epoxy group and preferably, catalyzes the conversion of the Δ15 double bond of at least one unsaturated fatty acid to a Δ15 epoxy group.

The present invention clearly extends to genetic sequences which encode all of the epoxygenase enzymes listed supra, amongst others.

In one preferred embodiment of the invention, the isolated nucleic acid encodes a fatty acid epoxygenase enzyme which converts at least one carbon bond in palmitoleic acid ($16:1^{\Delta 9}$), oleic acid ($18:1^{\Delta 9}$), linoleic acid ($18:2^{\Delta 9,12}$), linolenic acid ($18:3^{\Delta 9,12,15}$), or arachidonic acid ($20:4^{\Delta 5,8,11,14}$) to an epoxy bond. Preferably, the carbon bond is a carbon double bond.

More preferably, the isolated nucleic acid of the invention encodes a fatty acid epoxygenase enzyme that at least converts one or both double bonds in linoleic acid to an epoxy group. According to this embodiment, an epoxygenase which converts both the Δ9 and the Δ12 double bonds of linoleic acid to an epoxy group may catalyze such conversions independently of each other such that said epoxygenase is a Δ9-epoxygenase and/or a Δ12-epoxygenase enzyme as herein before defined.

In an alternative preferred embodiment, the fatty acid epoxygenase of the present invention is a Δ12-epoxygenase, a Δ15-epoxygenase or a Δ9-epoxygenase as herein before defined.

More preferably, the fatty acid epoxygenase of the invention is a Δ12-epoxygenase as herein before defined.

In a particularly preferred embodiment of the invention, there is provided an isolated nucleic acid which encodes linoleate Δ12-epoxygenase, the enzyme which at least converts the Δ12 double bond of linoleic acid to a Δ12-epoxy group, thereby producing 12,13-epoxy-9-octadecenoic acid (vernolic acid).

Although not limiting the present invention, the preferred source of the Δ12-epoxygenase of the invention is a plant, in particular *Crepis palaestina* or a further *Crepis* sp. which is distinct from *C. palaestina* but contains high levels of vernolic acid, or *Vernonia galamensis*.

According to this embodiment, a Δ12-epoxygenase may catalyze the conversion of palmitoleic acid to 9,10-epoxy-palmitic acid and/or the conversion of oleic acid to 9,10-epoxy-stearic acid and/or the conversion of linoleic acid to any one or more of 9,10-epoxy-12-octadecenoic acid or 12,13-epoxy-9-octadecenoic acid or 9,10,12,13-diepoxy-stearic acid and/or the conversion of linolenic acid to any one or more of 9,10-epoxy-12,15-octadecadienoic acid or 12,13-epoxy-9,15-octadecadienoic acid or 15,16-epoxy-octadecadienoic acid or 9,10,12,13-diepoxy-15-octadecenoic acid or 9,10,15,16-diepoxy-12-octadecenoic acid or 12,13,15,16-diepoxy-9-octadecenoic acid or 9,10,12,13,15,16-triepoxy-stearic acid and/or the conversion of arachidonic acid to any one or more of 5,6-epoxy-8,11,14-tetracosatrienoic acid or 8,9-epoxy-5,11,14-tetracosatrienoic acid or 11,12-epoxy-5,8,14-tetracosatrienoic acid or 14,15-epoxy-5,8,11-tetracosatrienoic acid or 5,6,8,9-diepoxy-11,14-tetracosadienoic acid or 5,6,11,12-diepoxy-8,14-tetracosadienoic acid or 5,6,14,15-diepoxy-8,11-tetracosadienoic acid or 8,9,11,12-diepoxy-5,14-tetracosadienoic acid or 8,9,14,15-diepoxy-5,11-tetracosadienoic acid or 11,12,14,15-diepoxy-5,8-tetracosadienoic acid or 5,6,8,9,11,12-triepoxy-14-tetracosenoic acid or 5,6,8,9,14,15-triepoxy-11-tetracosenoic acid or 5,6,11,12,14,15-triepoxy-8-tetracosenoic acid or 8,9,11,12,14,15-triepoxy-5-tetracosenoic acid, amongst others.

Those skilled in the art may be aware that not all substrates listed supra may be derivable from a natural source, but notwithstanding this, may be produced by chemical synthetic means. The conversion of both natural and synthetic unsaturated fatty acids to epoxy fatty acids is clearly within the scope of the present invention.

The present invention is particularly directed to those epoxygenase enzymes that are mixed-function monooxygenase enzymes, and nucleic acids encoding said enzymes, and uses of said enzymes and nucleic acids. Accordingly, it is particularly preferred that the nucleic acid of the invention encode a fatty acid epoxygenase which is a mixed-function monooxygenase enzyme.

In the context of the present invention, the term "mixed-function monooxygenase enzyme" shall be taken to refer to any epoxygenase polypeptide that comprises an amino acid sequence comprising three histidine-rich regions as follows:
(i) His-(Xaa)$_{3-4}$-His (SEQ ID NO: 21 and SEQ ID NO: 22);
(ii) His-(Xaa)$_{2-3}$-His-His (SEQ ID NO: 23 and SEQ ID NO: 24); and
(iii) His-(Xaa)$_{2-3}$-His-His (SEQ ID NO: 23 and SEQ ID NO: 24), wherein His designates histidine, Xaa designates any naturally-occurring amino acid residue as set forth in Table 1 herein, the integer (Xaa)$_{3-4}$ refers to a sequence of amino acids comprising three or four repeats of Xaa, and the integer (Xaa)$_{2-3}$ refers to a sequence of amino acids comprising two or three repeats of Xaa.

In the exemplification of the invention described herein, the inventors provide isolated cDNAs that comprise nucleotide sequences encoding the Δ12-epoxygenase polypeptides of *Crepis palaestina* and *Vernonia galamensis*. Each exemplified full-length amino acid sequence encoded by said cDNAs which includes the three characteristic amino acid sequence motifs of a mixed-function monooxygenase enzyme as herein before defined. Close sequence identity between the amino acid sequences of the Δ12-epoxygenase enzymes from *C. palaestina* (SEQ ID NO: 2), an unidentified *Crepis* sp (SEQ ID NO: 4), and *Vernonia galamensis* (SEQ ID NO: 20), suggests functional similarity between these polypeptides. In contrast, the amino acid sequences of these epoxygenases have lower identity to the amino acid sequences of a fatty acid desaturase or a fatty acid hydroxylase.

It is even more preferred that the epoxygenase of the present invention at least comprises a sequence of amino acids which comprises three histidine-rich regions as follows:
(i) His-Glu-Cys-Gly-His-His (SEQ ID NO: 15);
(ii) His-Arg-Asn-His-His (SEQ ID NO: 16); and
(iii) His-Val-Met-His-His (SEQ ID NO: 17) or His-Val-Leu-His-His (SEQ ID NO: 18), wherein His designates histidine, Glu designates glutamate, Cys designates cysteine, Gly designates glycine, Arg designates arginine, Asn designates asparagine, Val designates valine, Met designates methionine and Leu designates leucine.

The present invention clearly extends to epoxygenase genes derived from other species, including the epoxygenase genes derived from *Chrysanthemum* spp. and *Euphorbia lagascae*, amongst others.

In a preferred embodiment, whilst not limiting the present invention, the epoxygenase genes of other species which are encompassed by the present invention encode mixed-function monooxygenase enzymes. The present invention further extends to the isolated or recombinant polypeptides encoded by such genes and uses of said genes and polypeptides.

The invention described according to this embodiment does not encompass nucleic acids which encode enzyme activities other than epoxygenase activities as defined herein, in particular the Δ12-desaturase enzymes derived from *Arabidopsis thaliana*, *Brassica juncea*, *Brassica napus* or *Glycine max*, amongst others, which are known to contain similar histidine-rich motifs.

In the present context, "homologues" of an amino acid sequence refer to those amino acid sequences or peptide sequences which are derived from polypeptides, enzymes or proteins of the present invention or alternatively, correspond substantially to the amino acid sequences listed supra, notwithstanding any naturally-occurring amino acid substitutions, additions or deletions thereto.

For example, amino acids may be replaced by other amino acids having similar properties, for example hydrophobicity, hydrophilicity, hydrophobic moment, antigenicity, propensity to form or break α-helical structures or β-sheet structures, and so on. Alternatively, or in addition, the amino acids of a homologous amino acid sequence may be replaced by other amino acids having similar properties, for example hydrophobicity, hydrophilicity, hydrophobic moment, charge or antigenicity, and so on.

Naturally-occurring amino acid residues contemplated herein are described in Table 1.

A homologue of an amino acid sequence may be a synthetic peptide produced by any method known to those skilled in the art, such as by using Fmoc chemistry.

Alternatively, a homologue of an amino acid sequence may be derived from a natural source, such as the same or another species as the polypeptides, enzymes or proteins of the present invention. Preferred sources of homologues of the amino acid sequences listed supra include any of the sources contemplated herein.

"Analogues" of an amino acid sequence encompass those amino acid sequences which are substantially identical to the amino acid sequences listed supra notwithstanding the occurrence of any non-naturally occurring amino acid analogues therein.

Preferred non-naturally occurring amino acids contemplated herein are listed below in Table 2.

The term "derivative" in relation to an amino acid sequence shall be taken to refer hereinafter to mutants, parts, fragments or polypeptide fusions of the amino acid sequences listed supra. Derivatives include modified amino acid sequences or peptides in which ligands are attached to one or more of the amino acid residues contained therein, such as carbohydrates, enzymes, proteins, polypeptides or reporter molecules such as radionuclides or fluorescent compounds. Glycosylated, fluorescent, acylated or alkylated forms of the subject peptides are also contemplated by the present invention. Additionally, derivatives may comprise fragments or parts of an amino acid sequence disclosed herein and are within the scope of the invention, as are homopolymers or heteropolymers comprising two or more copies of the subject sequences.

Procedures for derivatizing peptides are well-known in the art.

Substitutions encompass amino acid alterations in which an amino acid is replaced with a different naturally-occurring or a non-conventional amino acid residue. Such substitutions may be classified as "conservative", in which case an amino acid residue is replaced with another naturally-occurring amino acid of similar character, for example Gly⇔Ala, Val⇔Ile⇔Leu, Asp⇔Glu, Lys⇔Arg, Asn⇔Gln or Phe⇔Trp⇔Tyr.

Substitutions encompassed by the present invention may also be "non-conservative", in which an amino acid residue which is present in a repressor polypeptide is substituted with an amino acid having different properties, such as a naturally-occurring amino acid from a different group (e.g. substituted a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Amino acid deletions will usually be of the order of about 1-10 amino acid residues, while insertions may be of any length. Deletions and insertions may be made to the N-terminus, the C-terminus or be internal deletions or insertions. Generally, insertions within the amino acid sequence will be smaller than amino- or carboxyl-terminal fusions and of the order of 1-4 amino acid residues.

The present invention clearly extends to the subject isolated nucleic acid when integrated into the genome of a cell as an addition to the endogenous cellular complement of epoxygenase genes. Alternatively, wherein the host cell does not normally encode enzymes required for epoxy fatty acid biosynthesis, the present invention extends to the subject isolated nucleic acid when integrated into the genome of said cell as an addition to the endogenous cellular genome.

TABLE 1

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |

TABLE 2-continued

| Non-conventional amino acid | Code |
|---|---|
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenylethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomo phenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomo phenylalanine | Nmhphe |
| N-(N-(3,3-diphenylpropyl)Nnbhmcarbamylmethyl)glycine | Nnbhe |

A second aspect of the present invention provides an isolated nucleic acid which comprises the sequence of nucleotides set forth in any one of SEQ ID NOs:1 or 3 or 5 or 19 or a complementary sequence thereto, or a homologue, analogue or derivative thereof.

For the purposes of nomenclature, the nucleotide sequence set forth in SEQ ID NO: 1 is derived from *Crepis palaestina* and encodes the mixed function monooxygenase sequence or mixed function monooxygenase-like sequence set forth in SEQ ID NO: 2. As exemplified herein, the amino acid sequence set forth in SEQ ID NO: 2 has epoxygenase activity, more particularly Δ12-epoxygenase activity.

The nucleotide sequence set forth in SEQ ID NO: 3 corresponds to a cDNA derived from a *Crepis* sp. other than *C. palaestina* comprising high levels of vernolic acid. The amino acid sequence set forth in SEQ ID NO: 4 corresponds to the derived amino acid sequence of the *Crepis* sp. epoxygenase gene provided in SEQ ID NO: 3.

The nucleotide sequence set forth in SEQ ID NO: 5 corresponds to amplified DNA derived from *Vernonia galamensis* using amplification primers derived from a consensus sequence of mixed function monooxygenases, including the *Crepis* spp. epoxygenase gene sequences of the invention. The amplified DNA comprises a partial epoxygenase gene sequence, which includes nucleotide sequences capable of encoding the histidine-rich motif His-Arg-Asn-His-His which is characteristic of mixed function monooxygenase enzymes. The amino acid sequence set forth in SEQ ID NO: 6 corresponds to the derived amino acid sequence of the *Vernonia galamensis* epoxygenase gene provided in SEQ ID NO: 5.

The nucleotide sequence set forth in SEQ ID NO: 19 derived from *Vernonia galamensis* and encodes the full-length mixed function monooxygenase set forth in SEQ ID NO: 20.

The nucleotide sequence set forth in SEQ ID NO: 7 relates to the partial sequence of a *Crepis alpina* acetylenase gene which was used as a probe to isolate the nucleic acid comprising the nucleotide sequence set forth in SEQ ID NO: 1. The amino acid sequence set forth in SEQ ID NO: 8 corresponds to the derived amino acid sequence of said partial sequence of the *C. alpina* acetylenase gene.

As used herein, the term "acetylenase" shall be taken to refer to an enzyme which is capable of catalyzing the conversion of a carbon double bond in a fatty acid substrate molecule to a carbon triple bond or alternatively, which is capable of catalyzing the formation of a carbon triple bond in a fatty acid molecule.

The present invention clearly extends to the genomic gene equivalents of the cDNA molecules exemplified in any one of SEQ ID NOs: 1, 3, 5, or 19.

In a most particularly preferred embodiment, the present invention provides an isolated nucleic acid which comprises the nucleotide sequence set forth in any one of SEQ ID NOs: 1, 3, 5, or 19 or a genomic gene equivalent of said nucleotide sequence or a homologue, analogue or derivative thereof.

For the present purpose, "homologues" of a nucleotide sequence shall be taken to refer to an isolated nucleic acid which is substantially the same as the nucleic acid of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid which is substantially the same as a nucleic acid of the present invention or its complementary nucleotide sequence, notwithstanding the occurrence of any non-nucleotide constituents not normally present in said isolated nucleic acid, for example carbohydrates, radiochemicals including radionucleotides, reporter molecules such as, but not limited to DIG, alkaline phosphatase or horseradish peroxidase, amongst others.

"Derivatives" of a nucleotide sequence set forth herein shall be taken to refer to any isolated nucleic acid comprising significant sequence similarity to said sequence or a part thereof.

Generally, homologues, analogues or derivatives of the nucleic acid of the invention are produced by synthetic means or alternatively, derived from naturally-occurring sources. For example, the nucleotide sequence of the present invention may be subjected to mutagenesis to produce single or multiple nucleotide substitutions, deletions and/or insertions as indicated supra.

In one embodiment of the invention, preferred homologues, analogues or derivatives of the nucleotide sequences set forth in any one of SEQ ID NOs: 1, 3, 5, or 19 or complementary sequences thereto, encode immunologically-active or enzymatically-active polypeptides.

As used herein, the term "immunologically-active" shall be taken to refer to the ability of a polypeptide molecule to elicit an immune response in a mammal, in particular an immune response sufficient to produce an antibody molecule such as, but not limited to, an IgM or IgG molecule or whole serum containing said antibody molecule. The term "immunologically-active" also extends to the ability of a polypeptide to elicit a sufficient immune response for the production of monoclonal antibodies, synthetic Fab fragments of an antibody molecule, single-chain antibody molecule or other immunointeractive molecule.

As used herein, the term "enzymatically-active" shall be taken to refer to the ability of a polypeptide molecule to catalyze an enzyme reaction, in particular an enzyme reaction which comprises the epoxygenation of a carbon bond in a fatty acid substrate molecule. More particularly, whilst not limiting the invention, the term "enzymatically-active" may also refer to the ability of a polypeptide molecule to catalyze the epoxygenation of $\Delta$-9 or $\Delta$-12 in a fatty acid substrate molecule such as linoleic acid or vernolic acid.

In an alternative embodiment, a preferred homologue, analogue or derivative of the nucleotide sequence set forth in any one of SEQ ID NOs: 1 or 3 or 5 or 19, or a complementary sequence thereto, comprises a sequence of nucleotides which is at least 65% identical to at least 20 contiguous nucleotides therein, other than a nucleotide sequence which encodes a *Crepis* sp. acetylenase enzyme.

More preferably, the percentage identity to any one of SEQ ID NOs: 1 or 3 or 5 or 19 is at least about 85%. Even more preferably, a homologue, analogue or derivative of SEQ ID NOs: 1 or 3 or 5 or 19 is at least about 90% and even more preferably at least about 95% identical to at least 100 or 250 or 500 or 1000 contiguous nucleotides therein.

Reference herein to a percentage identity or percentage similarity between two or more nucleotide or amino acid sequences shall be taken to refer to the number of identical or similar residues in a nucleotide or amino acid sequence alignment, as determined using any standard algorithm known by those skilled in the art. In particular, nucleotide and/or amino acid sequence identities and similarities may be calculated using the Gap program, which utilizes the algorithm of Needleman and Wunsch (1970) to maximize the number of residue matches and minimize the number of sequence gaps. The Gap program is part of the Sequence and Analysis Software Package of the Computer Genetics Group Inc., University Research Park, Madison, Wis., United States of America (Devereux et al., 1984).

In a further alternative embodiment, a preferred homologue, analogue or derivative of the nucleotide sequence set forth in any one of SEQ ID NOs: 1, 3, 5, or 19 or a complementary sequence thereto, hybridizes under at least low stringency conditions to at least 20 contiguous nucleotides derived from said sequence.

More preferably, the stringency of hybridization is at least moderate stringency, even more preferably at least high stringency.

For the purposes of defining the level of stringency, those skilled in the art will be aware that several different hybridization conditions may be employed. For example, a low stringency may comprise a hybridization and/or a wash carried out in 6×SSC buffer, 0.1% (w/v) SDS at 28° C. A moderate stringency may comprise a hybridization and/or wash carried out in 2×SSC buffer, 0.1% (w/v) SDS at a temperature in the range 45° C. to 65° C. A high stringency may comprise a hybridization and/or wash carried out in 0.1×SSC buffer, 0.1% (w/v) SDS at a temperature of at least 65° C.

Generally, the stringency is increased by reducing the concentration of SSC buffer, and/or increasing the concentration of SDS in the hybridization buffer or wash buffer and/or increasing the temperature at which the hybridization and/or wash are performed. Conditions for a hybridization and/or wash are well understood by one normally skilled in the art. For the purposes of clarification of parameters affecting hybridization between nucleic acids, reference can conveniently be made to pages 2.10.8 to 2.10.16. of Ausubel et al. (1987), which is herein incorporated by reference.

The isolated nucleic acids disclosed herein may be used to isolate or identify homologues, analogues or derivatives thereof from other cells, tissues, or organ types, or from the cells, tissues, or organs of another species using any one of a number of means known to those skilled in the art.

For example, genomic DNA, or mRNA, or cDNA may be contacted, under at least low stringency hybridization conditions or equivalent, with a hybridization effective amount of an isolated nucleic acid which comprises the nucleotide sequence set forth in any one SEQ ID NOs: 1, 3, 5, or 19 or a complementary sequence thereto, or a functional part thereof, and the hybridization detected using a detection means.

The detection means may be a reporter molecule capable of giving an identifiable signal (e.g. a radioisotope such as $^{32}P$ or $^{35}S$ or a biotinylated molecule) covalently linked to the isolated nucleic acid of the invention.

In an alternative method, the detection means is any known format of the polymerase chain reaction (PCR). According to this method, degenerate pools of nucleic acid "primer molecules" of about 15-50 nucleotides in length are designed based upon the nucleotide sequences disclosed in SEQ ID NOs: 1, 3, 5, or 19 or a complementary sequence thereto. The homologues, analogues or derivatives (i.e. the "template molecule") are hybridized to two of said primer molecules, such that a first primer hybridizes to a region on one strand of the template molecule and a second primer hybridizes to a complementary sequence thereof, wherein the first and second primers are not hybridized within the same or overlapping regions of the template molecule and wherein each primer is positioned in a 5'- to 3'-orientation relative to the position at which the other primer is hybridized on the opposite strand. Specific nucleic acid copies of the template molecule are amplified enzymatically in a polymerase chain reaction, a technique that is well known to one skilled in the art.

The primer molecules may comprise any naturally-occurring nucleotide residue (i.e. adenine, cytidine, guanine, thymidine) and/or comprise inosine or functional analogues or derivatives thereof, capable of being incorporated into a polynucleotide molecule. The nucleic acid primer molecules may also be contained in an aqueous mixture of other nucleic acid primer molecules or be in a substantially pure form.

The detected sequence may be in a recombinant form, in a virus particle, bacteriophage particle, yeast cell, animal cell, or a plant cell. Preferably, the related genetic sequence originates from another plant species.

A third aspect of the present invention provides an isolated nucleic acid which encodes the amino acid sequence set forth in any one of SEQ ID NOs: 2 or 4 or 6 or 20 or a homologue, analogue or derivative thereof.

In one embodiment contemplated herein, preferred homologues, analogues or derivatives of the amino acid sequences set forth in SEQ ID NOs: 2, 4, 6, or 20 are immunologically-active or enzymatically-active polypeptides as defined supra.

In an alternative embodiment of the invention, preferred homologues, analogues or derivatives of the amino acid sequence set forth in any one of SEQ ID NOs: 2, 4, 6, or 20 comprise a sequence of amino acids which is at least 65% identical thereto, other than a *Crepis* sp. acetylenase polypeptide. More preferably, homologues, analogues or derivatives of SEQ ID NOs: 2 or 4 or 6 or 20 which are encompassed by the present invention are at least about 85% identical, even more preferably at least about 90% identical and still even more preferably at least about 95% identical, and still more preferably at least about 99%-100% identical thereto.

Homologues, analogues or derivatives of any one of SEQ ID NOs: 2 or 4 or 6 or 20 may further comprise a histidine-rich region as defined supra. Even more preferably, the subject epoxygenase at least comprises a sequence of amino acids which comprises three histidine rich regions as follows:

(i) His-Glu-Cys-Gly-His-His (SEQ ID NO: 15);
(ii) His-Arg-Asn-His-His (SEQ ID NO: 16); and
(iii) His-Val-Met-His-His (SEQ ID NO: 17) or His-Val-Leu-His-His (SEQ ID NO: 18), or a homologue, analogue or derivative thereof.

The invention described according to this alternative embodiment does not encompass the Δ12-desaturase enzymes derived from *Arabidopsis thaliana, Brassica juncea, Brassica napus* or *Glycine max*, amongst others.

The isolated nucleic acid of the present invention is useful for developing gene constructs comprising a sense molecule wherein said gene constructs are designed for the expression in a cell which does not normally express said nucleic acid or over-expression of said nucleic acid in a cell which does normally express the said nucleic acid.

Accordingly, a further aspect of the invention provides a gene construct which comprises a sense molecule which is operably connected to a promoter sequence.

The term "sense molecule" as used herein shall be taken to refer to an isolated nucleic acid which encodes or is complementary to an isolated nucleic acid which encodes a fatty acid epoxygenase wherein said nucleic acid is provided in a format suitable for its expression to produce a recombinant polypeptide when said sense molecule is introduced into a host cell by transfection or transformation.

Those skilled in the art will be aware that a gene construct may be used to "transfect" a cell, in which case it is introduced into said cell without integration into the cell's genome. Alternatively, a gene construct may be used to "transform" a cell, in which case it is stably integrated into the genome of said cell.

A sense molecule that comprises a fatty acid epoxygenase gene sequence or homologue, analogue or derivative thereof, may be introduced into a cell using any known method for the transfection or transformation of said cell. Wherein a cell is transformed by the gene construct of the invention, a whole organism may be regenerated from a single transformed cell, using any method known to those skilled in the art.

Thus, the epoxygenase genes described herein may be used to develop single cells or whole organisms which synthesize epoxy fatty acids not normally produced by wild or naturally-occurring organisms belonging to the same genera or species as the genera or species from which the transfected or transformed cell is derived, or to increase the levels of such fatty acids above the levels normally found in such wild or naturally-occurring organisms.

In an alternative preferred embodiment, the isolated nucleic acid of the invention is capable of reducing the level of epoxy fatty acids in a cell, when expressed therein, in the antisense orientation or as a ribozyme or co-suppression molecule, under the control of a suitable promoter sequence.

Co-suppression is the reduction in expression of an endogenous gene that occurs when one or more copies of said gene, or one or more copies of a substantially similar gene are introduced into the cell. The present invention also extends to the use of co-suppression to inhibit the expression of an epoxygenase gene as described herein.

In the context of the present invention, an antisense molecule is an RNA molecule which is transcribed from the complementary strand of a nuclear gene to that which is normally transcribed to produce a "sense" mRNA molecule capable of being translated into a polypeptide. The antisense molecule is therefore complementary to the sense mRNA, or a part thereof. Although not limiting the mode of action of the antisense molecules of the present invention to any specific mechanism, the antisense RNA molecule possesses the capacity to form a double-stranded mRNA by base pairing with the sense mRNA, which may prevent translation of the sense mRNA and subsequent synthesis of a polypeptide gene product.

Ribozymes are synthetic RNA molecules which comprise a hybridizing region complementary to two regions, each of at least 5 contiguous nucleotide bases in the target sense mRNA. In addition, ribozymes possess highly specific endoribonuclease activity, which autocatalytically cleaves the target sense mRNA. A complete description of the function of ribozymes is presented by Haseloff and Gerlach (1988) and contained in International Patent Application No. WO89/05852. The present invention extends to ribozymes which target a sense mRNA encoding an epoxygenase polypeptide described herein, thereby hybridizing to said sense mRNA and cleaving it, such that it is no longer capable of being translated to synthesize a functional polypeptide product.

According to this embodiment, the present invention provides a ribozyme or antisense molecule comprising a sequence of contiguous nucleotide bases which are able to form a hydrogen-bonded complex with a sense mRNA encoding an epoxygenase described herein, to reduce translation of said mRNA. Although the preferred antisense and/or ribozyme molecules hybridize to at least about 10 to 20 nucleotides of the target molecule, the present invention extends to molecules capable of hybridizing to at least about 50-100 nucleotide bases in length, or a molecule capable of hybridizing to a full-length or substantially full-length epoxygenase mRNA.

It is understood in the art that certain modifications, including nucleotide substitutions amongst others, may be made to the antisense and/or ribozyme molecules of the present invention, without destroying the efficacy of said molecules in inhibiting the expression of the epoxygenase gene. It is therefore within the scope of the present invention to include any nucleotide sequence variants, homologues, analogues, or fragments of the said gene encoding same, the only requirement being that said nucleotide sequence variant, when transcribed, produces an antisense and/or ribozyme molecule which is capable of hybridizing to the said sense mRNA molecule.

The present invention extends to gene constructs designed to facilitate expression of a sense molecule, an antisense molecule, ribozyme molecule, or co-suppression molecule which is capable of altering the level of epoxy fatty acids in a cell.

In a particularly preferred embodiment, the sense molecule, an antisense molecule, ribozyme molecule, co-suppression molecule, or gene targeting molecule which is capable of altering the epoxy fatty acid composition of a cell derived from plant or other organism comprises a sequence of nucleotides set forth in any one of SEQ ID NOs: 1, 3, 5, or 19 or a complementary strand, homologue, analogue or derivative thereof.

Those skilled in the art will also be aware that expression of a sense, antisense, ribozyme or co-suppression molecule may require the nucleic acid of the invention to be placed in operable connection with a promoter sequence. The choice of promoter for the present purpose may vary depending upon the level of expression of the sense molecule required and/or the species from which the host cell is derived and/or the tissue-specificity or development-specificity of expression of the sense molecule which is required.

Reference herein to a "promoter" is to be taken in its broadest context and includes the transcriptional regulatory sequences of a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. In the context of the present invention, the term "promoter" also includes the transcriptional regulatory sequences of a classical prokaryotic gene, in which case it may include a −35 box sequence and/or a −10 box transcriptional regulatory sequences.

In the present context, the term "promoter" is also used to describe a synthetic or fusion molecule, or derivative which confers, activates or enhances expression of said sense molecule in a cell. Preferred promoters may contain additional copies of one or more specific regulatory elements, to further enhance expression of the sense molecule and/or to alter the spatial expression and/or temporal expression of said sense molecule. For example, copper-responsive regulatory elements may be placed adjacent to a heterologous promoter sequence driving expression of a sense molecule to confer copper inducible expression thereon.

Placing a sense, antisense, ribozyme or co-suppression molecule under the regulatory control of a promoter sequence means positioning said molecule such that expression is controlled by the promoter sequence. A promoter is usually, but not necessarily, positioned upstream or 5' of a nucleic acid which it regulates. Furthermore, the regulatory elements comprising a promoter are usually positioned within 2 kb of the start site of transcription of the sense, antisense, ribozyme or co-suppression molecule or chimeric gene comprising same. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in gene constructs of the present invention include promoters derived from the genes of viruses, yeasts, moulds, bacteria, insects, birds, mammals and plants which are capable of functioning in isolated cells or whole organisms regenerated therefrom. The promoter may regulate the expression of the sense, antisense, ribozyme or co-suppression molecule constitutively, or differentially with respect to the tissue in which expression occurs or, with respect to the developmental stage at which expression occurs, or in response to external stimuli such as physiological stresses, pathogens, or metal ions, amongst others.

Examples of promoters include the CaMV 35S promoter, NOS promoter, octopine synthase (OCS) promoter, *Arabidopsis thaliana* SSU gene promoter, napin seed-specific promoter, $P_{32}$ promoter, BK5-T imm promoter, lac promoter, tac promoter, phage lambda $\lambda_L$ or $\lambda_R$ promoters, CMV promoter (U.S. Pat. No. 5,168,062), T7 promoter, lacUV5 promoter, SV40 early promoter (U.S. Pat. No. 5,118,627), SV40 late promoter (U.S. Pat. No. 5,118,627), adenovirus promoter, baculovirus P10 or polyhedrin promoter (U.S. Pat. Nos. 5,243,041, 5,242,687, 5,266,317, 4,745,051 and 5,169,784), and the like. In addition to the specific promoters identified herein, cellular promoters for so-called housekeeping genes are useful.

Preferred promoters according to this embodiment are those promoters which are capable of functioning in yeast, mould or plant cells. More preferably, promoters suitable for use according to this embodiment are capable of functioning in cells derived from oleaginous yeasts, oleaginous moulds or oilseed crop plants, such as flax sold under the trademark Linola™ (hereinafter referred to as "Linola™ flax"), sunflower, safflower, soybean, linseed, sesame, cottonseed, peanut, olive or oil palm, amongst others.

In a more preferred embodiment, the promoter may be derived from a genomic clone encoding an epoxygenase enzyme, preferably derived from the genomic gene equivalents of epoxygenase genes derived from *Chrysanthemum* spp., *Crepis* spp. including *C. palaestina* or other *Crepis* sp., *Euphorbia lagascae* or *Vernonia galamensis*, which are referred to herein.

In a more preferred embodiment, the promoter may be derived from a highly-expressed seed gene, such as the napin gene, amongst others.

The gene construct of the invention may further comprise a terminator sequence and be introduced into a suitable host cell where it is capable of being expressed to produce a recombinant polypeptide gene product or alternatively, a ribozyme or antisense molecule.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the gene constructs of the present invention include the nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit (SSU) gene terminator sequences, subclover stunt virus (SCSV) gene sequence terminators, any rho-independent *E. coli* terminator, amongst others.

Those skilled in the art will be aware of additional promoter sequences and terminator sequences which may be suitable for use in performing the invention. Such sequences may readily be used without any undue experimentation.

The gene constructs of the invention may further include an origin of replication sequence which is required for replication in a specific cell type, for example a bacterial cell, when said gene construct is required to be maintained as an episomal genetic element (e.g. plasmid or cosmid molecule) in said cell.

Preferred origins of replication include, but are not limited to, the f1-ori and co/E1 origins of replication.

The gene construct may further comprise a selectable marker gene or genes that are functional in a cell into which said gene construct is introduced.

As used herein, the term "selectable marker gene" includes any gene which confers a phenotype on a cell in which it is expressed to facilitate the identification and/or selection of cells which are transfected or transformed with a gene construct of the invention or a derivative thereof.

Suitable selectable marker genes contemplated herein include the ampicillin resistance (Amp$^r$), tetracycline resistance gene (Tc$^r$), bacterial kanamycin resistance gene (Kan$^r$), phosphinothricin resistance gene, neomycin phosphotransferase gene (nptII), hygromycin resistance gene, β-glucuronidase (GUS) gene, chloramphenicol acetyltransferase (CAT) gene and luciferase gene, amongst others.

A further aspect of the present invention provides a transfected or transformed cell, tissue, organ or whole organism which expresses a recombinant epoxygenase polypeptide or a ribozyme, antisense or co-suppression molecule as described herein, or a homologue, analogue or derivative thereof.

Preferably, the isolated nucleic acid is contained within a gene construct as described herein. The gene construct of the present invention may be introduced into a cell by various techniques known to those skilled in the art. The technique used may vary depending on the known successful techniques for that particular organism.

Means for introducing recombinant DNA into bacterial cells, yeast cells, or plant, insect, fungal (including mould), avian or mammalian tissue or cells include, but are not limited to, transformation using $CaCl_2$ and variations thereof, in particular the method described by Hanahan (1983), direct DNA uptake into protoplasts (Krens et al, 1982; Paszkowski et al, 1984), PEG-mediated uptake to protoplasts (Armstrong et al, 1990) microparticle bombardment, electroporation (Fromm et al., 1985), microinjection of DNA (Crossway et al., 1986), microparticle bombardment of tissue explants or cells (Christou et al, 1988; Sanford, 1988), vacuum-infiltration of tissue with nucleic acid, or in the case of plants, T-DNA-mediated transfer from *Agrobacterium* to the plant tissue as described essentially by An et al. (1985), Herrera-Estrella et al. (1983a, 1983b, 1985).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed.

Examples of microparticles suitable for use in such systems include 1 to 5 μm gold spheres. The DNA construct may be deposited on the microparticle by any suitable technique, such as by precipitation.

In a particularly preferred embodiment, wherein the gene construct comprises a "sense" molecule, it is particularly preferred that the recombinant epoxygenase polypeptide produced therefrom is enzymatically active.

Alternatively, wherein the cell is derived from a multicellular organism and where relevant technology is available, a whole organism may be regenerated from the transformed cell, in accordance with procedures well known in the art.

Those skilled in the art will also be aware of the methods for transforming, regenerating and propagating other type of cells, such as those of fungi.

In the case of plants, plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centers.

The term "embryogenesis", as used herein, means a process by which shoots and roots develop together in a concerted fashion (not sequentially), whether from somatic cells or gametes.

The regenerated transformed plants may be propagated by a variety of means, such as by clonal propagation or classical breeding techniques. For example, a first generation (or T1) transformed plant may be selfed to give homozygous second generation (or T2) transformant, and the T2 plants further propagated through classical breeding techniques.

The regenerated transformed organisms contemplated herein may take a variety of forms. For example, they may be chimeras of transformed cells and non-transformed cells; clonal transformants (e.g., all cells transformed to contain the expression cassette); grafts of transformed and untransformed tissues (e.g., in plants, a transformed root stock grafted to an untransformed scion).

A further aspect of the invention provides a method of altering the level of epoxy fatty acids in a cell, tissue, organ or organism, said method comprising expressing a sense, antisense, ribozyme or co-suppression molecule as described herein in said cell for a time and under conditions sufficient for the level of epoxy fatty acids therein to be increased or reduced.

In a preferred embodiment, the subject method comprises the additional first step of transforming the cell, tissue, organ or organism with the sense, antisense, ribozyme or co-suppression molecule.

As discussed supra the isolated nucleic acid may be contained within a gene construct.

According to this embodiment, the cell, organ, tissue or organism in which the subject sense, antisense, ribozyme or co-suppression molecule is expressed may be derived from a bacteria, yeast, fungus (including a mould), insect, plant, bird or mammal.

Because a recombinant epoxygenase polypeptide may be produced in the regenerated transformant as well as ex vivo, one alternative preferred embodiment of the present invention provides a method of producing a recombinant enzymatically active epoxygenase polypeptide in a cell, said method comprising the steps of:
 (i) producing a gene construct which comprises the cDNA or genomic epoxygenase genetic sequence of the invention placed operably under the control of a promoter capable of conferring expression on said genetic sequence in said cell, and optionally an expression enhancer element;
 (ii) transforming said gene construct into said cell; and
 (iii) selecting transformants which express the epoxygenase encoded by the genetic sequence at a high level.

A particularly preferred embodiment of the present invention provides a method of producing a recombinant enzymatically active epoxygenase polypeptide in a transgenic plant comprising the steps of:
 (i) producing a gene construct which comprises the cDNA or genomic epoxygenase genetic sequence of the invention placed operably under the control of a seed-specific promoter and optionally an expression enhancer element, wherein said genetic sequences is also placed upstream of a transcription terminator sequence;
 (ii) transforming said gene construct into a cell or tissue of said plant; and
 (iii) selecting transformants which express the epoxygenase encoded by the genetic sequence at a high level in seeds.

In a more particularly preferred embodiment, the plant is an oilseed species that normally produces significant levels of linoleic acid, for example Linola™ flax, oilseed rape, sunflower, safflower, soybean, linseed, sesame, cottonseed, peanut, olive or oil palm, amongst others.

In an even more particularly preferred embodiment, the plant is an oilseed species that normally produces significant levels of linoleic acid, for example Linola™ flax, sunflower or safflower, amongst others.

Enzymatically active recombinant epoxygenases described herein are particularly useful for the production of epoxy fatty acids from unsaturated fatty acid substrates. The present invention especially contemplates the production of specific epoxy fatty acids in cells or regenerated transformed organisms which do not normally produce that specific epoxy fatty acid.

Accordingly, a further aspect of the invention provides a method of producing an epoxy fatty acid in a cell, tissue, organ or organism, said method comprising incubating a cell, tissue, organ or organism which expresses an enzymatically active recombinant epoxygenase of the present invention with a fatty acid substrate molecule, preferably an unsaturated fatty acid substrate molecule, for a time and under conditions sufficient for at least one carbon bond of said substrate to be converted to an epoxy group.

In an alternative embodiment, the subject method further comprises the additional first step of transforming or transfecting the cell, tissue, organ or organism with a nucleic acid which encodes said recombinant epoxygenase or a homologue, analogue or derivative thereof, as herein before described. As discussed supra the isolated nucleic acid may be contained within a gene construct.

According to this embodiment, the cell, organ, tissue or organism in which the subject epoxygenase is expressed is derived from a bacteria, yeast, fungus (including a mould), insect, plant, bird or mammal. More preferably, the cell, organ, tissue or organism is derived from a yeast, plant or fungus, even more preferably from an oleaginous yeast or plant or fungus, or from an oilseed plant which does not normally express the recombinant epoxygenase of the invention.

Amongst the main economic oilseed plants contemplated herein, high-linoleic genotypes of flax, sunflower, corn and safflower are preferred targets. Soybean and rape seed are alternative targets but are less suitable for maximal epoxy fatty acid synthesis because of their lower levels of linoleic acid substrate and the presence of an active Δ15-desaturase competing with the epoxygenase for the linoleic acid substrate.

An alternative embodiment is the transformation of Linola™ (=low linolenic acid flax) with the epoxygenase of the invention. Linola™ flax normally contains around 70% linoleic acid with very little of this (<2%) being subsequently converted to linolenic acid by Δ15-desaturase (Green, 1986).

Preferred unsaturated fatty acid substrates contemplated herein include, but are not limited to, palmitoleic acid, oleic acid, linoleic acid, linolenic acid, and arachidonic acid, amongst others.

In plant species that naturally contain high levels of vernolic acid, the Δ12-epoxygenase therein may be very efficient at carrying out the epoxidation of linoleic acid. As a consequence, the present invention particularly contemplates the expression of recombinant Δ12-epoxygenase derived from *Euphorbia lagascae, Vernonia* spp. and *Crepis* spp. at high levels in transgenic oilseeds during seed oil synthesis, to produce high levels of vernolic acid therein.

Accordingly, linoleic acid is a particularly preferred substrate according to this embodiment of the invention. Additional substrates are not excluded.

The products of the substrate molecules listed supra will be readily determined by those skilled in the art, without undue experimentation. Particularly preferred epoxy fatty acids produced according to the present invention include 12,13-epoxy-9-octadecenoic acid (vernolic acid) and 12,13-epoxy-9,15-octadecadienoic acid, amongst others.

Conditions for the incubation of cells, organs, tissues or organisms expressing the recombinant epoxygenase in the presence of the substrate molecule will vary, at least depending upon the uptake of the substrate into the cell, tissue, organ or organism, and the affinity of the epoxygenase for the substrate molecule in the particular environment selected. Optimum conditions may be readily determined by those skilled in the relevant art.

The present invention clearly extends to the isolated oil containing epoxy fatty acids, and/or the isolated epoxy fatty acid itself produced as described herein and to any products derived therefrom, for example coatings, resins, glues, plastics, surfactants and lubricants, amongst others.

The inventors have shown further that the mixed function monooxygenases (MMO) which perform catalytic functions such as desaturation, acetylenation, hydroxylation and/or epoxygenation, form a family of genes sharing considerable nucleotide and amino acid sequence similarity. For example, the desaturase, acetylenase, hydroxylase and/or epoxygenase enzymes which act on substrate molecules having a similar chain length and position of any carbon double bond(s) (if present) are more closely related to each other than to enzymes acting upon other substrates, and may be considered to be a "family".

Without being bound by any theory or mode of action, the sequence similarity between the members of any gene family has its basis in the identity of the substrate involved and the biochemical similarity of the reaction events occurring at the target carbon bond during the modification reaction, suggesting that divergent sequences within a family may comprise catalytic determinants or at least a functional part thereof which contributes to the specific catalytic properties of the family members.

One example of a family is the desaturase, acetylenase, hydroxylase and/or epoxygenase enzymes which catalyze desaturation, acetylenation, hydroxylation and/or epoxygenation respectively, of the Δ12 position of linoleic acid (hereinafter referred to as the "C18 Δ12-MMO family"). The present inventors have compared the nucleotide and amino acid sequences of members of the C18 Δ12-MMO family to determine the divergent regions thereof which potentially comprise the determinants of alternative catalytic functions at the Δ12 position (hereinafter referred to as "putative catalytic determinants").

Furthermore, the presence of such families of fatty acid modifying MMOs is contemplated with respect to other fatty acid chain length and double bond positions. For example, the C18 Δ15-desaturase is contemplated to belong to a family of related enzymes capable of desaturation, acetylenation, hydroxylation and/or epoxidation of the Δ15 position in C18 fatty acid substrates, the C18 Δ15-MMO family.

By producing synthetic genes in which these catalytic determinants have been interchanged (referred to as "domain swapping") it is possible to convert genes encoding one catalytic function into those encoding alternative catalytic functions. For example, the Δ12 epoxygenase of the instant invention may be converted to a Δ12 acetylenase by replacing portions of its C-terminal and N-terminal sequences with the equivalent domains from the *Crepis alpina* Δ12 acetylenase. Similarly, the reverse domain swapping may also be performed.

As a further refinement, such changes in catalytic function can similarly be effected by making specific changes (e.g. addition, substitution or deletion) to only those amino-acids within each domain that are critical for determining the relevant catalytic function (such as by site-directed mutagenesis).

Accordingly, a further aspect of the present invention contemplates a synthetic fatty acid gene comprising a sequence of nucleotides derived from an epoxygenase gene as described herein, wherein said synthetic fatty acid gene encodes a polypeptide with epoxygenase or acetylenase or hydroxylase or desaturase activity, wherein said polypeptide either comprises an amino acid sequence which differs from a naturally-occurring epoxygenase or acetylenase or hydroxylase or desaturase enzyme, or said polypeptide exhibits catalytic properties which are different from a naturally-occurring epoxygenase or acetylenase or hydroxylase or desaturase enzyme or said polypeptide comprises a sequence of amino acids which are at least about 60% identical to a part of SEQ ID NO: 2 or 4 or 6 or 20 or homologue, analogue or derivative of said part.

Preferably, the synthetic fatty acid gene of the invention is derived from a Δ12 epoxygenase gene.

In one embodiment, the synthetic fatty acid gene of the invention encodes a fusion polypeptide in which the N-terminal and/or C-terminal amino acids of any one of SEQ ID NOs: 2 or 4 or 6 or 20 are replaced, in-frame, by amino acid sequences of a different member of the same family.

In a particularly preferred embodiment, the N-terminal and/or C-terminal amino acids of SEQ ID NO: 2 or 4 or 6 or 20 are replaced by the corresponding regions of the acetylenase, desaturase or hydroxylase polypeptides set forth in FIG. 2. More preferably, at least about 30 amino acid residues from the N-terminal and/or C-terminal regions of any one of SEQ ID NOs: 2 or 4 or 6 or 20 are replaced, in-frame, by the corresponding regions of the acetylenase, desaturase or hydroxylase polypeptides set forth in FIG. 2.

In an alternative embodiment, the synthetic fatty acid gene of the invention encodes a fusion polypeptide in which the N-terminal and/or C-terminal amino acids of a fatty acid acetylenase or fatty acid hydroxylase or fatty acid desaturase are replaced, in-frame, by the N-terminal and/or C-terminal region of any one of SEQ ID NOs: 2 or 4 or 6 or 20.

In a particularly preferred embodiment, the N-terminal and/or C-terminal amino acids of a fatty acid acetylenase or fatty acid hydroxylase or fatty acid desaturase are replaced, in-frame, by the N-terminal and/or C-terminal region of any one of SEQ ID NOs: 2 or 4 or 6 or 20. Even more preferably, the fatty acid acetylenase or fatty acid hydroxylase or fatty acid desaturase is selected from the list set forth in FIG. 2.

Even still more preferably, at least about 30 amino acid residues from the N-terminal and/or C-terminal regions of a fatty acid acetylenase or fatty acid hydroxylase or fatty acid desaturase are replaced, in-frame, by the N-terminal and/or C-terminal region of any one of SEQ ID NOs: 2 or 4 or 6 or 20.

Accordingly, the present invention extends to any variants of the epoxygenase enzymes referred to herein, wherein said variants are derived from an epoxygenase polypeptide as described herein and exhibit demonstrable acetylenase or hydroxylase or desaturase activity, and either comprises an amino acid sequence which differs from a naturally-occurring acetylenase or hydroxylase or desaturase enzyme, or exhibit catalytic properties which are different from a naturally-occurring acetylenase or hydroxylase or desaturase enzyme, or comprise a sequence of amino acids which are at least about 60% identical to any one of SEQ ID NOs: 2 or 4 or 6 or 20.

As with other aspects of the invention, the variants described herein may be produced as recombinant polypeptides or in transgenic organisms, once the subject synthetic genes are introduced into a suitable host cell and expressed therein.

The recombinant polypeptides described herein or a homologue, analogue or derivative thereof, may also be immunologically active molecules.

A further aspect of the present invention provides an immunologically-interactive molecule which is capable of binding to a recombinant epoxygenase polypeptide of the invention.

Preferably, the recombinant epoxygenase polypeptide to which the immunologically-interactive molecule is capable of binding comprises a sequence of amino acids set forth in any one of SEQ ID NOs: 2, 4, 6, or 20, or a homologue, analogue or derivative thereof.

In one embodiment, the immunologically interactive molecule is an antibody molecule. The antibody molecule may be monoclonal or polyclonal. Monoclonal or polyclonal antibodies may be selected from naturally occurring antibodies to an epitope, or peptide fragment, or synthetic epoxygenase peptide derived from a recombinant gene product or may be specifically raised against a recombinant epoxygenase or a homologue, analogue or derivative thereof.

Both polyclonal and monoclonal antibodies are obtainable by immunization with an appropriate gene product, or epitope, or peptide fragment of a gene product. Alternatively, fragments of antibodies may be used, such as Fab fragments. The present invention extends to recombinant and synthetic antibodies and to antibody hybrids. A "synthetic antibody" is considered herein to include fragments and hybrids of antibodies The antibodies contemplated herein may be used for identifying genetic sequences which express related epoxygenase polypeptides encompassed by the embodiments described herein.

The only requirement for successful detection of a related epoxygenase genetic sequence is that said genetic sequence is expressed to produce at least one epitope recognized by the antibody molecule. Preferably, for the purpose of obtaining expression to facilitate detection, the related genetic sequence is placed operably behind a promoter sequence, for example the bacterial lac promoter. According to this preferred embodiment, the antibodies are employed to detect the presence of a plasmid or bacteriophage which expresses the related epoxygenase. Accordingly, the antibody molecules are also useful in purifying the plasmid or bacteriophage which expresses the related epoxygenase.

The subject antibody molecules may also be employed to purify the recombinant epoxygenase of the invention or a naturally-occurring equivalent or a homologue, analogue or derivative of same.

Example 1

Characterization of Epoxy Fatty Acids in *Euphorbia lagascae* and *Crepis* spp.

Seed from the wild species *Euphorbia lagascae* and from various *Crepis* species were screened by gas liquid chromatography for the presence of epoxy fatty acids. As shown in Table 3, *Euphorbia lagascae* contains very high levels of the epoxy fatty acid vernolic acid in its seed oil. Seeds from *Crepis palaestina* were shown to contain 61.4 weight % of vernolic acid and 0.71 weight % of the acetylenic fatty acid crepenynic acid of total fatty acids (Table 3).

TABLE 3

Fatty acid composition of lipids derived from seeds of *Crepis alpina*, *Crepis palaestina* and *Euphorbia lagascae*

| Fatty acid | Relative distribution (weight %)[a] | | |
|---|---|---|---|
| | *Crepis alpina* | *Crepis palaestina* | *Euphorbia* |
| Palmitic | 3.9 | 5.1 | 4.3 |
| Stearic | 1.3 | 2.3 | 1.8 |
| Oleic | 1.8 | 6.3 | 22.0 |
| Linoleic | 14.0 | 23.0 | 10.0 |
| Crepyninic | 75.0 | 0.7 | 0 |
| Vernolic | 0 | 61.4 | 58.0 |
| Other | 4.0 | 1.2 | 3.9 |

[a]Calculated from the area % of total integrated peak areas in gas liquid chromatographic determination of methyl ester derivatives of the seed lipids Example 2

Biochemical Characterization of Linoleate Δ12-epoxygenases in *Euphorbia lagascae* and *Crepis palaestina*

The enzyme, linoleate Δ12-epoxygenase synthesizes vernolic acid from linoleic acid. Linoleate Δ12-epoxygenases derived from *Euphorbia lagascae* and *Crepis palaestina* are localized in the microsome. The enzymes from these species at least can remain active in membrane (microsome) fractions prepared from developing seeds.

Preparations of membranes from *Euphorbia lagascae* and assays of their epoxygenase activities were performed as described by Bafor et al. (1993) with incubations containing NADPH, unless otherwise indicated in Table 4. Lipid extraction, separation and methylation as well as GLC and radio-GLC separations were performed essentially as described by Kohn et al. (1994) and Bafor et al. (1993).

Preparations of membranes from *Crepis alpina* and *Crepis palaestina* were obtained as follows. *Crepis alpina* and *Crepis palaestina* plants were grown in green houses and seeds were harvested at the mid-stage of development (17-20 days after flowering). Cotyledons were squeezed out from their seed coats and homogenized with mortar and pestle in 0.1M phosphate buffer, pH 7.2 containing 0.33M sucrose, 4 mM NADH, 2 mM CoASH, 1 mg of bovine serum albumin/ml and 4,000 units of catalase/ml. The homogenate was centrifuged for 10 min at 18,000×g and the resulting supernatant centrifuged for 60 min at 150,000×g to obtain a microsome pellet.

Standard desaturase, acetylenase and epoxygenase assays with microsomal membranes from *Crepis* species were performed at 25° C. with microsomal preparations equivalent to 0.2 mg microsomal protein resuspended in fresh homogenization buffer and 10 nmol of either $[1-^{14}C]18:1$-CoA or $[1-^{14}C]18:2$-CoA (specific activity 85,000 d.p.m./nmol) in a total volume of 360 μl. When NADPH was used as coreductant, the membranes were resuspended in homogenization buffer comprising NADPH in place of NADH.

Biochemical characterization of the microsomal linoleate Δ12-epoxygenase derived from *Euphorbia lagascae* and *Crepis palaestina* was carried out and data obtained were compared to the biochemical characteristics of oleate Δ12-desaturase and linoleate Δ12-acetylenase enzymes derived from microsomal preparations of *Crepis alpina* (Table 4).

As shown in Table 4, the *Crepis palaestina* linoleate Δ12-epoxygenase exhibits similar biochemical features to the linoleate Δ12-acetylenase and oleate Δ12-desaturase from *Crepis alpina*, in so far as all three enzymes require $O_2$, work equally well with either NADH or NADPH as the coreductants, and are inhibited by cyanide but not by carbon monoxide. Additionally, none of these enzymes are inhibited by monoclonal antibodies against cytochrome P450 reductase.

The data in Table 4 suggest that the *Crepis palaestina* linoleate Δ12-epoxygenase belongs to the same class of enzyme as the *Crepis alpina* microsomal oleate Δ12-desaturase and linoleate Δ12-acetylenase.

In contrast, the *Euphorbia lagascae* linoleate Δ12-epoxygenase requires NADPH as the coreductant, is not inhibited by cyanide, but is inhibited by carbon monoxide (Table 4). Additionally, the inventors have discovered that the *Euphorbia lagascae* linoleate Δ12-epoxygenase is inhibited by monoclonal antibodies raised against a cytochrome P450 reductase enzyme. These data suggest that the *Euphorbia lagascae* linoleate Δ12-epoxygenase belongs to the cytochrome P450 class of proteins and is therefore not related biochemically to the *Crepis palaestina* linoleate Δ12-epoxygenase.

constructed using the ZAP-cDNA Gigapack cloning kit (Stratagene).

Single-stranded cDNA was prepared from RNA derived from the developing seeds of *Crepis alpina*, using standard procedures. A PCR fragment, designated as D12V (SEQ ID NO: 7), was obtained by amplifying the single-stranded cDNA using primers derived from the deduced amino acid sequences of plant mixed-function monooxygenases.

The D12V fragment was subsequently random-labeled and used to screen the *Crepis palaestina* cDNA library supra on Hybond $N^+$ membrane filters from Amersham as prescribed by the manufacturer using standard hybridization conditions. This approach resulted in the purification of a recombinant bacteriophage, designated Cpa12.

The nucleotide sequence of the Cpa12 cDNA was determined and is set forth in SEQ ID NO: 1.

The Cpa12 cDNA appeared to be full-length. A schematic representation of an expression vector comprising the Cpa12 cDNA is presented in FIG. 1. The gene construct set forth therein is designed for introduction into plant material for the production of a transgenic plant which expresses the subject epoxygenase. Those skilled in the art will recognise that similar expression vectors may be produced, without undue experimentation, and used for the production of transgenic plants which express any of the genetic sequences of the instant invention, by replacing the Cpa12 cDNA with another structural gene sequence.

As shown in FIG. 2, the nucleotide sequence of the Crep1 cDNA encoded a polypeptide which was closely related at the

TABLE 4

Comparison of the biochemical characteristics of epoxygenases, acetylenases and desaturases derived from *Crepis* spp. and *Euphorbia lagascae*

| | Enzyme Activity (% of control) | | | |
| --- | --- | --- | --- | --- |
| Treatment | C. alpina oleate Δ12-desaturase | C. alpina linoleate Δ12-acetylenase | C. palaestina linoleate Δ12-epoxygenase | E. lagascae linoleate Δ12-epoxygenase |
| Carbon monoxide | 85 | 84 | 88 | 3 |
| Anti-P450 reductase antibodies ($C_5A_5$) | 96 | 91 | 94 | 33 |
| KCN | 16 | 0 | 35 | 92 |
| minus NADH plus NADPH | 95 | 73 | 94 | 100 (control) |
| minus NADPH plus NADH | 100 (control) | 100 (control) | 100 (control) | 11 |

Example 3

Strategy for Cloning *Crepis palaestina* Epoxygenase Genes

Cloning of the *Crepis palaestina* epoxygenase genes relied on the characteristics of the *C. palaestina* and *C. alpina* enzymes described in the preceding Examples.

In particular, poly (A)+RNA was isolated from developing seeds of *Crepis palaestina* using a QuickPrep Micro mRNA purification kit (Pharmacia Biotechnology) and used to synthesize an oligosaccharide d(T)-primed double stranded cDNA. The double stranded cDNA was ligated to EcoRI/NotI adaptors (Pharmacia Biotechnology) and a cDNA library was amino acid level, at least, to an acetylenase enzyme of *C. alpina* (Bafor et al. 1997; International Patent Application No. PCT/SE97/00247).

The 1.4 kb insert from pCpa12 was sequenced (SEQ ID NO. 1) and shown to comprise an open reading frame which encodes a polypeptide of 374 amino acids in length. The deduced amino acid sequence of Cpa12 showed 81% identity and 92% similarity to the Δ12-acetylenase from *Crepis alpina* and approximately 60% identity and 80% similarity with plant microsomal Δ12-desaturase proteins (FIG. 2). However, the polypeptide encoded by Cpa12 comprised significant differences in amino acid sequence compared to non-epoxygenase enzymes. In particular, the Cpa12 has a deletion of six contiguous amino acids in the 5'-terminal region compared to all the microsomal Δ12 desaturases, and a deletion of two contiguous amino acids in the 3'-terminal region compared to the Crep1 Δ12 acetylenase (FIG. 2).

Although membrane-bound fatty acid desaturase genes show limited sequence homologies, they all contain three regions of conserved histidine-rich motifs as follows:

(i) His-Xaa$_{3-4}$-His (SEQ ID NO: 21 and SEQ ID NO: 22);
(ii) His-Xaa$_{2-3}$-His-His (SEQ ID NO: 23 and SEQ ID NO: 24); and
(iii) His-(Xaa)$_{2-3}$-His-His (SEQ ID NO: 23 and SEQ ID NO: 24), wherein His designates histidine, Xaa designates any naturally-occurring amino acid residue as set forth in Table 1 herein, the integer (Xaa)$_{3-4}$ refers to a sequence of amino acids comprising three or four repeats of Xaa, and the integer (Xaa)$_{2-3}$ refers to a sequence of amino acids comprising two or three repeats of Xaa. These histidine-rich regions are suggested to be a part of the active center of the enzyme (Shanklin et al., 1994).

The amino acid sequence encoded by the Cpal2 cDNA comprises three histidine-rich motifs similar, but not identical, to the histidine-rich motifs of the Δ12-desaturase enzymes. These data suggest that the Cpal2 cDNA encodes an enzyme which belongs to the mixed function monooxygenase class of enzymes.

Figure 3:
FIG. 3 is a copy of a photographic representation of a northern blot hybridization showing seed-specific expression of the *Crepis palaestina* epoxygenase gene exemplified by SEQ ID NO: 1. Northern blot analysis of total RNA from leaves (lane 1) and developing seeds (lane 2) of *Crepis palaestina*. 15 µg of total RNA was run on a Northern gel and blotted onto Hybond N+ membrane from Amersham according to the manufacturer's instructions. The blot was hybridized at 60° C. with a probe made from the 3' untranslated region of SEQ ID NO: 1. The blot was washed twice in 2×SSC (NaCl— Sodium Citrate buffer) at room temperature for 10 minutes, then in 0.1×SSC at 60° C. for 20 min.

The analysis of fatty acids presented in Example 1 supra indicated that vernolic acid was at least present in the seeds of *Crepis palaestina*. This enzyme may in fact be present exclusively in the seeds of *C. palaestina*. The expression of the Cpal2 gene was examined using the 3' untranslated region of the Cpal2 cDNA clone as a hybridization probe on northern blots of mRNA derived from developing seeds and leaves of *C. palaestina*. As shown in FIG. 3, the Cpal2 gene was highly expressed in developing seeds but no expression could be detected in leaves. These data are consistent with the enzyme activity profile of *C. palaestina* linoleate Δ12-epoxygenase in these tissues.

Example 4

Demonstration of Epoxygenase Activity for the *C. palaestina* Clones

Confirmation that the cDNA clones of *C. palaestina* encode an epoxygenase was obtained by transforming *Arabidopsis thaliana*, with each individual candidate clone. The transformed tissue was examined for the presence of epoxy fatty acids that *A. thaliana* would not otherwise produce. Additionally, the level of hydroxy fatty acids was determined, as such fatty acids can be formed from the metabolism of an epoxy fatty acid, by the action of endogenous *A. thaliana* epoxide hydrolases (Blee and Schuber, 1990).

Figure 4:
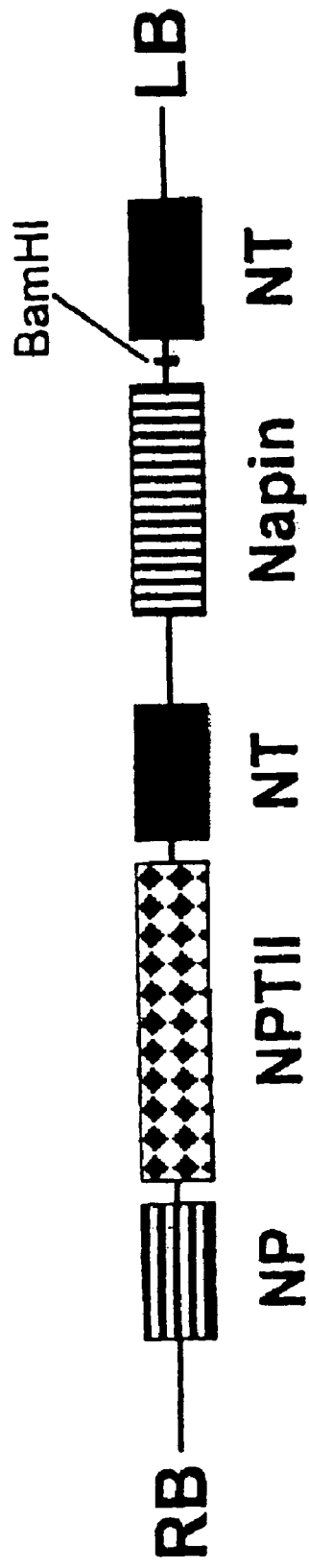
FIG. 4 is a schematic representation of a binary plasmid vector containing an expression cassette comprising the truncated napin seed-specific promoter (Napin) and nopaline synthase terminator (NT), with a BamHI cloning site there between, in addition to the kanamycin-resistance gene NPTII operably connected to the nopaline synthase promoter (NP) and nopaline synthase terminator (NT) sequences. The expression cassette is flanked by T-DNA left border (LB) and right-border (RB) sequences.

The epoxygenase cDNA comprising SEQ ID NO: 1 was cloned into the Binary vector construct set forth in FIG. 4. Briefly, the cDNA sequence was sub-cloned from the pCpal2 plasmid (FIG. 1) into the binary plasmid, by digesting pCpal2 with EcoRI and end-filling the restriction fragment using T4 DNA polymerase enzyme. The Binary vector (FIG. 4) was made linear using BamHI and also end-filled using T4 DNA polymerase. For the end-filling reactions, 1 μg of cDNA insert or linearized Binary vector DNA was resuspended in 50 μl of T4 DNA polymerase buffer (33 mM Tris-acetate pH 7.9, 66 mM potassium acetate, 10 mM magnesium acetate and 5 mM DDT) supplemented with 100 mM of each dNTP and 0.1 mg/ml BSA and 3 units of T4 DNA polymerase, and incubated for 6 min incubation at 37° C. The reaction was stopped by heating at 75° C. for 10 mins. The blunt-ended cDNA and Binary vector DNA were ligated using T4 DNA ligase and standard ligation conditions as recommended by Promega. Clones were selected in which the SEQ ID NO: 1 sequence was inserted behind the napin promoter, in the sense orientation, thereby allowing for expression of the epoxygenase polypeptide. The Binary plasmid harboring SEQ ID NO: 1, in the sense orientation, operably under control of the truncated napin promoter, is represented schematically in FIG. 5.

Figure 5:
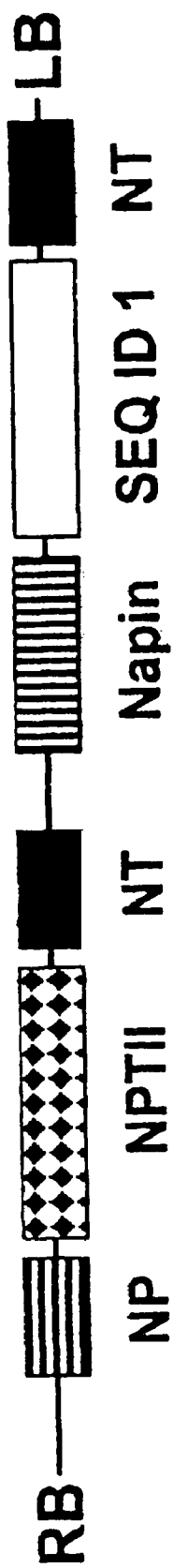
FIG. 5 is a schematic representation of a binary plasmid vector containing an expression cassette which comprises SEQ ID NO: 1 placed operably under the control of a truncated napin seed-specific promoter (Napin) and upstream of the nopaline synthase terminator (NT), in addition to the kanamycin-resistance gene NPTII operably connected to the nopaline synthase promoter (NP) and nopaline synthase terminator (NT) sequences. The expression cassette is flanked by T-DNA left border (LB) and right-border (RB) sequences. To produce this construct, SEQ ID NO: 1 is inserted into the BamHI site of the binary vector set forth in FIG. 4.

The Binary plasmid set forth in FIG. 5 was transformed into *Agrobacterium* strain AGLI using electroporation and used to transform *Arabidopsis thaliana*. Transgenic *A. thaliana* plants were obtained according to the method described by Valvekens et al. (1988) and Dolferus et al. (1994).

Figure 6A:
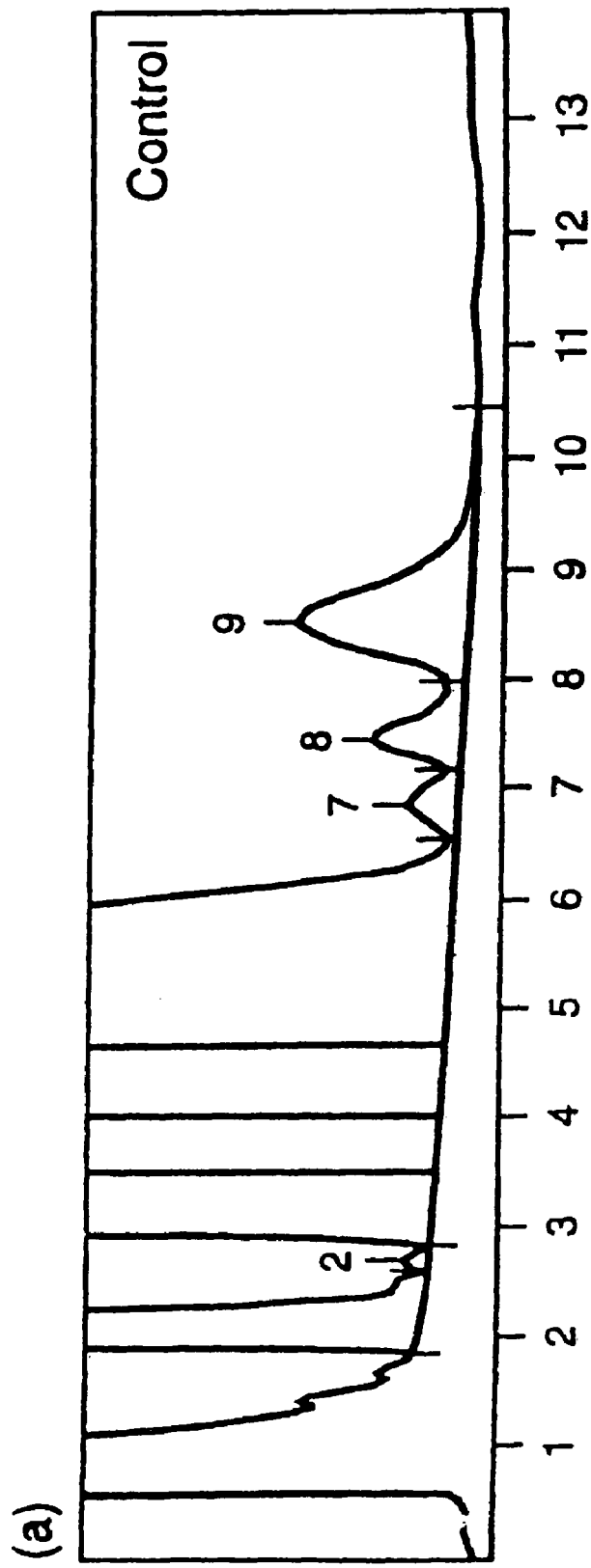
FIG. 6 is a graphical representation of gas-chromatography traces of fatty acid methyl esters prepared from oil seeds of untransformed *Arabidopsis thaliana* plants [panel (a)], or *A. thaliana* plants (transgenic line Cpal-17) which have been transformed with SEQ ID NO: 1 using the gene construct set forth in FIG. 5 [panels (b) and (c)]. In panels (a) and (b), fatty acid methyl esters were separated using packed column separation. In panel (c), the fatty acid methyl esters were separated using capillary column separation. The elution positions of vernolic acid are indicated.
Figure 6B:
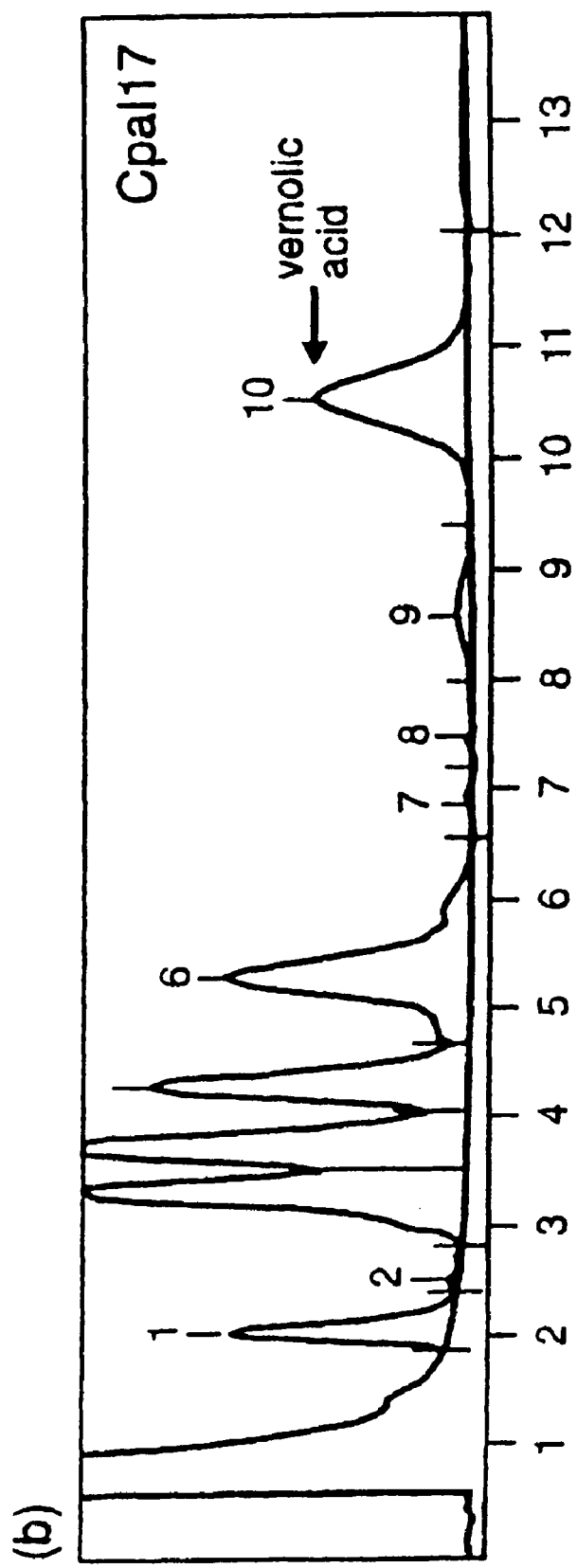
Figure 6C:
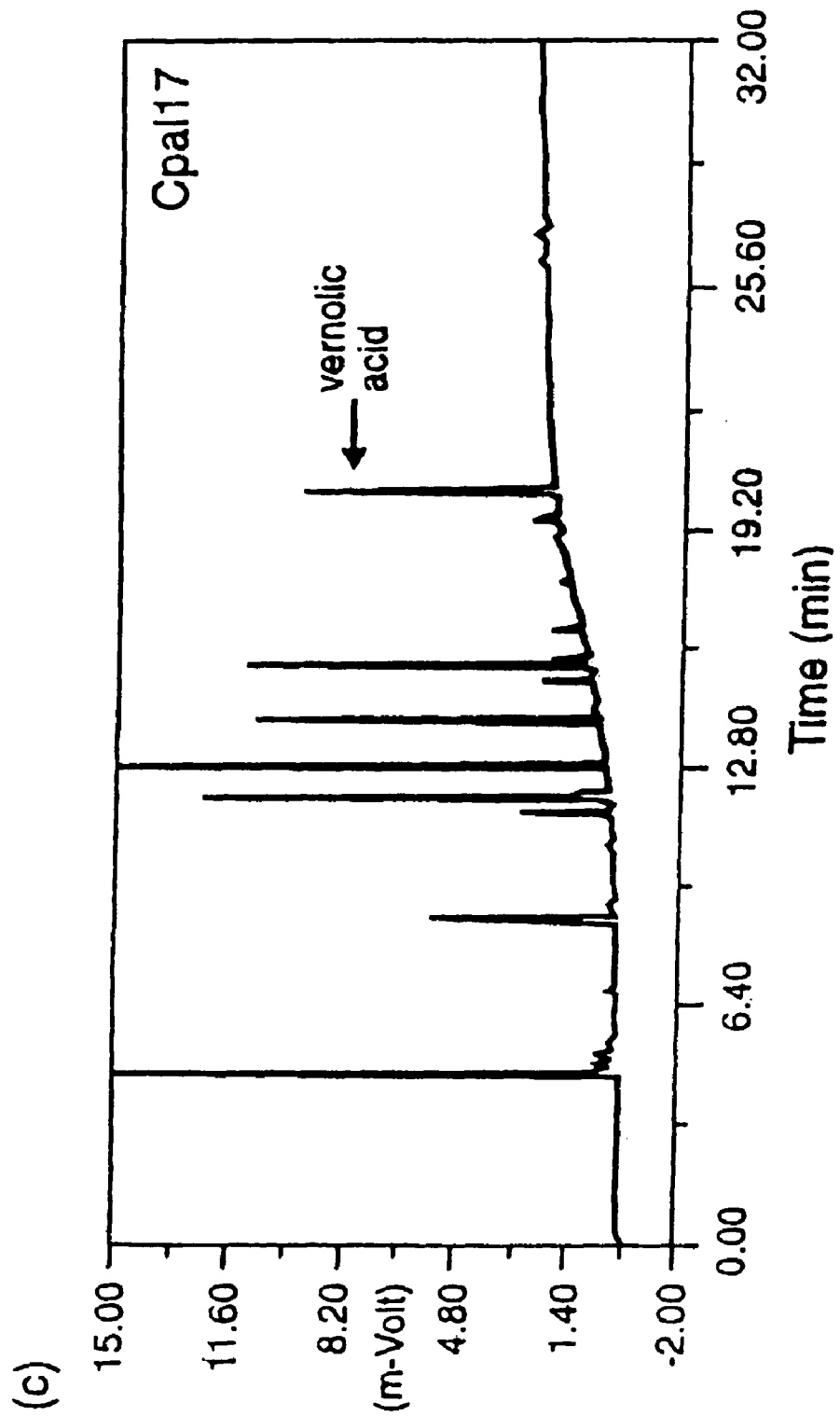

Transgenic plants and untransformed (i.e. control) plants were grown to maturity. Mature seed of each plant was analyzed for fatty acid composition by standard techniques. Primary transformant (T$_0$) plants were established and T1 seed was harvested from each plant and analyzed for fatty acid composition by gas chromatography. Twelve T$_0$ plants were shown to contain vernolic acid in their T1 seed lipids at concentrations ranging from 0.9% to 15.8% of total fatty acids, while untransformed control plants contained no vernolic acid (Table 5). The highest-expressing plant line was Cpal-17, for which the GLC elution profiles (from packed column and capillary column analysis) is presented in FIG. 6. The GLC elution profile from packed column for the untransformed control is also shown in FIG. 6.

TABLE 5

Vernolic acid levels in transgenic *A. thaliana* lines expressing SEQ ID NO: 1

| T$_0$ Plant No. | Vernolic acid (weight % of total seed fatty acids) |
|---|---|
| Cpal-4 | 1.4 |
| Cpal-5 | 1.1 |
| Cpal-8 | 2.7 |
| Cpal-9 | 0.9 |
| Cpal-13 | 0.9 |
| Cpal-15 | 1.1 |
| Cpal-17 | 15.8 |
| Cpal-21 | 1.3 |
| Cpal-23 | 1.4 |
| Cpal-24 | 1.0 |
| Cpal-25 | 1.2 |
| Cpal-26 | 1.1 |
| untransformed control line | 0.0 |

Alternatively, or in addition, putative fatty acid epoxygenase sequences described herein are each transformed into *Linum usitatissimum* (flax) and *Arabidopsis thaliana* under the control of the napin seed-specific promoter. Transgenic flax and *Arabidopsis thaliana* plants are examined for presence of epoxy fatty acids in developing seed oils. Previous work has shown that if epoxy fatty acids are fed to developing flax embryos they are incorporated into triglycerides (Example 10).

Alternatively, yeast are also transformed with the epoxygenase clones of the invention and assayed for production of epoxy fatty acids.

Example 6

Mass Spectroscopy Confirmation of Epoxy Fatty Acids in $T_1$ Arabidopsis Seed Borne on Primary $T_0$ Transgenic Plants Gas chromatography of methyl esters prepared from seed lipids of T1 seed of Cpal2-transformed *Arabidopsis thaliana* plants (Example 5) revealed the presence of two additional fatty acids compared to the untransformed controls. The first of these compounds had a retention time equivalent to that of a vernolic acid standard. The second compound had a longer retention time and was putatively identified as 12,13-epoxy-9,15-octadecadienoic acid, an expected derivative of vernolic acid, resulting from desaturation at the Δ15 position by the endogenous *Arabidopsis thaliana* Δ15-desaturase.

Confirmation of the exact identity of the two peaks was obtained by mass spectroscopy of diols which were prepared from the epoxy fatty acid fraction derived from Cpal2-transformed plants. The diols were converted further to trimethylsilyl ethers and analyzed by GC-MS DB23 on a fused silica capillary column (Hewlett-Packard 5890 II GC coupled to a Hewlett Packard 5989A MS working in electron impact at 70 eV15). The total ion chromatogram showed two peaks as follows:

(i) The first eluting peak had prominent ions of mass 73, 172, 275, and 299, indicating that the epoxy group was positioned at C-12 of a C18 fatty acid and that a double bond occurred between the epoxy group and the carboxyl terminus. This mass spectra was identical to the spectra of a trimethylsilyl ether derivative of diols prepared from pure vernolic acid (12,13-epoxy-9-octadecenoic acid); and (ii) the second eluting peak had prominent ions of mass 73, 171, 273, and 299, indicating the presence of two double bonds and an epoxy group positioned at C-12 of a C18 fatty acid, consistent with the mass spectrum for 12,13-epoxy-9,15-octadecadienoic acid.

Example 7

Fatty Acid Analysis of Cpal2 Transgenic *Arabidopsis* Plants

The T1 seed derived from transformed *Arabidopsis thaliana* plants expressing the Cpal2 cDNA clone under control of the napin promoter was germinated and T1 plants were established from five $T_0$ lines (Nos. 4, 8, 13, 17 & 21 in Table 5). The T2 seed was harvested from each T1 plant and analyzed for fatty acid composition. The progeny of transformant Nos. 4, 8, 13 and 21 (Table 5) segregated as expected for presence of vernolic acid, with those plants containing vernolic acid ranging up to 3.1% (Table 6).

Figure 7:
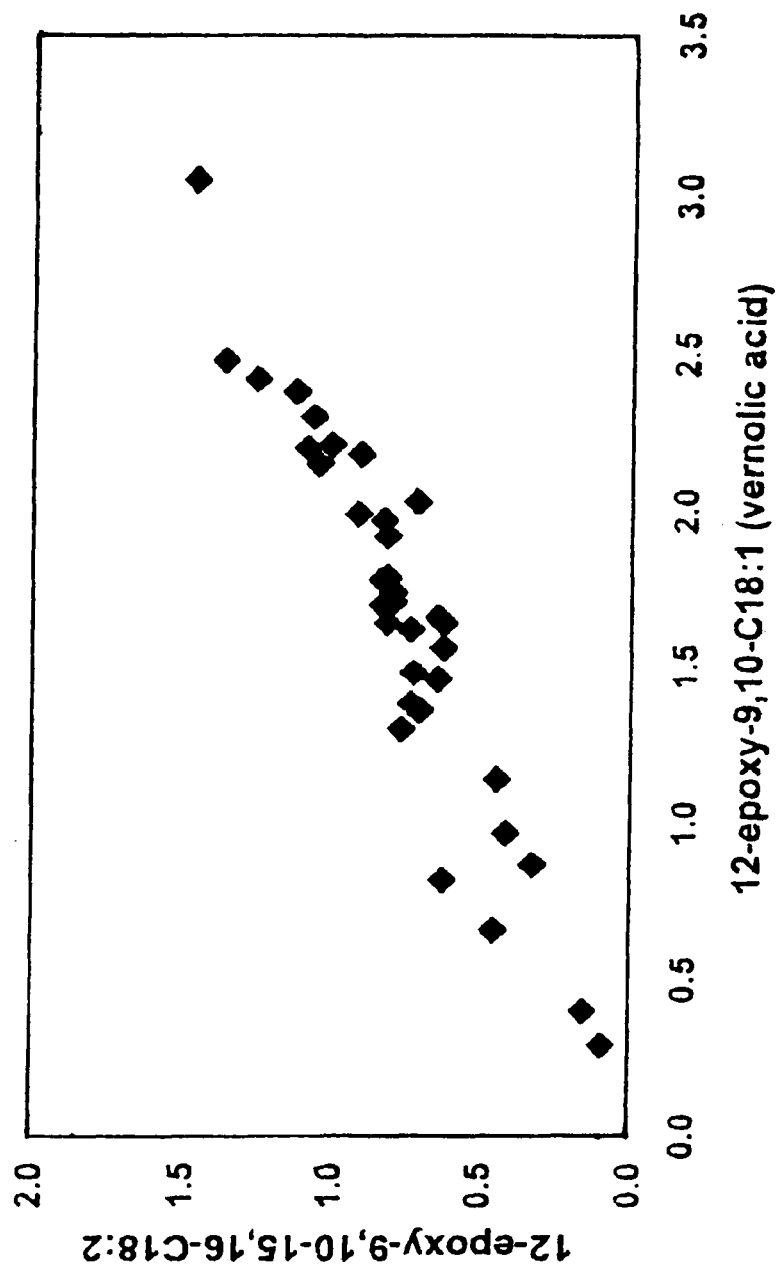
FIG. 7 is a graphical representation showing the joint distribution of epoxy fatty acids in selfed seed on $T_1$ plants of Cpal2-transformed *Arabidopsis thaliana* plants as determined using gas chromatography. Levels of both vernolic acid (x-axis) and 12,13-epoxy-9,15-octadecadienoic acid (y-axis) were determined and plotted relative to each other. Data show a positive correlation between the levels of these fatty acids in transgenic plants.

All T1 plants that contained vernolic acid (i.e. epoxy 18:1 in Table 6) also contained 12,13-epoxy-9,15-octadecadienoic acid (i.e. epoxy 18:2 in Table 6; see also FIG. 7), indicating that some of the vernolic acid synthesized by the Cpal2 epoxygenase was subsequently desaturated by the endogenous Δ15-desaturase.

TABLE 6

Fatty acid composition of selfed seeds borne on $T_1$ plants derived from five primary Cpal2 transformants of *Arabidopsis thaliana*

| | Fatty Acid | | | | | | | | | | |
|---|---|---|---|---|---|---|---|---|---|---|---|
| Plant | Non-epoxy fatty acids | | | | | | | | | Epoxy fatty acids | |
| No. | 16:0 | 18:0 | 18:1 | 18:2 | 18:3 | 20:0 | 20:1 | 22:0 | 22:1 | 18:1 | 18:2 |
| 4-1 | 8.3 | 3.9 | 15.5 | 23.9 | 20.6 | 2.8 | 16.5 | 1.7 | 1.6 | — | — |
| 4-2 | 7.6 | 4.1 | 20.3 | 17.8 | 18.0 | 3.4 | 19.7 | 1.8 | 2.0 | 0.82 | 0.63 |
| 4-3 | 8.4 | 4.3 | 26.0 | 13.5 | 16.1 | 2.8 | 19.0 | 1.8 | 1.6 | 2.03 | 0.72 |
| 4-4 | 7.6 | 4.0 | 25.2 | 14.3 | 16.0 | 2.8 | 19.8 | 2.1 | 1.7 | 1.99 | 0.92 |
| 4-5 | 7.2 | 3.6 | 15.6 | 23.1 | 19.9 | 3.1 | 19.7 | 1.6 | 2.1 | — | — |
| 4-6 | 7.0 | 3.7 | 19.2 | 17.8 | 18.4 | 3.2 | 20.3 | 1.9 | 2.1 | 0.87 | 0.33 |
| 4-8 | 7.4 | 3.9 | 16.0 | 23.6 | 20.1 | 3.1 | 18.7 | 1.6 | 1.8 | — | — |
| 4-9 | 7.6 | 4.0 | 24.8 | 13.4 | 15.9 | 2.8 | 20.4 | 2.3 | 1.8 | 2.30 | 1.07 |
| 4-10 | 7.6 | 4.2 | 24.0 | 13.5 | 16.2 | 3.1 | 20.4 | 1.9 | 1.8 | 1.97 | 0.83 |
| 4-11 | 7.4 | 3.9 | 15.0 | 23.2 | 20.4 | 3.3 | 18.8 | 1.7 | 2.0 | — | — |
| 4-12 | 8.7 | 4.0 | 20.7 | 17.0 | 17.5 | 2.6 | 17.2 | 1.7 | 1.5 | 1.38 | 0.74 |
| 4-13 | 7.2 | 4.1 | 21.9 | 16.4 | 17.7 | 3.2 | 21.0 | 1.7 | 1.9 | 1.14 | 0.45 |
| 8-1 | 8.1 | 3.9 | 26.1 | 15.0 | 16.0 | 2.6 | 19.5 | 2.0 | 1.6 | 1.79 | 0.82 |
| 8-3 | 8.7 | 4.2 | 31.6 | 11.5 | 14.0 | 2.2 | 18.5 | 1.9 | 1.4 | 2.38 | 1.13 |
| 8-4 | 8.5 | 4.1 | 27.2 | 15.1 | 16.1 | 2.5 | 18.9 | 1.8 | 1.4 | 1.70 | 0.84 |
| 8-5 | 9.1 | 4.2 | 27.7 | 14.7 | 16.2 | 2.4 | 18.3 | 1.7 | 1.5 | 1.70 | 0.82 |
| 8-6 | 9.8 | 4.0 | 26.0 | 17.2 | 17.2 | 2.3 | 16.9 | 1.6 | 1.2 | 1.36 | 0.71 |
| 8-7 | 10.0 | 3.5 | 15.2 | 25.3 | 22.3 | 2.3 | 14.4 | 1.7 | 1.7 | — | — |
| 8-8 | 8.4 | 4.3 | 32.2 | 10.7 | 13.3 | 2.5 | 20.3 | 1.6 | 1.5 | 1.92 | 0.82 |
| 8-9 | 9.8 | 3.6 | 15.9 | 25.3 | 22.0 | 2.4 | 14.5 | 1.6 | 1.3 | — | — |
| 8-10 | 7.5 | 3.9 | 24.4 | 15.9 | 15.8 | 2.8 | 20.2 | 2.2 | 1.8 | 1.70 | 0.82 |
| 8-11 | 7.6 | 3.8 | 15.4 | 23.6 | 19.8 | 2.9 | 19.4 | 1.5 | 1.8 | — | — |
| 8-12 | 9.4 | 3.7 | 24.2 | 16.7 | 16.7 | 2.2 | 17.6 | 0.9 | 1.2 | 1.46 | 0.65 |
| 8-13 | 10.3 | 4.3 | 25.3 | 17.1 | 17.9 | 2.2 | 16.0 | 1.8 | 1.3 | 1.48 | 0.73 |
| 13-1 | 7.0 | 4.3 | 33.3 | 8.1 | 11.1 | 2.7 | 23.1 | 1.7 | 1.6 | 2.42 | 1.26 |
| 13-2 | 7.2 | 4.3 | 30.4 | 9.6 | 12.7 | 2.8 | 22.0 | 1.8 | 1.6 | 2.48 | 1.37 |
| 13-3 | 7.6 | 3.9 | 15.6 | 23.6 | 19.7 | 3.0 | 19.1 | 1.7 | 1.8 | — | — |
| 13-4 | 7.7 | 4.0 | 15.2 | 22.5 | 19.3 | 3.1 | 18.0 | 1.6 | 1.7 | — | — |
| 13-5 | 8.0 | 4.2 | 16.3 | 22.2 | 17.5 | 4.4 | 19.4 | 2.0 | 2.0 | — | — |

TABLE 6-continued

Fatty acid composition of selfed seeds borne on $T_1$ plants derived from five primary Cpal2 transformants of *Arabidopsis thaliana*

| Plant | Fatty Acid | | | | | | | | | | |
|---|---|---|---|---|---|---|---|---|---|---|---|
| | Non-epoxy fatty acids | | | | | | | | | Epoxy fatty acids | |
| No. | 16:0 | 18:0 | 18:1 | 18:2 | 18:3 | 20:0 | 20:1 | 22:0 | 22:1 | 18:1 | 18:2 |
| 13-6 | 7.9 | 4.4 | 25.7 | 14.7 | 15.8 | 2.9 | 21.2 | 1.6 | 1.7 | 1.56 | 0.63 |
| 13-7 | 7.9 | 4.0 | 16.0 | 23.3 | 19.6 | 3.0 | 19.1 | 1.6 | 1.8 | — | — |
| 13-9 | 8.0 | 4.0 | 16.1 | 23.6 | 20.0 | 2.9 | 18.7 | 1.6 | 1.6 | — | — |
| 13-10 | 8.7 | 4.2 | 34.6 | 9.6 | 12.5 | 2.2 | 19.1 | 1.5 | 1.2 | 2.21 | 1.01 |
| 13-11 | 8.7 | 4.0 | 17.6 | 24.3 | 18.9 | 2.8 | 17.1 | 1.6 | 1.4 | — | — |
| 13-12 | 8.9 | 4.2 | 26.4 | 14.6 | 16.0 | 2.5 | 17.5 | 1.6 | 1.2 | 1.62 | 0.74 |
| 13-13 | 9.0 | 4.4 | 27.9 | 14.4 | 15.3 | 2.5 | 18.9 | 1.5 | 1.4 | 1.30 | 0.77 |
| 13-14 | 9.2 | 4.2 | 17.2 | 23.8 | 18.8 | 2.7 | 17.9 | 1.7 | 1.5 | — | — |
| 13-15 | 8.4 | 4.2 | 19.7 | 20.9 | 18.6 | 2.7 | 17.7 | 1.4 | 1.5 | 0.40 | 0.16 |
| 13-16 | 8.2 | 4.3 | 23.0 | 17.1 | 17.3 | 2.8 | 19.3 | 1.5 | 1.5 | 0.97 | 0.42 |
| 13-17 | 8.3 | 4.1 | 15.7 | 23.9 | 19.9 | 2.8 | 17.6 | 1.6 | 1.9 | — | — |
| 17-1 | 7.6 | 4.1 | 15.8 | 23.7 | 19.6 | 2.6 | 20.3 | 1.7 | 1.7 | — | — |
| 17-2 | 8.3 | 4.1 | 16.4 | 24.4 | 20.1 | 2.3 | 16.8 | 1.5 | 1.4 | — | — |
| 17-3 | 8.1 | 4.1 | 16.4 | 24.3 | 20.0 | 2.5 | 17.6 | 1.6 | 1.4 | — | — |
| 21-1 | 8.1 | 4.3 | 26.9 | 14.5 | 15.0 | 2.9 | 19.9 | 1.5 | 1.5 | 1.64 | 0.63 |
| 21-2 | 8.2 | 4.0 | 27.9 | 11.8 | 13.2 | 2.5 | 19.8 | 1.7 | 1.5 | 2.18 | 0.91 |
| 21-3 | 8.8 | 3.7 | 16.4 | 24.4 | 20.6 | 2.5 | 17.3 | 1.7 | 1.4 | — | — |
| 21-4 | 7.9 | 3.9 | 19.6 | 19.8 | 17.8 | 2.7 | 18.7 | 1.7 | 1.7 | 0.66 | 0.46 |
| 21-5 | 7.2 | 4.2 | 26.5 | 12.9 | 14.4 | 3.0 | 21.5 | 0.9 | 1.8 | 1.78 | 0.84 |
| 21-6 | 8.3 | 4.2 | 27.4 | 13.9 | 15.4 | 2.6 | 19.9 | 1.7 | 1.5 | 1.66 | 0.65 |
| 21-7 | 7.2 | 4.2 | 26.8 | 13.5 | 13.4 | 3.0 | 21.9 | 1.7 | 1.8 | 1.74 | 0.80 |
| 21-8 | 7.4 | 3.8 | 16.3 | 23.6 | 19.4 | 3.2 | 19.2 | 1.7 | 1.9 | — | — |
| 21-9 | 7.2 | 4.0 | 28.1 | 11.8 | 13.5 | 3.0 | 22.5 | 1.9 | 1.9 | 2.15 | 1.05 |
| 21-10 | 7.2 | 4.2 | 26.1 | 13.8 | 14.6 | 3.0 | 22.3 | 1.7 | 1.8 | 1.64 | 0.82 |
| 21-11 | 7.1 | 4.2 | 29.2 | 11.5 | 12.7 | 3.0 | 22.5 | 1.8 | 1.8 | 2.20 | 1.09 |
| 21-12 | 7.2 | 4.1 | 26.2 | 13.6 | 14.2 | 3.1 | 22.4 | 1.8 | 1.9 | 1.71 | 0.80 |
| 21-13 | 7.1 | 4.3 | 33.7 | 7.1 | 10.0 | 2.7 | 24.1 | 2.0 | 1.8 | 3.05 | 1.47 |
| 21-14 | 7.4 | 3.7 | 16.9 | 21.9 | 19.6 | 3.1 | 19.2 | 1.8 | 2.0 | 0.29 | tr |
| 21-15 | 7.7 | 3.6 | 15.6 | 24.3 | 20.2 | 2.9 | 18.1 | 1.8 | 1.8 | — | — |

Example 8

Fatty Acid Analysis of Cpal2 Transgenic Linola Plants

The binary plasmid construct described above comprising the Cpal2 cDNA clone (FIG. 5) was transformed into *Agrobacterium tumefaciens* strain AGL1, using electroporation. The transformed *A. tumefaciens* was used to infect *Linum usitatissimum* var. Eyre explants as described by Lawrence et al (1989), except that MS media was used as the basal medium for the induction of roots on regenerated shoot material.

Two primary Linola transformants ($T_0$ plants) designated AP20 and AP21 were confirmed as being transgenic by PCR using primers directed against the Cpal2 gene and by showing that these plants were kanamycin resistant. Ten T1 seeds from each plant were analyzed individually for fatty acid composition using standard techniques.

As shown in Table 7, seed from AP20 segregated into 3 classes, comprised of three seeds with no vernolic acid, two having greater than 0.7% vernolic acid, and five having intermediate levels (0.13-0.47%) of vernolic acid.

Similarly, seeds from AP21 segregated into 3 classes comprised of five seeds having no vernolic acid, two having greater than 0.25% vernolic acid and three having an intermediate level (0.09-0.14%) of vernolic acid (Table 8).

Thus, a total of twelve seeds were obtained which contained vernolic acid. Eight of the twelve AP20 and AP21 seeds containing vernolic acid also contained 12,13-epoxy-9,15-octadecadienoic acid.

TABLE 7

Fatty acid composition of 10 individual T1 seeds from Linola Cpal2 primary transformant AP20

| $T_1$ | Non-epoxy fatty acids | | | | | | | | | Epoxy fatty acids | |
|---|---|---|---|---|---|---|---|---|---|---|---|
| seed | 16:0 | 18:0 | 18:1 | 18:2 | 18:3 | 20:0 | 20:1 | 22:0 | 22:1 | 18:1 | 18:2 |
| 1 | 6.4 | 3.6 | 17.8 | 68.1 | 2.0 | 0.2 | — | 0.6 | — | — | — |
| 2 | 6.0 | 3.5 | 25.4 | 60.8 | 1.4 | 0.2 | 0.2 | — | — | 0.70 | 0.23 |
| 3 | 6.0 | 3.9 | 20.4 | 64.6 | 2.1 | 0.3 | 0.6 | — | — | — | — |
| 4 | 6.3 | 3.5 | 28.3 | 57.3 | 1.3 | 0.2 | 0.2 | 1.4 | — | 0.34 | 0.28 |
| 5 | 5.2 | 4.8 | 24.9 | 61.2 | 1.6 | 0.3 | 0.2 | 0.1 | — | 0.37 | — |
| 6 | 5.8 | 4.1 | 23.3 | 63.1 | 1.9 | 0.2 | 0.2 | 0.2 | — | 0.47 | — |
| 7 | 5.9 | 4.3 | 21.7 | 64.1 | 2.2 | 0.2 | 0.2 | 0.2 | — | 0.13 | 0.12 |

TABLE 7-continued

Fatty acid composition of 10 individual T1 seeds from Linola Cpal2 primary transformant AP20

| T1 seed | Non-epoxy fatty acids | | | | | | | | | Epoxy fatty acids | |
|---|---|---|---|---|---|---|---|---|---|---|---|
| | 16:0 | 18:0 | 18:1 | 18:2 | 18:3 | 20:0 | 20:1 | 22:0 | 22:1 | 18:1 | 18:2 |
| 8 | 5.9 | 3.3 | 22.3 | 65.2 | 2.0 | 0.2 | 0.2 | 0.1 | 0.2 | — | — |
| 9 | 5.6 | 4.0 | 25.2 | 61.4 | 1.7 | 0.2 | 0.2 | 0.1 | — | 0.84 | — |
| 10 | 6.2 | 4.4 | 27.4 | 57.9 | 1.7 | 0.2 | 0.2 | 0.2 | — | 0.54 | — |

TABLE 8

Fatty acid composition of 10 individual T1 seeds from Linola Cpal2 primary transformant AP21

| T1 seed | Non-epoxy fatty acids | | | | | | | | | Epoxy fatty acids | |
|---|---|---|---|---|---|---|---|---|---|---|---|
| | 16:0 | 18:0 | 18:1 | 18:2 | 18:3 | 20:0 | 20:1 | 22:0 | 22:1 | 18:1 | 18:2 |
| 1 | 6.1 | 4.2 | 35.2 | 50.8 | 1.3 | — | — | — | 2.0 | — | — |
| 2 | 5.7 | 5.0 | 32.9 | 53.3 | 1.4 | 0.2 | 0.2 | 0.2 | — | 0.14 | 0.21 |
| 3 | 5.9 | 4.0 | 35.1 | 50.8 | 1.3 | 0.2 | 0.2 | 0.1 | 1.5 | — | — |
| 4 | 7.5 | 4.1 | 38.8 | 45.5 | 1.2 | 0.2 | 0.3 | — | 1.7 | — | — |
| 5 | 5.8 | 5.0 | 28.8 | 57.3 | 1.3 | 0.2 | 0.2 | 0.1 | — | 0.37 | 0.06 |
| 6 | 5.8 | 5.0 | 44.1 | 41.4 | 1.4 | 0.2 | 0.2 | 0.2 | — | — | — |
| 7 | 6.5 | 4.5 | 27.9 | 58.6 | 1.3 | 0.2 | 0.1 | 0.1 | — | — | — |
| 8 | 6.9 | 4.6 | 37.6 | 48.1 | 1.2 | — | — | — | — | 0.10 | 0.19 |
| 9 | 6.2 | 4.7 | 33.7 | 52.1 | 1.3 | 0.2 | 0.2 | 0.2 | — | 0.09 | 0.07 |
| 10 | 6.1 | 4.8 | 29.7 | 56.6 | 1.3 | 0.2 | 0.2 | 0.1 | — | 0.25 | 0.04 |

Four T1 plants were established from the kanamycin-resistant seedlings of AP20. All four plants were subsequently shown to produce vernolic acid in their T2 seed (Table 9). Levels of 18:2 epoxy fatty acids were not analyzed in these T2 seed.

TABLE 9

Fatty acid composition of T2 seeds from Linola Cpal2 T1 progeny of AP20

| T2 seed | Non-epoxy fatty acids | | | | | | | | | epoxy fatty acid |
|---|---|---|---|---|---|---|---|---|---|---|
| | 16:0 | 18:0 | 18:1 | 18:2 | 18:3 | 20:0 | 20:1 | 22:0 | 22:1 | 18:1 |
| A | 3.4 | 3.0 | 27.4 | 65.5 | 0.6 | na | na | na | na | 0.06 |
| B | 3.5 | 3.1 | 30.2 | 62.6 | 0.6 | na | na | na | na | 0.07 |
| C | 3.6 | 2.7 | 33.3 | 59.8 | 0.6 | na | na | na | na | 0.07 |
| D | 3.4 | 3.1 | 28.2 | 64.6 | 0.6 | na | na | na | na | 0.11 | na. = not analyzed

Example 9

Producing Epoxy Fatty Acids in Transgenic Organisms

Production of an oil rich in vernolic acid was achieved by transforming the epoxygenase gene described herein, in particular SEQ ID NO: 1, into *Arabidopsis thaliana*, as described in the preceding Examples. As shown in Table 5, transgenic *A. thaliana* lines expressing SEQ ID NO: 1 produce high levels of vernolic acid in their seeds relative to other fatty acids. In particular, in one transgenic line (Cpal-17), the vernolic acid produced is as much as 15.2% (w/w) of total seed fatty acid content.

Production of an oil rich in vernolic acid is also achieved by transforming the epoxygenase gene described herein, in any one of SEQ ID NOs: 1, 3, 5, or 19 and preferably any one of SEQ ID NOs:1 or 3 or 5 or 19, into any oil accumulating organism that normally has very high levels of linoleic acid and minimal other competing enzyme activities capable of utilizing linoleic acid as a substrate. The genetic sequences of the invention are placed operably under the control of a promoter which produces high-level expression in oilseed, for example the napin seed-specific promoter.

In one alternative approach to the transformation of *A. thaliana*, high-linoleic genotypes of flax, sunflower, corn or safflower are transformed with the epoxygenase of the invention. High levels of vernolic acid are produced by the transgenic plants during seed oil synthesis, when the epoxygenase gene is expressed at high levels.

Alternatively, Linola™ (=low linolenic acid) flax is transformed with the epoxygenase of the invention. High levels of vernolic acid are produced by the transgenic Linola™ flax plants during seed oil synthesis, when the epoxygenase gene is expressed at high levels.

Additionally, the inventors have shown that labeled vernolic acid fed to developing flax seeds is not degraded but is incorporated into storage lipids at all three positions of the triglyceride molecule (see Example 10). Consistent with these data, high levels of vernolic acid synthesized by the introduced epoxygenase are readily deposited into the seed oil triglycerides of this species.

Example 10

Incorporation of Oleic Acid and Vernolic Acid into the Lipids of Developing Linseed Cotyledons Detached developing linseed cotyledons (six pairs in each incubation, duplicate incubations) at mid stage of seed development (20 days after flowering) were incubated with 10 nmol of the ammonium salts of either [1-$^{14}$C]vernolic acid (specific activity 3000 d.p.m./nmol) or [1-$^{14}$C]oleic acid (specific activity 5000 d.p.m./nmol) in 0.2 ml phosphate buffer pH 7.2 for 30 min at 30° C. The cotyledons were then rinsed three times with 1 ml of distilled water and either extracted immediately in an Ultra Turrax according to Bligh and Dyer (1959) or incubated further in 0.5 m. 0.1 M phosphate buffer pH 7.2 for 90 or 270 min before extraction. An aliquot of the lipids in the chloroform phase was methylated and separated on silica gel TLC plates in n-hexane/diethylether/acetic acid (85:15:1). The rest of the lipids in the chloroform phase of each sample were applied on two separate silica gel TLC plates and the plates were developed in chloroform/methanol/acetic acid/water (85:15:10:3.5 by vol) for polar lipids separation and in n-hexane/diethylether/acetic acid (60:40:1.5) for neutral lipid separation. Lipid areas with migration corresponding to authentic standards were removed and radioactivity in each lipid were quantified by liquid scintillation counting.

Figure 8:
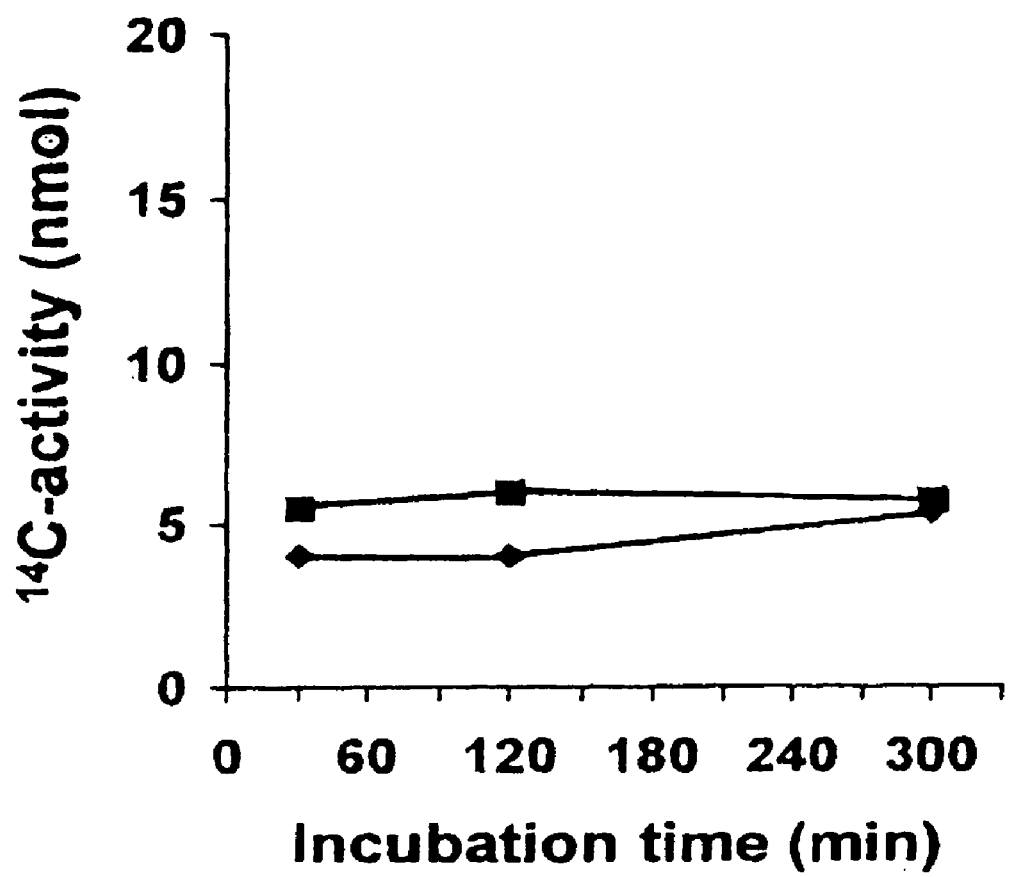
FIG. 8 is a graphical representation showing the incorporation of $^{14}C$-label into the chloroform phase obtained from lipid extraction of linseed cotyledons during labeled-substrate feeding. Symbols used; ♦, [$^{14}C$] oleic acid feeding; ■, [$^{14}C$] vernolic acid feeding.

The recovery of $^{14}$C-label in the chloroform phase is depicted in FIG. 8. Somewhat more than half of added radioactivity from both [$^{14}$C]oleic acid and [$^{14}$C]vernolic acid was taken up by the cotyledons and recovered as lipophilic substances after the 30 min pulse labeling. This quantity remained virtually unchanged during the further 270 min of incubation with both substrates. Separation of radioactive methyl esters of the lipids showed that most of the radioactivity (92%) from [$^{14}$C]vernolic acid feeding experiments resided in compounds with the same migration as methylvernoleate indicating that the epoxy group remained intact in the linseed cotyledons throughout the 270 min incubation.

Figure 9:
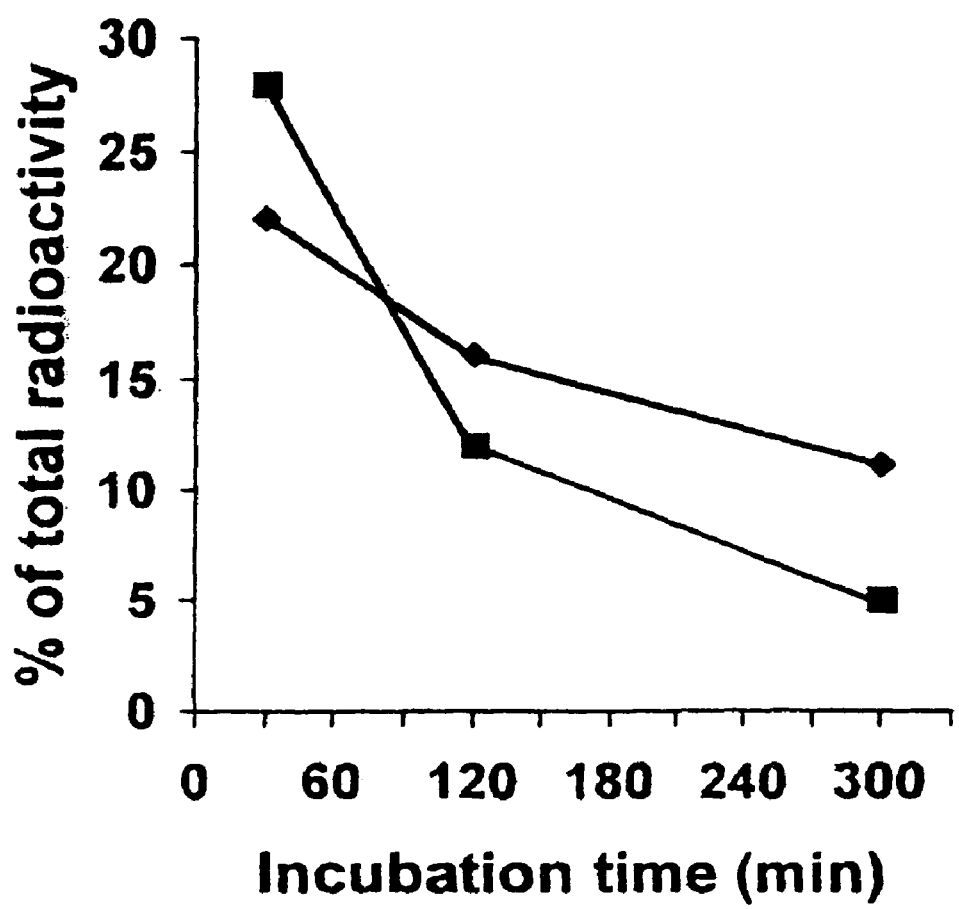
FIG. 9 is a graphical representation showing the incorporation of $^{14}C$-label into the phosphatidyl choline of linseed cotyledons during labeled-substrate feeding. Symbols used; ♦, [$^{14}C$] oleic acid feeding; ■, [$^{14}C$] vernolic acid feeding.

About 28% of the activity from [$^{14}$C]vernolic acid feeding which was present in the chloroform phase resided in phosphatidylcholine after 30 min and the radioactivity decreased to only 5% at 300 min of incubation (FIG. 9).

About 22% of the activity from [$^{14}$C]oleic acid feeding which was present in the chloroform phase resided in phosphatidylcholine after 30 min and the radioactivity decreased to about 11% at 300 min of incubation (FIG. 9).

Figure 10:
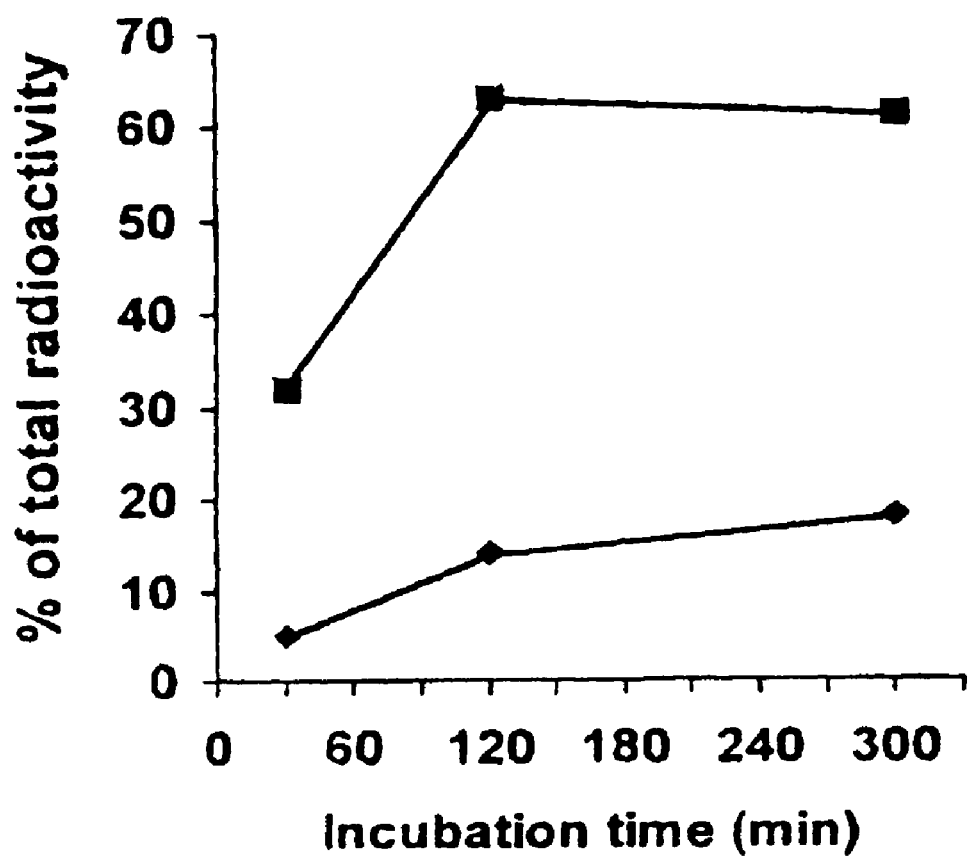
FIG. 10 is a graphical representation showing the incorporation of $^{14}C$-label into the triacylglycerols of linseed cotyledons during labeled-substrate feeding. Symbols used ♦, [$^{14}C$] oleic acid feeding; ■, [$^{14}C$] vernolic acid feeding.

About 32% of the activity from [$^{14}$C]vernolic acid feeding which was present in the chloroform phase resided in triacylglycerols after 30 min and the radioactivity increased to over 60% at 300 min of incubation (FIG. 10). The diacylglycerols contained some 24% of the activity in the [14C] vernolic acid feeding experiments and this quantity remained rather constant over the incubation periods.

About 5% of the activity from [$^{14}$C]oleic acid feeding which was present in the chloroform phase resided in triacylglycerols after 30 min and the radioactivity increased to 18% at 300 min of incubation (FIG. 10). The diacylglycerols contained some 19% of the activity after 30 min in the [$^{14}$C] oleic acid feeding experiments and this quantity remained rather constant over the incubation periods.

The above experiment shows that linseed cotyledons do not metabolize the epoxy group of vernolic acid to any great extent. Further it shows that linseed cotyledons possess mechanisms to efficiently remove vernolic acid from membrane lipids and incorporate them into triacylglycerols.

Example 11

Cloning of Δ12-epoxygenase Genes from an Unidentified *Crepis* Species

Homologues of the Cpal2 Δ12-epoxygenase gene were obtained from species other than *C. palaestina* which are rich in epoxy fatty acids, by cloning the members of the gene family of Δ12 mixed function monooxygenases that are highly expressed in developing seeds and comparing their amino acid sequence to those of known Δ12-desaturase and Δ12-epoxygenase sequences.

Such genes were cloned either by screening developing seed cDNA libraries with genetic probes based on either the Cpal2 gene (SEQ ID NO: 1) or the D12V fragment (SEQ ID NO: 7), or by amplifying PCR fragments using primers designed against conserved sequences of the plant Δ12 mixed function monooxygenases, as described herein. Putative Δ12-epoxygenase sequences show greater overall sequence identity to the Δ12-epoxygenase sequences disclosed herein, than to the known Δ12-desaturase sequences.

In one example of this approach, a full-length Δ12-epoxygenase-like sequence was obtained from an unidentified *Crepis* sp. containing high levels of vernolic acid in its seed oils and known not to be *Crepis palaestina*. Poly(A)+ RNA was isolated from developing seeds of this *Crepis* sp. using a QuickPrep Micro mRNA purification kit (Pharmacia Biotechnology) and used to synthesize an oligosaccharide d(T)-primed double-stranded cDNA. The double stranded cDNA thus obtained was then ligated to EcoR1/NotI adaptors (Pharmacia Biotechnology) and a cDNA library was constructed using the ZAP-cDNA Gigapack cloning kit (Stratagene). The cDNA library on Hybond N+ membrane filters (Amersham) was screened with the random-labeled D12V fragment (SEQ ID NO: 7) derived from *Crepis alpina* as prescribed by the manufacturer, using standard hybridization conditions. This resulted in the purification of a recombinant bacteriophage designated CrepX.

The nucleotide sequence of the CrepX cDNA was determined and is set forth in SEQ ID NO: 3. The deduced amino acid sequence of CrepX (SEQ ID NO: 4) comprises a 374 amino acid protein having 97% identity to the Cpal2 Δ12-epoxygenase sequence, but only 57% identity to the *Arabidopsis thaliana* L26296 Δ12-desaturase sequence. This clearly demonstrates the presence of a gene in another *Crepis* sp. having high vernolic acid content, which gene is highly homologous to the Cpal2 Δ12-epoxygenase gene and is clearly not a desaturase gene.

Example 12

Cloning of Δ12-epoxygenase Genes from *Vernonia galamensis*

Following the general strategy outlined in the preceding example, a homologue of the Cpal2 Δ12-epoxygenase gene was also obtained from *Vernonia galamensis*, containing high levels of vernolic acid in its seeds.

A partial Δ12-epoxygenase-like sequence was obtained from *V. galamensis*, by preparing first strand cDNA templates using total RNA from developing seeds as a template. A PCR fragment (550 nucleotides in length), designated as Vgal1, was obtained by amplifying the single-stranded cDNA, using primers derived from the deduced amino acid sequence of plant mixed function monooxygenases. The nucleotide sequence of the amplified DNA was determined using standard procedures and is set forth in SEQ ID NO: 5.

Alignment of the deduced amino acid sequence of the Vgal1 PCR fragment (SEQ ID NO: 6) with the full sequence of Cpal2 Δ12-epoxygenase and the *Arabidopsis thaliana* L26296 Δ12-desaturase (FIG. 2) demonstrates that the amplified Vgal1 sequence encodes an amino acid sequence corresponding to the region spanning amino acid residues 103-285 of the Cpal2 polypeptide. Within this region, the Vgal1 sequence showed greater amino acid identity with the Cpal2 Δ12-epoxygenase sequence (67%) than with the *A. thaliana* Δ12-desaturase sequence (60%), suggesting that the amplified DNA corresponds to an epoxygenase rather than a desaturase sequence.

The corresponding full-length Δ12-epoxygenase sequence was obtained from *V. galamensis*, and the nucleotide sequence of the full-length clone determined (SEQ ID NO: 19). The deduced amino acid sequence of the full-length Vgal Δ12-epoxygenase polypeptide (SEQ ID NO: 20) comprises 384 amino acids comprising all three conserved mixed function monooxygenase consensus sequences for epoxygenases as set forth in SEQ ID NOs: 15, 16, and 18 (see FIG. 2).

Example 13

Demonstration of Epoxygenase Activity for the *V. galamensis* Clone

Confirmation that the full-length cDNA clone of *V. galamensis* encodes an epoxygenase is obtained by transforming *Arabidopsis thaliana* with a binary vector comprising the isolated cDNA clone in the sense orientation and in operable connection with a promoter as described in the preceding examples. Transformed tissue is examined for the presence of epoxy fatty acids that *A. thaliana* would not otherwise produce. Additionally, the level of hydroxy fatty acids is determined, as such fatty acids can be formed from the metabolism of an epoxy fatty acid, by the action of endogenous *A. thaliana* epoxide hydrolases (Blee and Schuber, 1990).

The *V. galamensis* cDNA (SEQ ID NO: 19) was cloned into a binary vector construct, such as that shown in FIG. 4, essentially as described in the preceding examples. The Binary plasmid harboring SEQ ID NO: 19 was transformed into *Agrobacterium* strain AGL1 using electroporation and used to transform *A. thaliana*. Transgenic *A. thaliana* plants were obtained according to the method described by Valvekens et al. (1988) and Dolferus et al. (1994).

Transgenic plants and untransformed (i.e. control) plants are grown to maturity. Mature seed of each plant are analyzed for fatty acid composition by standard techniques. Primary transformant ($T_0$) plants are established and T1 seed are harvested from each plant and analyzed for their fatty acid composition by gas chromatography. $T_0$ plants are shown to contain higher levels of epoxy fatty acids in their T1 seed lipids than the seeds of untransformed control plants.

Gas chromatography of methyl esters prepared from seed lipids of T1 seed of Vgal transformed *Arabidopsis thaliana* plants is performed to show the presence of additional fatty acids compared to the untransformed controls. The retention time of these compounds permits their identification as epoxy fatty acids, and/or derivatives of epoxy fatty acids that are produced by the action of endogenous desaturase enzymes on the epoxy fatty acids.

Confirmation of the exact identity of the epoxy fatty acid products and derivatives thereof is obtained by mass spectroscopy of the diols from the epoxy fatty acid fraction of transformed plants. The diols are converted further to trimethylsilyl ethers and analyzed by GC-MS DB23 on a fused silica capillary column (Hewlett-Packard 5890 II GC coupled to a Hewlett Packard 5989A MS working in electron impact at 70 eV15).

REFERENCES

1. An et al. (1985) EMBO J. 4:277-284.
2. Ausubel, F. M., Brent, R., Kingston, R E, Moore, D. D., Seidman, J. G., Smith, J. A., and Struhl, K. (1987). In: Current Protocols in Molecular Biology. Wiley Interscience (ISBN 047150338).
3. Badami, R. C., and Patil, K. B. (1981) Progress in Lipid Research, 19, 119-53.
4. Bafor, M.; Smith, M. A., Jonsson, L., Stobart, K. and Stymne, S. (1993) Arch. Biochem. Biophys. 303, 145-151.
5. Bafor, M., Banas, A., Wiberg, E., Lenman, M., Stahl, U. and Stymne, S. (1997) In: Williams, J. P., Mobasher, K. U., Lem, N. W. (eds) Physiology, biochemistry and molecular biology of plant lipids. Kluwer Academic Publisher, Dordrecht. In-press.
6. Blee and Schuber (1990) J. Biol. Chem. 265, 12887-12894.
7. Blee, E., Wilcox, A. L., Marnett, J. M., Schuber, F. (1993) J. Biol. Chem. 268, 1798-1715.
8. Blee, E., Stahl, S., Schuber, F. and Stymne, S. (1994) Biochem. Biophys. Res. Comm. 197, 778-784
9. Bligh, E. G. and Dyer, W. J. (1959) Can. J. Biochem. Physiol. 230, 379-288.
10. Bozak, K. R., Yu, H., Sirevag, R. and Christoffersen, R. E. (1990) *Proc. Natl. Acad. Sci. USA* 87, 3904-3908.
11. Christou, P., McCabe, D. E., Swain, W. F. (1988). Plant Physiol 87, 671-674.
12. Crossway et al. (1986) Mol. Gen. Genet. 202, 179-185.
13. Devereux, J., Haeberli, P. and Smithies, O. (1984). Nucl. Acids Res. 12, 387-395.
14. Dolferus et al. Plant Physiol. (1994) 105, 1075-1087.
15. Engeseth, N. & Stymne, S. (1996) Planta 198, 238-245
16. Fromm et al. (1985) Proc. Natl. Acad. Sci. (USA) 82, 5824-5828.
17. Haseloff, J. and Gerlach, W. L. (1988). Nature 334, 586-594.
18. Herrera-Estrella et al. (1983a) Nature 303, 209-213.
19. Herrera-Estrella et al. (1983b) EMBO J. 2, 987-995.
20. Herrera-Estrella et al. (1985) In: Plant Genetic Engineering, Cambridge University Press, NY, pp 63-93.
21. Kohn, G., Hartmann, E., Stymne, S. & Beutelmann, P. (1994) J. Plant Physiol. 144, 265-271
22. Krens, F. A., Molendijk, L., Wullems, G. J. and Schilperoort, R. A. (1982). Nature 296, 72-74.
23. Lawrence, G. J., Ellis, J. G., Finnegan, E. J., Dennis, E. S. and Peacock, W. J. (1989) In: Breeding Research: The Key to Survival of the Earth (Iyama, S. and Takeda, G. eds) 6th International Congress of SABRAO. pp 535-538.
24. Lazo, G. R., Stein, P. A. and Ludwig, R. A. (1991). Bio/technology 9, 963-967.
25. Needleman and Wunsch (1970) J. Mol. Biol. 48, 443-453.
26. Pazkowski et al. (1984) EMBO J. 3, 2717-2722.

27. Pietrzak, M., Shillito, R. D., Hohn, T. and Potrykus, I. (1986). Nucl. Acids Res. 14, 5857-5868.
28. Sanger, F., Nicklin, S. and Coulson, A. R. (1977) Proc. Natl. Acad. Sci. (USA) 72, 5463-5467.
29. Shanklin, J., Whittle, E. and Fox, B. G. (1994) Biochemistry 33, 12787-12794.
30. Valvekens et al. (1988) Proc. Natl Acad. Sci. (USA) 85, 5536-5540.

---

We claim:

1. A plant seed comprising 12,13-epoxy-9-octadecenoic acid at a level of greater than 0.7% (w/w) of total seed fatty acid content in the plant seed, wherein the plant is *Arabidopsis thaliana*, flax, oilseed rape, sunflower, corn, safflower, soybean, sesame, cottonseed, peanut, olive or oil palm.

2. The plant seed of claim 1, wherein the plant is *Arabidopsis thaliana*.

3. The plant seed of claim 1, wherein the plant is flax, sunflower, corn, or safflower.

4. The plant seed of claim 3, wherein the plant is flax and the flax is *Linum usitatissimum*.

5. The plant seed of claim 3, wherein the plant is a flax plant and the plant seed contains less than 2% linolenic acid.

6. The plant seed of claim 1, wherein the plant seed further comprises 12,13-epoxy-9,15-octadecadienoic acid.

7. The plant seed of claim 3, wherein the plant seed further comprises 12,13-epoxy-9,15-octadecadienoic acid.

8. The plant seed of claim 4, wherein the plant seed further comprises 12,13-epoxy-9,15-octadecadienoic acid.

9. A process for producing oil containing epoxy fatty acids comprising obtaining as a starting material the plant seed of claim 1, and isolating from the plant seed the oil, thereby producing the oil containing epoxy fatty acids.

10. The process of claim 9, wherein the plant is *Arabidopsis thaliana*.

11. The process of claim 9, wherein the plant is flax, sunflower, corn, or safflower.

12. The process of claim 11, wherein the plant is flax and the flax is *Linum usitatissimum*.

13. The process of claim 11, wherein the plant is a flax plant and the plant seed contains less than 2% linolenic acid.

14. The process of claim 9, wherein the plant seed further comprises 12,13-epoxy-9,15-octadecadienoic acid.

15. A process for producing an epoxy fatty acid comprising obtaining as a starting material the plant seed of claim 1, and isolating from the plant seed the epoxy fatty acid, thereby producing the epoxy fatty acid.

16. The process of claim 15, wherein the plant is *Arabidopsis thaliana*.

17. The process of claim 15, wherein the plant is flax, sunflower, corn, or safflower.

18. The process of claim 17, wherein the plant is flax and the flax is *Linum usitatissimum*.

19. The process of claim 17, wherein the plant is a flax plant and the plant seed contains less than 2% linolenic acid.

20. The process of claim 15, wherein the plant seed further comprises 12,13-epoxy-9,15-octadecadienoic acid.

* * * * *

SEQUENCE LISTING

<160> NUMBER OF SEQ ID NOS: 24

<210> SEQ ID NO 1
<211> LENGTH: 1358
<212> TYPE: DNA
<213> ORGANISM: Crepis palaestina
<220> FEATURE:
<221> NAME/KEY: CDS
<222> LOCATION: (30)..(1151)
<223> OTHER INFORMATION:

<400> SEQUENCE: 1

```
gagaagttga ccataaatca tttatcaac atg ggt gcc ggc ggt cgt ggt cgg      53
                                Met Gly Ala Gly Gly Arg Gly Arg
                                 1               5 aca tcg gaa aaa tcg gtc atg gaa cgt gtc tca gtt gat cca gta acc     101
Thr Ser Glu Lys Ser Val Met Glu Arg Val Ser Val Asp Pro Val Thr
 10              15                  20 ttc tca ctg agt gaa ttg aag caa gca atc cct ccc cat tgc ttc cag     149
Phe Ser Leu Ser Glu Leu Lys Gln Ala Ile Pro Pro His Cys Phe Gln
 25                  30                  35              40 aga tct gta atc cgc tca tct tac tat gtt gtt caa gat ctc att att     197
Arg Ser Val Ile Arg Ser Ser Tyr Tyr Val Val Gln Asp Leu Ile Ile
                 45                  50                  55 gcc tac atc ttc tac ttc ctt gcc aac aca tat atc cct act ctt cct     245
Ala Tyr Ile Phe Tyr Phe Leu Ala Asn Thr Tyr Ile Pro Thr Leu Pro
             60                  65                  70 act agt cta gcc tac tta gct tgg ccc gtt tac tgg ttc tgt caa gct     293
Thr Ser Leu Ala Tyr Leu Ala Trp Pro Val Tyr Trp Phe Cys Gln Ala
         75                  80                  85 agc gtc ctc act ggc tta tgg atc ctc ggc cac gaa tgt ggt cac cat     341
Ser Val Leu Thr Gly Leu Trp Ile Leu Gly His Glu Cys Gly His His
     90                  95                 100 gcc ttt agc aac tac aca tgg ttt gac gac act gtg ggc ttc atc ctc     389
Ala Phe Ser Asn Tyr Thr Trp Phe Asp Asp Thr Val Gly Phe Ile Leu
105                 110                 115                 120 cac tca ttt ctc ctc acc ccg tat ttc tct tgg aaa ttc agt cac cgg     437
His Ser Phe Leu Leu Thr Pro Tyr Phe Ser Trp Lys Phe Ser His Arg
                125                 130                 135 aat cac cat tcc aac aca agt tcg att gat aac gat gaa gtt tac att     485
Asn His His Ser Asn Thr Ser Ser Ile Asp Asn Asp Glu Val Tyr Ile
            140                 145                 150 ccg aaa agc aag tcc aaa ctc gcg cgt atc tat aaa ctt ctt aac aac     533
Pro Lys Ser Lys Ser Lys Leu Ala Arg Ile Tyr Lys Leu Leu Asn Asn
        155                 160                 165 cca cct ggt cgg ctg ttg gtt ttg att atc atg ttc acc cta gga ttt     581
Pro Pro Gly Arg Leu Leu Val Leu Ile Ile Met Phe Thr Leu Gly Phe
    170                 175                 180 cct tta tac ctc ttg aca aat att tcc ggc aag aaa tac gac agg ttt     629
Pro Leu Tyr Leu Leu Thr Asn Ile Ser Gly Lys Lys Tyr Asp Arg Phe
185                 190                 195                 200 gcc aac cac ttc gac ccc atg agt cca att ttc aaa gaa cgt gag cgg     677
Ala Asn His Phe Asp Pro Met Ser Pro Ile Phe Lys Glu Arg Glu Arg
                205                 210                 215
```

```
ttt cag gtc ttc ctt tcg gat ctt ggt ctt ctt gcc gtg ttt tat gga    725
Phe Gln Val Phe Leu Ser Asp Leu Gly Leu Leu Ala Val Phe Tyr Gly
        220                 225                 230 att aaa gtt gct gta gca aat aaa gga gct gct tgg gta gcg tgc atg    773
Ile Lys Val Ala Val Ala Asn Lys Gly Ala Ala Trp Val Ala Cys Met
    235                 240                 245 tat gga gtt ccg gta tta ggc gta ttt acc ttt ttc gat gtg atc acc    821
Tyr Gly Val Pro Val Leu Gly Val Phe Thr Phe Phe Asp Val Ile Thr
250                 255                 260 ttc ttg cac cac acc cat cag tcg tcg cct cat tat gat tca act gaa    869
Phe Leu His His Thr His Gln Ser Ser Pro His Tyr Asp Ser Thr Glu
265                 270                 275                 280 tgg aac tgg atc aga ggg gcc ttg tca gca atc gat agg gac ttt gga    917
Trp Asn Trp Ile Arg Gly Ala Leu Ser Ala Ile Asp Arg Asp Phe Gly
            285                 290                 295 ttc ctg aat agt gtt ttc cat gat gtt aca cac act cat gtc atg cat    965
Phe Leu Asn Ser Val Phe His Asp Val Thr His Thr His Val Met His
        300                 305                 310 cat ttg ttt tca tac att cca cac tat cat gca aag gag gca agg gat   1013
His Leu Phe Ser Tyr Ile Pro His Tyr His Ala Lys Glu Ala Arg Asp
    315                 320                 325 gca atc aag cca atc ttg ggc gac ttt tat atg atc gac agg act cca   1061
Ala Ile Lys Pro Ile Leu Gly Asp Phe Tyr Met Ile Asp Arg Thr Pro
330                 335                 340 att tta aaa gca atg tgg aga gag ggc agg gag tgc atg tac atc gag   1109
Ile Leu Lys Ala Met Trp Arg Glu Gly Arg Glu Cys Met Tyr Ile Glu
345                 350                 355                 360 cct gat agc aag ctc aaa ggt gtt tat tgg tat cat aaa ttg            1151
Pro Asp Ser Lys Leu Lys Gly Val Tyr Trp Tyr His Lys Leu
            365                 370 tgatcatatg caaaatgcac atgcattttc aaaccctcta gttacgtttg ttctatgtat   1211
aataaaccgc cggtcctttg gttgactatg cctaagccag gcgaaacagt taaataatat   1271
cggtatgatg tgtaatgaaa gtatgtggtt gtctggtttt gttgctatga agaaagtat    1331 gtggttgtcg gtcaaaaaaa aaaaaaa                                      1358

<210> SEQ ID NO 2
<211> LENGTH: 374
<212> TYPE: PRT
<213> ORGANISM: Crepis palaestina

<400> SEQUENCE: 2

Met Gly Ala Gly Gly Arg Gly Arg Thr Ser Glu Lys Ser Val Met Glu
1               5                   10                  15

Arg Val Ser Val Asp Pro Val Thr Phe Ser Leu Ser Glu Leu Lys Gln
            20                  25                  30

Ala Ile Pro Pro His Cys Phe Gln Arg Ser Val Ile Arg Ser Ser Tyr
        35                  40                  45

Tyr Val Val Gln Asp Leu Ile Ile Ala Tyr Ile Phe Tyr Phe Leu Ala
    50                  55                  60

Asn Thr Tyr Ile Pro Thr Leu Pro Thr Ser Leu Ala Tyr Leu Ala Trp
65                  70                  75                  80

Pro Val Tyr Trp Phe Cys Gln Ala Ser Val Leu Thr Gly Leu Trp Ile
                85                  90                  95

Leu Gly His Glu Cys Gly His His Ala Phe Ser Asn Tyr Thr Trp Phe
            100                 105                 110

Asp Asp Thr Val Gly Phe Ile Leu His Ser Phe Leu Leu Thr Pro Tyr
        115                 120                 125
```

```
Phe Ser Trp Lys Phe Ser His Arg Asn His His Ser Asn Thr Ser Ser
    130                 135                 140
Ile Asp Asn Asp Glu Val Tyr Ile Pro Lys Ser Lys Ser Lys Leu Ala
145                 150                 155                 160
Arg Ile Tyr Lys Leu Leu Asn Asn Pro Pro Gly Arg Leu Leu Val Leu
                165                 170                 175
Ile Ile Met Phe Thr Leu Gly Phe Pro Leu Tyr Leu Thr Asn Ile
            180                 185                 190
Ser Gly Lys Lys Tyr Asp Arg Phe Ala Asn His Phe Asp Pro Met Ser
        195                 200                 205
Pro Ile Phe Lys Glu Arg Glu Arg Phe Gln Val Phe Leu Ser Asp Leu
    210                 215                 220
Gly Leu Leu Ala Val Phe Tyr Gly Ile Lys Val Ala Val Ala Asn Lys
225                 230                 235                 240
Gly Ala Ala Trp Val Ala Cys Met Tyr Gly Val Pro Val Leu Gly Val
                245                 250                 255
Phe Thr Phe Phe Asp Val Ile Thr Phe Leu His His Thr His Gln Ser
            260                 265                 270
Ser Pro His Tyr Asp Ser Thr Glu Trp Asn Trp Ile Arg Gly Ala Leu
        275                 280                 285
Ser Ala Ile Asp Arg Asp Phe Gly Phe Leu Asn Ser Val Phe His Asp
    290                 295                 300
Val Thr His Thr His Val Met His His Leu Phe Ser Tyr Ile Pro His
305                 310                 315                 320
Tyr His Ala Lys Glu Ala Arg Asp Ala Ile Lys Pro Ile Leu Gly Asp
                325                 330                 335
Phe Tyr Met Ile Asp Arg Thr Pro Ile Leu Lys Ala Met Trp Arg Glu
            340                 345                 350
Gly Arg Glu Cys Met Tyr Ile Glu Pro Asp Ser Lys Leu Lys Gly Val
        355                 360                 365
Tyr Trp Tyr His Lys Leu
    370

<210> SEQ ID NO 3
<211> LENGTH: 1309
<212> TYPE: DNA
<213> ORGANISM: Crepis sp.
<220> FEATURE:
<221> NAME/KEY: misc_feature
<222> LOCATION: (937)..(937)
<223> OTHER INFORMATION: N is any nucleotide residue
<220> FEATURE:
<221> NAME/KEY: CDS
<222> LOCATION: (26)..(1147)
<223> OTHER INFORMATION:
<220> FEATURE:
<221> NAME/KEY: misc_feature
<222> LOCATION: (901)..(901)
<223> OTHER INFORMATION: N is any nucleotide residue

<400> SEQUENCE: 3
tgttgaccat aaatcatcta tcaac atg ggt gcc ggc ggc cgt ggt cgg tcg        52
                           Met Gly Ala Gly Gly Arg Gly Arg Ser
                             1               5 gaa aag tcg gtc atg gaa cgt gtc tca gtt gat cca gta acc ttc tca      100
Glu Lys Ser Val Met Glu Arg Val Ser Val Asp Pro Val Thr Phe Ser
 10              15                  20                  25 ctg agt gat ttg aag caa gca atc cct cca cat tgc ttc cag cga tct      148
Leu Ser Asp Leu Lys Gln Ala Ile Pro Pro His Cys Phe Gln Arg Ser
```

-continued

```
                30                  35                  40
gtc atc cgt tca tct tat tac gtt gtt cag gat ctc ata att gcc tac     196
Val Ile Arg Ser Ser Tyr Tyr Val Val Gln Asp Leu Ile Ile Ala Tyr
             45                  50                  55 atc ttc tac ttc ctt gcc aac aca tat atc cct aat ctc cct cat cct     244
Ile Phe Tyr Phe Leu Ala Asn Thr Tyr Ile Pro Asn Leu Pro His Pro
         60                  65                  70 cta gcc tac tta gct tgg ccg ctt tac tgg ttc tgt caa gct agc gtc     292
Leu Ala Tyr Leu Ala Trp Pro Leu Tyr Trp Phe Cys Gln Ala Ser Val
     75                  80                  85 ctc act ggg tta tgg atc ctc ggc cat gaa tgt ggt cac cat gcc tat     340
Leu Thr Gly Leu Trp Ile Leu Gly His Glu Cys Gly His His Ala Tyr
 90                  95                 100                 105 agc aac tac aca tgg gtt gac gac act gtg ggc ttc atc atc cat tca     388
Ser Asn Tyr Thr Trp Val Asp Asp Thr Val Gly Phe Ile Ile His Ser
                110                 115                 120 ttt ctc ctc acc ccg tat ttc tct tgg aaa tac agt cac cgg aat cac     436
Phe Leu Leu Thr Pro Tyr Phe Ser Trp Lys Tyr Ser His Arg Asn His
            125                 130                 135 cat tcc aac aca agt tcg att gat aac gat gaa gtt tac att ccg aaa     484
His Ser Asn Thr Ser Ser Ile Asp Asn Asp Glu Val Tyr Ile Pro Lys
        140                 145                 150 agc aag tcc aaa ctc aag cgt atc tat aaa ctt ctt aac aac cca cct     532
Ser Lys Ser Lys Leu Lys Arg Ile Tyr Lys Leu Leu Asn Asn Pro Pro
    155                 160                 165 ggt cga ctg ttg gtt ttg gtt atc atg ttc acc cta gga ttt cct tta     580
Gly Arg Leu Leu Val Leu Val Ile Met Phe Thr Leu Gly Phe Pro Leu
170                 175                 180                 185 tac ctc ttg aca aat att tcc ggc aag aaa tac gat agg ttt gcc aac     628
Tyr Leu Leu Thr Asn Ile Ser Gly Lys Lys Tyr Asp Arg Phe Ala Asn
                190                 195                 200 cac ttc gac ccc atg agt cca att ttc aaa gaa cgt gag cgg ttt cag     676
His Phe Asp Pro Met Ser Pro Ile Phe Lys Glu Arg Glu Arg Phe Gln
            205                 210                 215 gtc ttc ctt tcg gat ctt ggt ctt ctt gct gtg ttt tat gga att aaa     724
Val Phe Leu Ser Asp Leu Gly Leu Leu Ala Val Phe Tyr Gly Ile Lys
        220                 225                 230 gtt gct gta gca aat aaa gga gct gct tgg gtg gcg tgc atg tat gga     772
Val Ala Val Ala Asn Lys Gly Ala Ala Trp Val Ala Cys Met Tyr Gly
    235                 240                 245 gtt ccg gtg cta ggc gta ttt acc ttt ttc gat gtg atc acg ttc tta     820
Val Pro Val Leu Gly Val Phe Thr Phe Phe Asp Val Ile Thr Phe Leu
250                 255                 260                 265 cac cac acc cat cag tcg tcg cct cat tat gat tca act gaa tgg aac     868
His His Thr His Gln Ser Ser Pro His Tyr Asp Ser Thr Glu Trp Asn
                270                 275                 280 tgg atc aga ggg gct ttg tca gca atc gat agn gac ttt ggg ttc ctg     916
Trp Ile Arg Gly Ala Leu Ser Ala Ile Asp Xaa Asp Phe Gly Phe Leu
            285                 290                 295 aat agt gtt ttc cat gat gtn aca cac act cac gtc atg cat cat ttg     964
Asn Ser Val Phe His Asp Val Thr His Thr His Val Met His His Leu
        300                 305                 310 ttt tca tac att cca cac tat cat gca aag gaa gca agg gat gca atc    1012
Phe Ser Tyr Ile Pro His Tyr His Ala Lys Glu Ala Arg Asp Ala Ile
    315                 320                 325 aaa ccg atc ttg ggc gac ttt tat atg atc gat agg act cca att tta    1060
Lys Pro Ile Leu Gly Asp Phe Tyr Met Ile Asp Arg Thr Pro Ile Leu
330                 335                 340                 345 aaa gca atg tgg aga gag ggc agg gaa tgc atg tac atc gag cct gat    1108
```

-continued

```
Lys Ala Met Trp Arg Glu Gly Arg Glu Cys Met Tyr Ile Glu Pro Asp
            350                 355                 360 agc aag ctc aaa ggt gtt tat tgg tat cat aaa ttg tga tcatatgcaa      1157
Ser Lys Leu Lys Gly Val Tyr Trp Tyr His Lys Leu
            365                 370 aatgcacatg cattttcaaa ccctctagtt acctttgttc tatgtataat aagaccgccg   1217
gtcctatggt tttctatgcc taagccaggc gaaatagtta ataatatcg gtatgatgta    1277 atgaaagtat gtggttgtct aaaaaaaaaa aa                                 1309

<210> SEQ ID NO 4
<211> LENGTH: 373
<212> TYPE: PRT
<213> ORGANISM: Crepis sp.
<220> FEATURE:
<221> NAME/KEY: misc_feature
<222> LOCATION: (292)..(292)
<223> OTHER INFORMATION: The 'Xaa' at location 292 stands for Arg, or
      Ser.
<220> FEATURE:
<221> NAME/KEY: misc_feature
<222> LOCATION: (937)..(937)
<223> OTHER INFORMATION: N is any nucleotide residue
<220> FEATURE:
<221> NAME/KEY: misc_feature
<222> LOCATION: (901)..(901)
<223> OTHER INFORMATION: N is any nucleotide residue

<400> SEQUENCE: 4

Met Gly Ala Gly Gly Arg Gly Arg Ser Glu Lys Ser Val Met Glu Arg
1               5                   10                  15

Val Ser Val Asp Pro Val Thr Phe Ser Leu Ser Asp Leu Lys Gln Ala
            20                  25                  30

Ile Pro Pro His Cys Phe Gln Arg Ser Val Ile Arg Ser Ser Tyr Tyr
        35                  40                  45

Val Val Gln Asp Leu Ile Ile Ala Tyr Ile Phe Tyr Phe Leu Ala Asn
    50                  55                  60

Thr Tyr Ile Pro Asn Leu Pro His Pro Leu Ala Tyr Leu Ala Trp Pro
65                  70                  75                  80

Leu Tyr Trp Phe Cys Gln Ala Ser Val Leu Thr Gly Leu Trp Ile Leu
                85                  90                  95

Gly His Glu Cys Gly His His Ala Tyr Ser Asn Tyr Thr Trp Val Asp
            100                 105                 110

Asp Thr Val Gly Phe Ile Ile His Ser Phe Leu Leu Thr Pro Tyr Phe
        115                 120                 125

Ser Trp Lys Tyr Ser His Arg Asn His His Ser Asn Thr Ser Ser Ile
    130                 135                 140

Asp Asn Asp Glu Val Tyr Ile Pro Lys Ser Lys Ser Lys Leu Lys Arg
145                 150                 155                 160

Ile Tyr Lys Leu Leu Asn Asn Pro Pro Gly Arg Leu Leu Val Leu Val
                165                 170                 175

Ile Met Phe Thr Leu Gly Phe Pro Leu Tyr Leu Leu Thr Asn Ile Ser
            180                 185                 190

Gly Lys Lys Tyr Asp Arg Phe Ala Asn His Phe Asp Pro Met Ser Pro
        195                 200                 205

Ile Phe Lys Glu Arg Glu Arg Phe Gln Val Phe Leu Ser Asp Leu Gly
    210                 215                 220

Leu Leu Ala Val Phe Tyr Gly Ile Lys Val Ala Val Ala Asn Lys Gly
225                 230                 235                 240
```

```
Ala Ala Trp Val Ala Cys Met Tyr Gly Val Pro Val Leu Gly Val Phe
            245                 250                 255

Thr Phe Phe Asp Val Ile Thr Phe Leu His His Thr His Gln Ser Ser
            260                 265                 270

Pro His Tyr Asp Ser Thr Glu Trp Asn Trp Ile Arg Gly Ala Leu Ser
            275                 280                 285

Ala Ile Asp Xaa Asp Phe Gly Phe Leu Asn Ser Val Phe His Asp Val
            290                 295                 300

Thr His Thr His Val Met His His Leu Phe Ser Tyr Ile Pro His Tyr
305                 310                 315                 320

His Ala Lys Glu Ala Arg Asp Ala Ile Lys Pro Ile Leu Gly Asp Phe
            325                 330                 335

Tyr Met Ile Asp Arg Thr Pro Ile Leu Lys Ala Met Trp Arg Glu Gly
            340                 345                 350

Arg Glu Cys Met Tyr Ile Glu Pro Asp Ser Lys Leu Lys Gly Val Tyr
            355                 360                 365

Trp Tyr His Lys Leu
    370

<210> SEQ ID NO 5
<211> LENGTH: 550
<212> TYPE: DNA
<213> ORGANISM: Vernonia galamensis
<220> FEATURE:
<221> NAME/KEY: CDS
<222> LOCATION: (1)..(549)
<223> OTHER INFORMATION:

<400> SEQUENCE: 5 cat cac gcc ttc agt gac tat caa tgg ata gac gac act gtg ggc ttc      48
His His Ala Phe Ser Asp Tyr Gln Trp Ile Asp Asp Thr Val Gly Phe
1               5                   10                  15 atc ctt cac ttt gca ctc ttc acc cct tat ttc tct tgg aaa tac agt      96
Ile Leu His Phe Ala Leu Phe Thr Pro Tyr Phe Ser Trp Lys Tyr Ser
            20                  25                  30 cac cgt aat cac cat gcc aac aca aac tct ctt gta acc gat gaa gta     144
His Arg Asn His His Ala Asn Thr Asn Ser Leu Val Thr Asp Glu Val
        35                  40                  45 tac atc cct aaa gtt aaa tcc aag gtc aag att tat tcc aaa atc ctt     192
Tyr Ile Pro Lys Val Lys Ser Lys Val Lys Ile Tyr Ser Lys Ile Leu
    50                  55                  60 aac aac cct cct ggt cgc gtt ttc acc ttg gct ttc aga ttg atc gtg     240
Asn Asn Pro Pro Gly Arg Val Phe Thr Leu Ala Phe Arg Leu Ile Val
65                  70                  75                  80 ggt ttt cct tta tac ctt ttc acc aat gtt tca ggc aag aaa tac gaa     288
Gly Phe Pro Leu Tyr Leu Phe Thr Asn Val Ser Gly Lys Lys Tyr Glu
                85                  90                  95 cgt ttt gcc aac cat ttt gat ccc atg agt ccc att ttc acc gag cgt     336
Arg Phe Ala Asn His Phe Asp Pro Met Ser Pro Ile Phe Thr Glu Arg
            100                 105                 110 gag cat gta caa gtc ttg ctt tct gat ttt ggt ctc ata gca gtt gct     384
Glu His Val Gln Val Leu Leu Ser Asp Phe Gly Leu Ile Ala Val Ala
        115                 120                 125 tac gtg gtt cgt caa gct gta ctg gct aaa gga ggt gct tgg gtg atg     432
Tyr Val Val Arg Gln Ala Val Leu Ala Lys Gly Gly Ala Trp Val Met
    130                 135                 140 tgc att tac gga gtt cct gtg ctg gcc gta aac gca ttc ttt gtt tta     480
Cys Ile Tyr Gly Val Pro Val Leu Ala Val Asn Ala Phe Phe Val Leu
145                 150                 155                 160
```

```
atc act tat ctt cac cac acg cat ctc tca ctg ccc cac tat gat agc     528
Ile Thr Tyr Leu His His Thr His Leu Ser Leu Pro His Tyr Asp Ser
                165                 170                 175 tca gaa tgg gac tgg cta cga g                                        550
Ser Glu Trp Asp Trp Leu Arg
            180
```

<210> SEQ ID NO 6
<211> LENGTH: 183
<212> TYPE: PRT
<213> ORGANISM: Vernonia galamensis

<400> SEQUENCE: 6

```
His His Ala Phe Ser Asp Tyr Gln Trp Ile Asp Asp Thr Val Gly Phe
1               5                   10                  15

Ile Leu His Phe Ala Leu Phe Thr Pro Tyr Phe Ser Trp Lys Tyr Ser
                20                  25                  30

His Arg Asn His His Ala Asn Thr Asn Ser Leu Val Thr Asp Glu Val
            35                  40                  45

Tyr Ile Pro Lys Val Lys Ser Lys Val Lys Ile Tyr Ser Lys Ile Leu
    50                  55                  60

Asn Asn Pro Pro Gly Arg Val Phe Thr Leu Ala Phe Arg Leu Ile Val
65                  70                  75                  80

Gly Phe Pro Leu Tyr Leu Phe Thr Asn Val Ser Gly Lys Lys Tyr Glu
                85                  90                  95

Arg Phe Ala Asn His Phe Asp Pro Met Ser Pro Ile Phe Thr Glu Arg
            100                 105                 110

Glu His Val Gln Val Leu Leu Ser Asp Phe Gly Leu Ile Ala Val Ala
        115                 120                 125

Tyr Val Val Arg Gln Ala Val Leu Ala Lys Gly Gly Ala Trp Val Met
    130                 135                 140

Cys Ile Tyr Gly Val Pro Val Leu Ala Val Asn Ala Phe Phe Val Leu
145                 150                 155                 160

Ile Thr Tyr Leu His His Thr His Leu Ser Leu Pro His Tyr Asp Ser
                165                 170                 175

Ser Glu Trp Asp Trp Leu Arg
            180
```

<210> SEQ ID NO 7
<211> LENGTH: 177
<212> TYPE: DNA
<213> ORGANISM: Crepis alpina
<220> FEATURE:
<221> NAME/KEY: CDS
<222> LOCATION: (1)..(177)
<223> OTHER INFORMATION:

<400> SEQUENCE: 7

```
gaa tgc ggt cac cat gcc ttc agc gac tac cag tgg gtt gac gac aat     48
Glu Cys Gly His His Ala Phe Ser Asp Tyr Gln Trp Val Asp Asp Asn
1               5                   10                  15 gtg ggc ttc atc ctc cac tcg ttt ctc atg acc ccg tat ttc tcc tgg     96
Val Gly Phe Ile Leu His Ser Phe Leu Met Thr Pro Tyr Phe Ser Trp
                20                  25                  30 aaa tac agc cac cgg aac cac cat gcc aac aca aat tcg ctt gac aac    144
Lys Tyr Ser His Arg Asn His His Ala Asn Thr Asn Ser Leu Asp Asn
            35                  40                  45 gat gaa gtt tac atc ccc aaa agc aag gcc aaa                        177
Asp Glu Val Tyr Ile Pro Lys Ser Lys Ala Lys
    50                  55
```

<210> SEQ ID NO 8
<211> LENGTH: 59
<212> TYPE: PRT
<213> ORGANISM: Crepis alpina

<400> SEQUENCE: 8

```
Glu Cys Gly His His Ala Phe Ser Asp Tyr Gln Trp Val Asp Asp Asn
1               5                   10                  15

Val Gly Phe Ile Leu His Ser Phe Leu Met Thr Pro Tyr Phe Ser Trp
            20                  25                  30

Lys Tyr Ser His Arg Asn His His Ala Asn Thr Asn Ser Leu Asp Asn
        35                  40                  45

Asp Glu Val Tyr Ile Pro Lys Ser Lys Ala Lys
    50                  55
```

<210> SEQ ID NO 9
<211> LENGTH: 383
<212> TYPE: PRT
<213> ORGANISM: Arabidopsis thaliana

<400> SEQUENCE: 9

```
Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
            20                  25                  30

Val Gly Asp Leu Lys Lys Ala Ile Pro Pro His Cys Phe Lys Arg Ser
        35                  40                  45

Ile Pro Arg Ser Phe Ser Tyr Leu Ile Ser Asp Ile Ile Ala Ser
    50                  55                  60

Cys Phe Tyr Tyr Val Ala Thr Asn Tyr Phe Ser Leu Leu Pro Gln Pro
65                  70                  75                  80

Leu Ser Tyr Leu Ala Trp Pro Leu Tyr Trp Ala Cys Gln Gly Cys Val
                85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270
```

```
Gln His Thr His Pro Ser Leu Pro His Tyr Asp Ser Ser Glu Trp Asp
            275                 280                 285

Trp Leu Arg Gly Ala Leu Ala Thr Val Asp Arg Asp Tyr Gly Ile Leu
        290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
        355                 360                 365

Arg Glu Gly Asp Lys Lys Gly Val Tyr Trp Tyr Asn Asn Lys Leu
    370                 375                 380

<210> SEQ ID NO 10
<211> LENGTH: 384
<212> TYPE: PRT
<213> ORGANISM: Brassica juncea

<400> SEQUENCE: 10

Met Gly Ala Gly Gly Arg Met Gln Val Ser Pro Ser Pro Lys Lys Ser
1               5                   10                  15

Glu Thr Asp Thr Leu Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Val Ala Ser
    50                  55                  60

Cys Phe Tyr Tyr Val Ala Thr Thr Tyr Phe Pro Leu Leu Pro His Pro
65                  70                  75                  80

Leu Ser Tyr Val Ala Trp Pro Leu Tyr Trp Ala Cys Gln Gly Val Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Trp Ala Phe Asn Val Ser Gly Arg Pro Tyr Pro Glu Gly Phe Ala
        195                 200                 205

Cys His Phe His Pro Asn Ala Pro Ile Tyr Asn Asp Arg Glu Arg Leu
    210                 215                 220

Gln Ile Tyr Val Ser Asp Ala Gly Ile Leu Ala Val Cys Tyr Gly Leu
225                 230                 235                 240

Tyr Arg Tyr Ala Ala Ala Gln Gly Val Ala Ser Met Val Cys Leu Tyr
                245                 250                 255

Gly Val Pro Leu Leu Ile Val Asn Ala Phe Leu Val Leu Ile Thr Tyr
```

```
                   260                 265                 270
Leu Gln His Thr His Pro Ser Leu Pro His Tyr Asp Ser Ser Glu Trp
                275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Val Thr Lys Ala
                325                 330                 335

Ile Lys Pro Ile Leu Gly Asp Tyr Tyr Gln Phe Asp Gly Thr Pro Trp
            340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
            370                 375                 380
```

<210> SEQ ID NO 11
<211> LENGTH: 367
<212> TYPE: PRT
<213> ORGANISM: Glycine max

<400> SEQUENCE: 11

```
Met Gly Ala Gly Gly Arg Thr Asp Val Pro Ala Asn Arg Lys Ser
1               5                   10                  15

Glu Val Asp Pro Leu Lys Arg Val Pro Phe Glu Lys Pro Gln Phe Ser
            20                  25                  30

Leu Ser Gln Ile Lys Lys Ala Ile Pro Pro His Cys Phe Gln Arg Ser
                35                  40                  45

Val Leu Arg Ser Phe Ser Tyr Val Val Tyr Asp Leu Thr Ile Ala Phe
            50                  55                  60

Cys Leu Tyr Tyr Val Ala Thr His Tyr Phe His Leu Leu Pro Gly Pro
65                  70                  75                  80

Leu Ser Phe Arg Gly Met Ala Ile Tyr Trp Ala Val Gln Gly Cys Ile
                85                  90                  95

Leu Thr Gly Val Trp Val Ile Ala His Glu Cys Gly His His Ala Phe
            100                 105                 110

Ser Asp Tyr Gln Leu Leu Asp Asp Ile Val Gly Leu Ile Leu His Ser
                115                 120                 125

Ala Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Gly Arg Val Leu Thr Leu Ala Val Thr Leu Thr Leu Gly Trp Pro Leu
                165                 170                 175

Tyr Leu Ala Leu Asn Val Ser Gly Arg Pro Tyr Asp Arg Phe Ala Cys
            180                 185                 190

His Tyr Asp Pro Tyr Gly Pro Ile Tyr Ser Asp Arg Glu Arg Leu Gln
                195                 200                 205

Ile Tyr Ile Ser Asp Ala Gly Val Leu Ala Val Val Tyr Gly Leu Phe
            210                 215                 220

Arg Leu Ala Met Ala Lys Gly Leu Ala Trp Val Val Cys Val Tyr Gly
225                 230                 235                 240

Val Pro Leu Leu Val Val Asn Gly Phe Leu Val Leu Ile Thr Phe Leu
                245                 250                 255
```

```
Gln His Thr His Pro Ala Leu Pro His Tyr Thr Ser Ser Glu Trp Asp
            260                 265                 270

Trp Leu Arg Gly Ala Leu Ala Thr Val Asp Arg Asp Tyr Gly Ile Leu
        275                 280                 285

Asn Lys Val Phe His Asn Ile Thr Asp Thr His Val Ala His His Leu
    290                 295                 300

Phe Ser Thr Met Pro His Tyr His Ala Met Glu Ala Thr Lys Ala Ile
305                 310                 315                 320

Lys Pro Ile Leu Gly Glu Tyr Tyr Arg Phe Asp Glu Thr Pro Phe Val
                325                 330                 335

Lys Ala Met Trp Arg Glu Ala Arg Glu Cys Ile Tyr Val Glu Pro Asp
            340                 345                 350

Gln Ser Thr Glu Ser Lys Gly Val Phe Trp Tyr Asn Asn Lys Leu
        355                 360                 365
```

<210> SEQ ID NO 12
<211> LENGTH: 383
<212> TYPE: PRT
<213> ORGANISM: Solanum commersonii

<400> SEQUENCE: 12

```
Met Gly Ala Gly Gly Arg Met Ser Ala Pro Asn Gly Glu Thr Glu Val
1               5                   10                  15

Lys Arg Asn Pro Leu Gln Lys Val Pro Thr Ser Lys Pro Pro Phe Thr
            20                  25                  30

Val Gly Asp Ile Lys Lys Ala Ile Pro Pro His Cys Phe Gln Arg Ser
        35                  40                  45

Leu Ile Arg Ser Phe Ser Tyr Val Val Tyr Asp Leu Ile Leu Val Ser
    50                  55                  60

Ile Met Tyr Tyr Val Ala Asn Thr Tyr Phe His Leu Leu Pro Ser Pro
65                  70                  75                  80

Tyr Cys Tyr Ile Ala Trp Pro Ile Tyr Trp Ile Cys Gln Gly Cys Val
                85                  90                  95

Cys Thr Gly Ile Trp Val Asn Ala His Glu Cys Gly His His Ala Phe
            100                 105                 110

Ser Asp Tyr Gln Trp Val Asp Asp Thr Val Gly Leu Ile Leu His Ser
        115                 120                 125

Ala Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Pro Lys Ser Gln Leu Gly Trp Tyr Ser Lys Tyr Leu Asn Asn Pro Pro
                165                 170                 175

Gly Arg Val Leu Ser Leu Thr Ile Thr Leu Thr Leu Gly Trp Pro Leu
            180                 185                 190

Tyr Leu Ala Phe Asn Val Ser Gly Arg Pro Tyr Asp Arg Phe Ala Cys
        195                 200                 205

His Tyr Asp Pro Tyr Gly Pro Ile Tyr Asn Asn Arg Glu Arg Leu Gln
    210                 215                 220

Ile Phe Ile Ser Asp Ala Gly Val Leu Gly Val Cys Tyr Leu Leu Tyr
225                 230                 235                 240

Arg Ile Ala Leu Val Lys Gly Leu Ala Trp Leu Val Cys Val Tyr Gly
                245                 250                 255

Val Pro Leu Leu Val Val Asn Gly Phe Leu Val Leu Ile Thr Tyr Leu
            260                 265                 270
```

```
Gln His Thr His Pro Ser Leu Pro His Tyr Asp Ser Thr Glu Trp Asp
        275                 280                 285

Trp Leu Arg Gly Ala Leu Ala Thr Cys Asp Arg Asp Tyr Gly Val Leu
        290                 295                 300

Asn Lys Val Phe His Asn Ile Thr Asp Thr His Val Val His His Leu
305                 310                 315                 320

Phe Ser Thr Met Pro His Tyr Asn Ala Met Glu Ala Thr Lys Ala Val
                325                 330                 335

Lys Pro Leu Leu Gly Asp Tyr Tyr Gln Phe Asp Gly Thr Pro Ile Tyr
            340                 345                 350

Lys Glu Met Trp Arg Glu Ala Lys Glu Cys Leu Tyr Val Glu Lys Asp
        355                 360                 365

Glu Ser Ser Gln Gly Lys Gly Val Phe Trp Tyr Lys Asn Lys Leu
        370                 375                 380
```

<210> SEQ ID NO 13
<211> LENGTH: 387
<212> TYPE: PRT
<213> ORGANISM: Glycine max

<400> SEQUENCE: 13

```
Met Gly Leu Ala Lys Glu Thr Thr Met Gly Gly Arg Gly Arg Val Ala
1               5                   10                  15

Lys Val Glu Val Gln Gly Lys Lys Pro Leu Ser Arg Val Pro Asn Thr
            20                  25                  30

Lys Pro Pro Phe Thr Val Gly Gln Leu Lys Lys Ala Ile Pro Pro His
        35                  40                  45

Cys Phe Gln Arg Ser Leu Leu Thr Ser Phe Ser Tyr Val Val Tyr Asp
    50                  55                  60

Leu Ser Phe Ala Phe Ile Phe Tyr Ile Ala Thr Thr Tyr Phe His Leu
65                  70                  75                  80

Leu Pro Gln Pro Phe Ser Leu Ile Ala Trp Pro Ile Tyr Trp Val Leu
                85                  90                  95

Gln Gly Cys Leu Leu Thr Gly Val Trp Val Ile Ala His Glu Cys Gly
            100                 105                 110

His His Ala Phe Ser Lys Tyr Gln Trp Val Asp Asp Val Val Gly Leu
        115                 120                 125

Thr Leu His Ser Thr Leu Leu Val Pro Tyr Phe Ser Trp Lys Ile Ser
    130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
            180                 185                 190

Gly Trp Pro Met Tyr Leu Ala Phe Asn Val Ser Gly Arg Pro Tyr Asp
        195                 200                 205

Ser Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240

Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
```

```
                260                 265                 270
Ile Thr Tyr Leu Gln His Thr His Phe Ala Leu Pro His Tyr Asp Ser
            275                 280                 285

Ser Glu Trp Asp Trp Leu Lys Gly Ala Leu Ala Thr Met Asp Arg Asp
        290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Met Glu Ala
                325                 330                 335

Thr Asn Ala Ile Lys Pro Ile Leu Gly Glu Tyr Gln Phe Asp Asp
            340                 345                 350

Thr Pro Phe Tyr Lys Ala Leu Trp Arg Glu Ala Arg Glu Cys Leu Tyr
                355                 360                 365

Val Glu Pro Asp Glu Gly Thr Ser Glu Lys Gly Val Tyr Trp Tyr Arg
370                 375                 380

Asn Lys Tyr
385

<210> SEQ ID NO 14
<211> LENGTH: 387
<212> TYPE: PRT
<213> ORGANISM: Ricinus communis

<400> SEQUENCE: 14

Met Gly Gly Gly Gly Arg Met Ser Thr Val Ile Thr Ser Asn Asn Ser
1               5                   10                  15

Glu Lys Lys Gly Gly Ser Ser His Leu Lys Arg Ala Pro His Thr Lys
            20                  25                  30

Pro Pro Phe Thr Leu Gly Asp Leu Lys Arg Ala Ile Pro Pro His Cys
        35                  40                  45

Phe Glu Arg Ser Phe Val Arg Ser Phe Ser Tyr Val Ala Tyr Asp Val
    50                  55                  60

Cys Leu Ser Phe Leu Phe Tyr Ser Ile Ala Thr Asn Phe Phe Pro Tyr
65                  70                  75                  80

Ile Ser Ser Pro Leu Ser Tyr Val Ala Trp Leu Val Tyr Trp Leu Phe
                85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
    130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Ser
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
    210                 215                 220

Glu Arg Leu Gln Ile Tyr Ile Ala Asp Leu Gly Ile Phe Ala Thr Thr
225                 230                 235                 240
```

```
Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285

Ser Glu Trp Asp Trp Leu Arg Gly Ala Met Val Thr Val Asp Arg Asp
    290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 15
<211> LENGTH: 6
<212> TYPE: PRT
<213> ORGANISM: mixed function monooxygenase peptide motif

<400> SEQUENCE: 15

His Glu Cys Gly His His
1               5

<210> SEQ ID NO 16
<211> LENGTH: 5
<212> TYPE: PRT
<213> ORGANISM: mixed function monooxygenase peptide motif

<400> SEQUENCE: 16

His Arg Asn His His
1               5

<210> SEQ ID NO 17
<211> LENGTH: 5
<212> TYPE: PRT
<213> ORGANISM: mixed function monooxygenase peptide motif

<400> SEQUENCE: 17

His Val Met His His
1               5

<210> SEQ ID NO 18
<211> LENGTH: 5
<212> TYPE: PRT
<213> ORGANISM: mixed function monooxygenase peptide motif

<400> SEQUENCE: 18

His Val Leu His His
1               5

<210> SEQ ID NO 19
<211> LENGTH: 1199
<212> TYPE: DNA
<213> ORGANISM: Vernonia galamensis
```

```
<220> FEATURE:
<221> NAME/KEY: CDS
<222> LOCATION: (44)..(1195)
<223> OTHER INFORMATION:

<400> SEQUENCE: 19
tattacacat ttacactgat ctgttaatca aatttcaaac aaa atg gga gct ggt      55
                                              Met Gly Ala Gly
                                              1 ggc cga atg aat acc acc gat gat gat cag aag aat ctc ttc caa cgc     103
Gly Arg Met Asn Thr Thr Asp Asp Asp Gln Lys Asn Leu Phe Gln Arg
 5              10                  15                  20 gta cca gcc tcc aaa cca cca ttc tcc ttg gct gat ctt aag aaa gcc     151
Val Pro Ala Ser Lys Pro Pro Phe Ser Leu Ala Asp Leu Lys Lys Ala
             25                  30                  35 ata cca ccc cac tgt ttc caa aga tcc ctc ctc cgt tca tct tac tat     199
Ile Pro Pro His Cys Phe Gln Arg Ser Leu Leu Arg Ser Ser Tyr Tyr
         40                  45                  50 gtg gtt cat gat ctc gtc gta gcc tac gtc ttt tac tat ctc gcc aac     247
Val Val His Asp Leu Val Val Ala Tyr Val Phe Tyr Tyr Leu Ala Asn
     55                  60                  65 aca tac atc cct ctt ctt ccc tcc cct ctt gcc tac tta tta gct tgg     295
Thr Tyr Ile Pro Leu Leu Pro Ser Pro Leu Ala Tyr Leu Leu Ala Trp
 70                  75                  80 ccc ctt tac tgg ttc tgt cag ggt agc atc ctc acc ggt gtc tgg gtc     343
Pro Leu Tyr Trp Phe Cys Gln Gly Ser Ile Leu Thr Gly Val Trp Val
 85                  90                  95                 100 atc ggt cat gaa tgt ggc cac cat gcc ttc agt gac tat caa tgg ata     391
Ile Gly His Glu Cys Gly His His Ala Phe Ser Asp Tyr Gln Trp Ile
                 105                 110                 115 gac gac act gtg ggc ttc atc ctt cac tct gca ctc ttc acc cct tat     439
Asp Asp Thr Val Gly Phe Ile Leu His Ser Ala Leu Phe Thr Pro Tyr
             120                 125                 130 ttc tct tgg aaa tac agt cac cgt aat cac cat gcc aac aca aac tct     487
Phe Ser Trp Lys Tyr Ser His Arg Asn His His Ala Asn Thr Asn Ser
         135                 140                 145 ctt gat aac gat gaa gta tac atc cct aaa gtt aaa tcc aag gtc aag     535
Leu Asp Asn Asp Glu Val Tyr Ile Pro Lys Val Lys Ser Lys Val Lys
     150                 155                 160 att tat tcc aaa atc ctt aac aac cct cct ggt cgc gtt ttc acc ttg     583
Ile Tyr Ser Lys Ile Leu Asn Asn Pro Pro Gly Arg Val Phe Thr Leu
165                 170                 175                 180 gct ttc aga ttg atc gtg ggt ttt cct tta tac ctt ttc acc aat gtt     631
Ala Phe Arg Leu Ile Val Gly Phe Pro Leu Tyr Leu Phe Thr Asn Val
                 185                 190                 195 tca ggc aag aaa tac gaa cgt ttt gcc aac cat ttt gat ccc atg agt     679
Ser Gly Lys Lys Tyr Glu Arg Phe Ala Asn His Phe Asp Pro Met Ser
             200                 205                 210 ccc att ttc acc gag cgt gag cat gta caa gtc ttg ctt tct gat ttt     727
Pro Ile Phe Thr Glu Arg Glu His Val Gln Val Leu Leu Ser Asp Phe
         215                 220                 225 ggt ctc ata gca gtt gct tac gtg gtt cgt caa gct gta ctg gct aaa     775
Gly Leu Ile Ala Val Ala Tyr Val Val Arg Gln Ala Val Leu Ala Lys
     230                 235                 240 gga ggt gct tgg gtg atg tgc att tac gga gtt cct gtg ctg gcc gta     823
Gly Gly Ala Trp Val Met Cys Ile Tyr Gly Val Pro Val Leu Ala Val
245                 250                 255                 260 aac gca ttc ttt gtt tta atc act tat ctt cac cac acg cat ctc tca     871
Asn Ala Phe Phe Val Leu Ile Thr Tyr Leu His His Thr His Leu Ser
                 265                 270                 275
```

```
ctg cct cac tat gat tcg act gaa tgg gac tgg atc aag gga gct ttg      919
Leu Pro His Tyr Asp Ser Thr Glu Trp Asp Trp Ile Lys Gly Ala Leu
        280                 285                 290 tgc acc atc gac aga gat ttc gga ttc ttg aat agg gtt ttc cac gac      967
Cys Thr Ile Asp Arg Asp Phe Gly Phe Leu Asn Arg Val Phe His Asp
        295                 300                 305 gtg aca cac acc cat gtg ttg cat cat ttg ata tcg tac att cct cat     1015
Val Thr His Thr His Val Leu His His Leu Ile Ser Tyr Ile Pro His
        310                 315                 320 tat cat gca aag gag gca aga gac gcc atc aaa ccg gtg ttg ggc gaa     1063
Tyr His Ala Lys Glu Ala Arg Asp Ala Ile Lys Pro Val Leu Gly Glu
325                 330                 335                 340 tac tat aag atc gac agg aca ccg atc gtg aag gca atg tgg agg gaa     1111
Tyr Tyr Lys Ile Asp Arg Thr Pro Ile Val Lys Ala Met Trp Arg Glu
                345                 350                 355 gca aag aat gca tat aca ttg agg ctg atg aag ata gcg agc acc aag     1159
Ala Lys Asn Ala Tyr Thr Leu Arg Leu Met Lys Ile Ala Ser Thr Lys
                360                 365                 370 gca cat act ggt acc aca agt tgt aaa gcc aga tcc taag              1199
Ala His Thr Gly Thr Thr Ser Cys Lys Ala Arg Ser
        375                 380

<210> SEQ ID NO 20
<211> LENGTH: 384
<212> TYPE: PRT
<213> ORGANISM: Vernonia galamensis

<400> SEQUENCE: 20

Met Gly Ala Gly

```
                225                 230                 235                 240
Val Leu Ala Lys Gly Gly Ala Trp Val Met Cys Ile Tyr Gly Val Pro
                245                 250                 255

Val Leu Ala Val Asn Ala Phe Phe Val Leu Ile Thr Tyr Leu His His
                260                 265                 270

Thr His Leu Ser Leu Pro His Tyr Asp Ser Thr Glu Trp Asp Trp Ile
                275                 280                 285

Lys Gly Ala Leu Cys Thr Ile Asp Arg Asp Phe Gly Phe Leu Asn Arg
            290                 295                 300

Val Phe His Asp Val Thr His Thr His Val Leu His His Leu Ile Ser
305                 310                 315                 320

Tyr Ile Pro His Tyr His Ala Lys Glu Ala Arg Asp Ala Ile Lys Pro
                325                 330                 335

Val Leu Gly Glu Tyr Tyr Lys Ile Asp Arg Thr Pro Ile Val Lys Ala
                340                 345                 350

Met Trp Arg Glu Ala Lys Asn Ala Tyr Thr Leu Arg Leu Met Lys Ile
                355                 360                 365

Ala Ser Thr Lys Ala His Thr Gly Thr Thr Ser Cys Lys Ala Arg Ser
    370                 375                 380

<210> SEQ ID NO 21
<211> LENGTH: 5
<212> TYPE: PRT
<213> ORGANISM: mixed function monooxygenase consensus motif
<220> FEATURE:
<221> NAME/KEY: MISC_FEATURE
<222> LOCATION: (2)..(4)
<223> OTHER INFORMATION: Xaa at position 2 is any amino acid; Xaa at
      position 3 is any amino acid; Xaa at position 4 is any amino acid;

<400> SEQUENCE: 21

His Xaa Xaa Xaa His
1               5

<210> SEQ ID NO 22
<211> LENGTH: 6
<212> TYPE: PRT
<213> ORGANISM: mixed function monooxygenase consensus motif
<220> FEATURE:
<221> NAME/KEY: MISC_FEATURE
<222> LOCATION: (2)..(5)
<223> OTHER INFORMATION: Xaa at position 2 is any amino acid; Xaa at
      position 3 is any amino acid; Xaa at position 4 is any amino acid;
      Xaa at position 5 is any amino acid;

<400> SEQUENCE: 22

His Xaa Xaa Xaa Xaa His
1               5

<210> SEQ ID NO 23
<211> LENGTH: 5
<212> TYPE: PRT
<213> ORGANISM: mixed function monooxygenase consensus motif
<220> FEATURE:
<221> NAME/KEY: MISC_FEATURE
<222> LOCATION: (2)..(3)
<223> OTHER INFORMATION: Xaa at position 2 is any amino acid; Xaa at
      position 3 is any amino acid;

<400> SEQUENCE: 23

His Xaa Xaa His His
1               5
```

```
<210> SEQ ID NO 24
<211> LENGTH: 6
<212> TYPE: PRT
<213> ORGANISM: mixed function monooxygenase consensus motif
<220> FEATURE:
<221> NAME/KEY: MISC_FEATURE
<222> LOCATION: (2)..(4)
<223> OTHER INFORMATION: Xaa at position 2 is any amino acid; Xaa at
      position 3 is any amino acid; Xaa at position 4 is any amino acid;

<400> SEQUENCE: 24

His Xaa Xaa Xaa His His
1               5
```